US008597193B2

(12) United States Patent
Grunwald et al.

(10) Patent No.: US 8,597,193 B2
(45) Date of Patent: *Dec. 3, 2013

(54) APPARATUS AND METHOD FOR ENDOVASCULAR DEVICE GUIDING AND POSITIONING USING PHYSIOLOGICAL PARAMETERS

(75) Inventors: Sorin Grunwald, Palo Alto, CA (US); Fiona Maria Sander, Los Altos Hills, CA (US); Wilfred J. Samson, Saratoga, CA (US); Bradley Hill, Santa Clara, CA (US); E. Tina Cheng, Union City, CA (US)

(73) Assignee: VasoNova, Inc., Menlo Park, CA (US)

( * ) Notice: Subject to any disclaimer, the term of this patent is extended or adjusted under 35 U.S.C. 154(b) by 1290 days.

This patent is subject to a terminal disclaimer.

(21) Appl. No.: 12/147,401

(22) Filed: Jun. 26, 2008

(65) Prior Publication Data

US 2009/0005675 A1 Jan. 1, 2009

Related U.S. Application Data

(63) Continuation-in-part of application No. 11/431,140, filed on May 8, 2006, and a continuation-in-part of application No. 11/431,118, filed on May 8, 2006, and a continuation-in-part of application No. 11/431,093, filed on May 8, 2003, now abandoned, and a continuation-in-part of application No. 11/430,511, filed on May 8, 2006, now Pat. No. 8,409,103.

(60) Provisional application No. 60/937,280, filed on Jun. 26, 2007, provisional application No. 60/957,316, filed on Aug. 22, 2007, provisional application No. 61/023,183, filed on Jan. 24, 2008, provisional application No. 60/678,209, filed on May 6, 2005, provisional application No. 60/682,002, filed on May 18, 2005, provisional application No. 60/678,209, filed on May 6, 2005, provisional application No. 60/682,002, filed on May 18, 2005.

(51) Int. Cl.
*A61B 8/06* (2006.01)

(52) U.S. Cl.
USPC .......................................................... 600/468

(58) Field of Classification Search
USPC ......... 600/437, 462, 466, 467, 472, 454, 468, 600/724
See application file for complete search history.

(56) References Cited

U.S. PATENT DOCUMENTS

| 3,565,062 A | 2/1971 | Kuris |
| 4,143,650 A | 3/1979 | Hatke |

(Continued)

FOREIGN PATENT DOCUMENTS

| DE | 4319033 C1 | 6/1994 |
| EP | 0917069 A1 | 5/1999 |

(Continued)

OTHER PUBLICATIONS

Benchimol et al.; Right atrium and superior vena cava flow velocity in man measured with the doppler-catheter flowmeter-telemetry system; The Amer. J of Med.; vol. 48; pp. 303-309; 1970.

(Continued)

*Primary Examiner* — Tse Chen
*Assistant Examiner* — Rochelle Reardon
(74) *Attorney, Agent, or Firm* — Shay Glenn LLP

(57) ABSTRACT

An endovascular access and guidance system has an elongate body with a proximal end and a distal end; a non-imaging ultrasound transducer on the elongate body configured to provide in vivo non-image based ultrasound information of the vasculature of the patient; an endovascular electrogram lead on the elongate body in a position that, when the elongate body is in the vasculature, the endovascular electrogram lead electrical sensing segment provides an in vivo electrogram signal of the patient; a processor configured to receive and process a signal from the non-imaging ultrasound transducer and a signal from the endovascular electrogram lead; and an output device configured to display a result of information processed by the processor.

52 Claims, 20 Drawing Sheets

(56) References Cited

U.S. PATENT DOCUMENTS

| | | | |
|---|---|---|---|
| 4,324,258 A | 4/1982 | Huebscher et al. |
| 4,354,502 A | 10/1982 | Colley et al. |
| 4,362,166 A | 12/1982 | Furler et al. |
| 4,503,861 A | 3/1985 | Entrekin |
| 4,549,879 A | 10/1985 | Groshong et al. |
| 4,644,960 A | 2/1987 | Johans |
| 4,667,679 A | 5/1987 | Sahota |
| 4,692,148 A | 9/1987 | Kantrowitz et al. |
| 4,706,681 A | 11/1987 | Breyer et al. |
| 4,790,831 A | 12/1988 | Skribiski |
| 4,849,172 A | 7/1989 | Yafuso et al. |
| 4,856,529 A | 8/1989 | Segal |
| 4,896,677 A | 1/1990 | Kaneko et al. |
| 4,966,148 A | 10/1990 | Millar |
| 4,967,753 A | 11/1990 | Haase et al. |
| 4,979,510 A | 12/1990 | Franz et al. |
| 5,038,789 A | 8/1991 | Frazin et al. |
| 5,046,497 A | 9/1991 | Millar |
| 5,047,930 A | 9/1991 | Martens et al. |
| 5,058,597 A | 10/1991 | Onoda et al. |
| 5,078,148 A | 1/1992 | Nassi et al. |
| 5,078,678 A | 1/1992 | Katims |
| 5,107,841 A | 4/1992 | Sturgill |
| 5,174,295 A | 12/1992 | Christian et al. |
| 5,190,045 A * | 3/1993 | Frazin ............... 600/463 |
| 5,207,226 A | 5/1993 | Bailin et al. |
| 5,220,924 A | 6/1993 | Frazin |
| 5,269,289 A | 12/1993 | Takehana et al. |
| 5,271,404 A | 12/1993 | Corl et al. |
| 5,311,871 A | 5/1994 | Yock |
| 5,431,628 A | 7/1995 | Millar |
| 5,477,858 A | 12/1995 | Norris et al. |
| 5,492,125 A | 2/1996 | Kim et al. |
| 5,546,949 A | 8/1996 | Frazin et al. |
| 5,566,674 A | 10/1996 | Weng |
| 5,575,286 A | 11/1996 | Weng et al. |
| 5,588,432 A | 12/1996 | Crowley |
| 5,640,961 A | 6/1997 | Verdonk |
| 5,657,760 A | 8/1997 | Ying et al. |
| 5,666,958 A | 9/1997 | Rothenberg et al. |
| 5,669,389 A | 9/1997 | Rotteveel et al. |
| 5,693,032 A | 12/1997 | Bierman |
| 5,697,377 A | 12/1997 | Wittkampf et al. |
| 5,722,959 A | 3/1998 | Bierman |
| 5,733,323 A | 3/1998 | Buck et al. |
| 5,749,364 A | 5/1998 | Sliwa et al. |
| 5,782,766 A | 7/1998 | Weng et al. |
| 5,785,657 A | 7/1998 | Breyer et al. |
| 5,795,298 A | 8/1998 | Vesely et al. |
| 5,803,083 A | 9/1998 | Buck et al. |
| 5,857,973 A | 1/1999 | Ma et al. |
| 5,860,951 A | 1/1999 | Eggers et al. |
| 5,876,342 A | 3/1999 | Chen et al. |
| 5,878,746 A | 3/1999 | Lemelson et al. |
| 5,891,036 A | 4/1999 | Izumi |
| 5,897,488 A * | 4/1999 | Ueda ............... 600/143 |
| 5,908,385 A | 6/1999 | Chechelski et al. |
| 5,935,143 A | 8/1999 | Hood |
| 5,938,603 A | 8/1999 | Ponzi |
| 5,999,846 A | 12/1999 | Pardey et al. |
| 6,007,491 A | 12/1999 | Ling et al. |
| 6,059,731 A | 5/2000 | Seward et al. |
| 6,083,170 A | 7/2000 | Ben-Haim |
| 6,120,445 A | 9/2000 | Grunwald |
| 6,179,781 B1 | 1/2001 | Phillips |
| 6,179,782 B1 | 1/2001 | Cuce |
| 6,213,947 B1 | 4/2001 | Phillips |
| 6,251,073 B1 | 6/2001 | Imran et al. |
| 6,264,611 B1 | 7/2001 | Ishikawa et al. |
| 6,364,838 B1 | 4/2002 | Freiburger et al. |
| 6,500,130 B2 | 12/2002 | Kinsella et al. |
| 6,520,916 B1 | 2/2003 | Brennen |
| 6,542,626 B1 | 4/2003 | Brouwer et al. |
| 6,551,244 B1 | 4/2003 | Gee |
| 6,556,695 B1 | 4/2003 | Packer et al. |
| 6,561,979 B1 | 5/2003 | Wood et al. |
| 6,591,144 B2 | 7/2003 | Pigott |
| 6,594,524 B2 | 7/2003 | Esteller et al. |
| 6,612,992 B1 | 9/2003 | Hossack et al. |
| 6,638,243 B2 | 10/2003 | Kupiecki |
| 6,685,648 B2 * | 2/2004 | Flaherty et al. ............... 600/464 |
| 6,689,119 B1 | 2/2004 | Di Caprio et al. |
| 6,695,785 B2 | 2/2004 | Brisken et al. |
| 6,704,590 B2 | 3/2004 | Haldeman |
| 6,719,756 B1 | 4/2004 | Muntermann |
| 6,733,454 B1 | 5/2004 | Bakircioglu et al. |
| 6,740,590 B1 | 5/2004 | Yano et al. |
| 6,749,606 B2 | 6/2004 | Keast et al. |
| 6,814,702 B2 | 11/2004 | Redano |
| 6,866,677 B2 | 3/2005 | Douk et al. |
| 6,896,658 B2 | 5/2005 | Ji et al. |
| 6,931,269 B2 | 8/2005 | Terry |
| 6,973,352 B1 | 12/2005 | Tsutsui et al. |
| 7,037,290 B2 | 5/2006 | Gardeski et al. |
| 7,043,293 B1 | 5/2006 | Baura |
| 7,150,716 B2 | 12/2006 | Jones et al. |
| 7,200,435 B2 | 4/2007 | Ricci et al. |
| 7,204,798 B2 | 4/2007 | Zdeblick et al. |
| 7,225,013 B2 | 5/2007 | Geva et al. |
| 7,346,393 B2 | 3/2008 | Spinelli et al. |
| 7,367,949 B2 | 5/2008 | Korhonen et al. |
| 7,393,501 B2 | 7/2008 | Zumeris et al. |
| 7,422,563 B2 | 9/2008 | Roschak et al. |
| 7,433,853 B2 | 10/2008 | Brockway et al. |
| 7,485,095 B2 | 2/2009 | Shusterman |
| 7,599,730 B2 | 10/2009 | Hunter et al. |
| 7,627,386 B2 | 12/2009 | Mo et al. |
| 7,640,055 B2 | 12/2009 | Geva et al. |
| 7,668,579 B2 | 2/2010 | Lynn |
| 7,697,972 B2 | 4/2010 | Verard et al. |
| 7,708,696 B2 | 5/2010 | Ritter et al. |
| 7,733,224 B2 | 6/2010 | Tran |
| 7,794,407 B2 | 9/2010 | Rothenberg |
| 7,833,221 B2 | 11/2010 | Voegele et al. |
| 7,966,061 B2 | 6/2011 | Al-Abed et al. |
| 7,981,038 B2 | 7/2011 | Kanade et al. |
| 7,991,458 B2 | 8/2011 | Hardahl et al. |
| 8,046,052 B2 | 10/2011 | Verard et al. |
| 8,052,648 B2 | 11/2011 | Dikeman et al. |
| 8,060,185 B2 | 11/2011 | Hunter et al. |
| 2002/0045810 A1 | 4/2002 | Ben-Haim |
| 2002/0087156 A1 | 7/2002 | Maguire et al. |
| 2002/0111548 A1 | 8/2002 | Swanson et al. |
| 2002/0151790 A1 | 10/2002 | Abend |
| 2002/0156363 A1* | 10/2002 | Hunter et al. ............... 600/410 |
| 2002/0168618 A1 | 11/2002 | Anderson et al. |
| 2002/0188257 A1 | 12/2002 | Bierman |
| 2003/0083717 A1 | 5/2003 | Mlynski et al. |
| 2003/0109785 A1 | 6/2003 | Buck et al. |
| 2004/0011358 A1 | 1/2004 | Smaldone et al. |
| 2004/0039436 A1 | 2/2004 | Spenser et al. |
| 2004/0102719 A1 | 5/2004 | Keith et al. |
| 2004/0116809 A1 | 6/2004 | Chow et al. |
| 2004/0116969 A1* | 6/2004 | Owen et al. ............... 607/6 |
| 2004/0158143 A1 | 8/2004 | Flaherty et al. |
| 2004/0254523 A1 | 12/2004 | Fitzgerald et al. |
| 2005/0085718 A1 | 4/2005 | Shahidi |
| 2005/0148836 A1 | 7/2005 | Kleen et al. |
| 2005/0159738 A1 | 7/2005 | Visram et al. |
| 2006/0079868 A1 | 4/2006 | Makin et al. |
| 2006/0084883 A1 | 4/2006 | Linker |
| 2006/0094923 A1 | 5/2006 | Mate |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0167738 A1 | 7/2007 | Timinger et al. |
| 2007/0265526 A1 | 11/2007 | Govari et al. |
| 2007/0276334 A1 | 11/2007 | Bierman et al. |
| 2008/0058607 A1 | 3/2008 | Watrous |
| 2008/0161669 A1 | 7/2008 | Hauck et al. |
| 2008/0188740 A1 | 8/2008 | Diaz et al. |
| 2009/0143740 A1 | 6/2009 | Bierman et al. |
| 2009/0156926 A1 | 6/2009 | Messerly et al. |

| | | | |
|---|---|---|---|
| 2009/0177090 | A1 | 7/2009 | Grunwald et al. |
| 2009/0182283 | A1 | 7/2009 | Sloan |
| 2009/0234328 | A1 | 9/2009 | Cox et al. |
| 2009/0259124 | A1 | 10/2009 | Rothenberg |
| 2009/0262977 | A1 | 10/2009 | Huang et al. |
| 2009/0287070 | A1 | 11/2009 | Baker, Jr. |
| 2009/0287191 | A1 | 11/2009 | Ferren et al. |
| 2010/0036227 | A1 | 2/2010 | Cox et al. |
| 2010/0204569 | A1 | 8/2010 | Burnside et al. |
| 2011/0257600 | A1 | 10/2011 | Kessler |
| 2012/0035434 | A1 | 2/2012 | Ferren et al. |

FOREIGN PATENT DOCUMENTS

| | | | |
|---|---|---|---|
| EP | 1181895 | A2 | 2/2002 |
| JP | 62500703 | A | 3/1987 |
| JP | 62-236532 | | 10/1987 |
| JP | 3205040 | A | 9/1991 |
| JP | 4017843 | | 1/1992 |
| JP | U-7-3608 | | 1/1995 |
| JP | H07505791 | A1 | 6/1995 |
| JP | 08-229044 | | 9/1995 |
| JP | 09-253084 | | 9/1997 |
| JP | 10-277039 | | 10/1998 |
| JP | 2004500210 | | 1/2004 |
| JP | 2004130114 | | 4/2004 |
| JP | 2006513731 | | 4/2006 |
| KR | 1020090019762 | | 2/2009 |
| WO | WO 98/08440 | A1 | 3/1998 |
| WO | WO 01/70303 | A2 | 9/2001 |
| WO | WO2006/051523 | A2 | 5/2006 |
| WO | WO 2007/047360 | A2 | 4/2007 |

OTHER PUBLICATIONS

Benchimol et al.; Bidirectional blood flow velocity in the cardiac chambers and great vessels studied with the doppler ultrasonic flowmeter; The Amer. J of Med.; vol. 52; pp. 467-473; 1972.

Kalmanson et al.; Letter to the Editor; "Directional vs bidirectional doppler velocimeter"; Am. Heart J.; vol. 83; No. 3; pp. 437; Mar. 1972.

Lewis et al.; A Study of Normal and abnormal femoral venous flow velocity using a directional doppler; Br. J. Surg: vol. 59, No. 4; pp. 303; Apr. 1972.

Radke et al.; Control of the placement of a central venous catheter using doppler ultrasound; Der Anaesthesist May 1990; vol. 39; No. 5; pp. 283-287; May 1990.

Bossert et al.; Swan-Ganz catheter-induced severe complications in cardiac surgery: right ventricular perforation, knotting, and rupture of a pulmonary artery; J. Car. Surg.; vol. 21; No. 3; pp. 292-295; May/Jun. 2006.

Fearon et al.; Evaluating intermediate coronary lesions in the cardiac catheterization laboratory; Rev Cardiovasc Med; vol. 4; No. 1; pp. 1-7; 2003.

Hellerstein et al.; Recording of intracavity potentials through a single lumen, saline filled cardiac catheter; P.S.E.B.M.,; vol. 71; pp. 58-60; 1949.

Naylor; Reduction of malposition in peripherally inserted central catheters with tip location system; JAVA; vol. 12; No. 1; pp. 29-31; 2007.

Pittiruti et al.; The EKG method for positioning the tip of PICCs; results from two preliminary studies;JAVA; vol. 13; No. 4; pp. 112-119; 2008.

Stas et al.; Peroperative intravasal electrographic control of catheter tip position in access ports placed by venous cut-down technique;EJSO; vol. 27; pp. 316-320; 2001.

Bidoggia et al.; Transseptal left heart catheterization: usefulness of the intracavitary electrocardiogram in the localization of the fossa ovalis; Catheterization and Cardiovascular Diagnosis; New York, NY; vol. 24; No. 3; pp. 221-225; Nov. 1, 1991.

McGee, et al.; Accurate placement of central venous catheters: A prospecitve, randomized, multicenter trial; Critical Care Medicine, vol. 21, No. 8, pp. 1118-1123, Aug. 1993.

Starr, et al.; EKG guided placement of subclavian CVP catheters using J-wire; Ann. Surg.; vol. 204, No. 6, pp. 673-676, Dec. 1986.

Schummer et al.; Central venous catheters—the inability of 'intra-atrial ECG' to prove adequate positioning; British Jour. of Anaesthesia, vol. 93, No. 2; pp. 193-198, 2004.

Grunwald et al; U.S. Appl. No. 12/147,413 entitled "Apparatus and method for vascular access," filed Jun. 26, 2008.

Qi et al.; U.S. Appl. No. 13/292,010 entitled "Endovascular navigation system and method", filed Nov. 8, 2011.

Brunner, Eberhard; Ultrasound system considerations and their impact on front-end components; Analog Devices, Inc.; pp. 1-19; May-Jun. 2002.

* cited by examiner

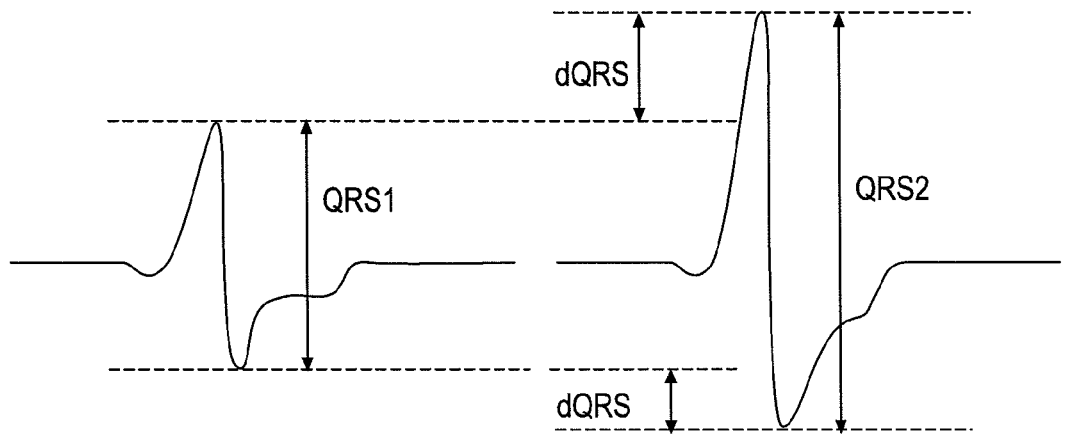
① ECG Baseline
No P Wave
② ECG Endovascular
Proximal to Sino-Atrial Node
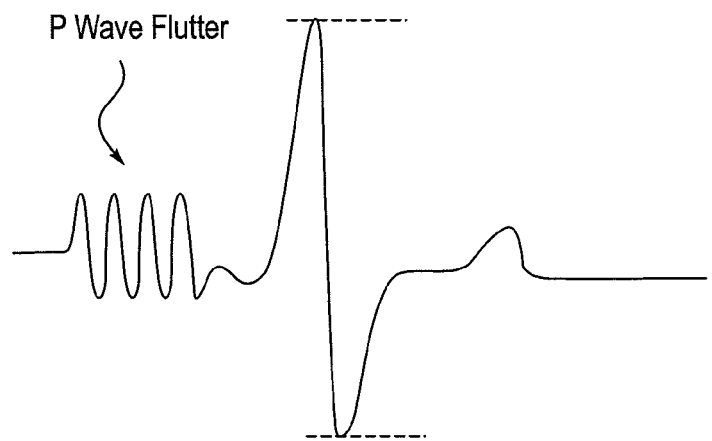
③ ECG Endovascular
Proximal to Sino-Atrial Node
FIG. 12

APPARATUS AND METHOD FOR ENDOVASCULAR DEVICE GUIDING AND POSITIONING USING PHYSIOLOGICAL PARAMETERS

CROSS-REFERENCE TO RELATED APPLICATIONS

This application claims the benefit of U.S. Provisional Patent Application No. 60/937,280 filed on Jun. 26, 2007 by Sorin Grunwald et al., entitled "Apparatus and Method for Vascular Access"; U.S. Provisional Patent Application No. 60/957,316 filed on Aug. 22, 2007 by Sorin Grunwald et al., entitled "Apparatus and Method for Endovascular Guidance"; and U.S. Provisional Patent Application No. 61/023,183 filed on Jan. 24, 2008 by Sorin Grunwald et al., entitled "Configurations of Guided Endovascular Access devices", each of which is incorporated herein by reference in its entirety.

This application is also a continuation-in-part of U.S. Non-Provisional patent application Ser. No. 11/431,140 filed on May 8, 2006 by Sorin Grunwald et al., entitled "Endovenous Access and Guidance System Utilizing Non-Image Based Ultrasound", now publication no. 2007-0016072-A1; U.S. Non-Provisional patent application Ser. No. 11/431,118 filed on May 8, 2006 by Sorin Grunwald et al., entitled "Endovascular Access and Guidance System Utilizing Divergent Beam Ultrasound", now publication no. 2007-0016070-A1; U.S. Non-Provisional patent application Ser. No. 11/431,093 filed on May 8, 2006 by Sorin Grunwald et al., entitled "Ultrasound Sensor", now publication no. 2007-0016069-A1; and U.S. Non-Provisional patent application Ser. No. 11/430,511 filed on May 8, 2006 by Sorin Grunwald et al., entitled "Ultrasound Methods of Positioning Guided Vascular Access Devices in the Venous System", now publication no. 2007-0016068-A1, all of which claim the benefit of U.S. Provisional Patent Application No. 60/678,209 filed on May 6, 2005 by Sorin Grunwald et al., entitled "Method and Apparatus for Intravascular Catheter Guiding and Positioning" and U.S. Provisional Patent Application No. 60/682,002 filed on May 18, 2005 by Sorin Grunwald et al., entitled "Method and Apparatus for Intravascular Catheter Guiding and Positioning", each of which is incorporated herein by reference in their entirety.

BACKGROUND OF THE INVENTION

The invention relates to the guidance, positioning and placement confirmation of intravascular devices, such as catheters, stylets, guidewires and other elongate bodies that are typically inserted percutaneously into the venous or arterial vasculature, including flexible elongate bodies. Currently these goals are achieved using x-ray imaging and in some cases ultrasound imaging. This invention provides a method to substantially increase the accuracy and reduce the need for imaging related to placing an intravascular catheter or other device. Reduced imaging needs also reduce the amount of radiation that patients are subjected to, reduce the time required for the procedure, and decrease the cost of the procedure by reducing the time needed in the radiology department.

The vasculature of mammals has long been accessed to provide therapy, administer pharmacological agents and meet other clinical needs. Numerous procedures exist in both venous and arterial systems and are selected based on patient need. One challenge common to all vascular-based therapies is health care provider access to the specific location or section of the vascular tree.

One common venous access procedure is central venous access. Central venous access is the placement of a venous catheter in a vein that leads directly to the heart. Central venous catheters are ubiquitous in modern hospital and ambulatory medicine, with up to 8 million insertions per year in the U.S. and a similar number outside the U.S.

Venous access devices are most often used for the following purposes:
- Administration of medications, such as antibiotics, chemotherapy drugs, and other IV drugs
- Administration of fluids and nutritional compounds (hyperalimentation)
- Transfusion of blood products
- Hemodialysis
- Multiple blood draws for diagnostic testing.

Central venous access devices are small, flexible tubes placed in large veins for people who require frequent access to their bloodstream. The devices typically remain in place for long periods: week, months, or even longer.

Central venous access devices are usually inserted in 1 of 3 ways:
a) Directly via a catheter. Catheters are inserted by tunneling under the skin into either the subclavian vein (located beneath the collarbone) or into the internal jugular vein (located in the neck). The part of the catheter where medications are administered or blood drawn remains outside of the skin.
b) Through a port. Unlike catheters, which exit from the skin, ports are placed completely below the skin. With a port, a raised disk about the size of a quarter or half dollar is felt underneath the skin. Blood is drawn or medication delivered by placing a tiny needle through the overlying skin into the port or reservoir.
c) Indirectly via a periphal vein. Peripherally inserted central catheter (PICC) lines, unlike central catheters and ports, are not inserted directly into the central vein. A PICC line is inserted into a large vein in the arm and advanced forward into the larger subclavian vein.

Central catheters and ports are usually inserted by a surgeon or surgical assistant in a surgical suite. An alternative is placement under the guidance of a special x-ray machine so that the person inserting the line can make sure that the line is placed properly. A PICC line can be put in at bedside, usually by a specially trained nurse. In this later case, confirmation by X-ray is currently required for assessing the success of the PICC placement.

Traditional surgically placed central catheters are increasingly being replaced by peripherally inserted central venous access devices. PICC lines usually cause fewer severe complications than central venous access devices. Peripherally-Inserted-Central-Catheter (PICC) is used in a variety of clinical procedures. The PICC line placement procedure is performed by interventional radiologists to deliver long-term drug delivery, chemotherapy procedures, delivery of intravenous medications or intravenous nutrition (hyperalimentation) and taking blood samples via a Hickman catheter. Insertion of PICC lines is a routine procedure in that it is carried out fairly often for a variety of treatments, and more than once in the same patient when the catheter is to be left in place for any length of time. Even though it is routine, it is a very time and labor-intensive procedure for the hospital staff, which also makes it expensive. During the procedure the physician or nurse places the catheter into a superficial arm vein such as the cephalic, basilic, antecubital, median cubital, or other superficial vein with the goal of having the distal end of the catheter reach the superior vena cava. After entering the superficial vein around the area where the arm bends (elbow), the catheter is advanced up the subclavian vein, then the brachiocephalic vein and finally it enters the superior vena cava. One caveat is to make sure that the PICC line does not enter the jugular vein via the subclavian vein.

Hemodialysis therapy via a hemodialysis catheter is another example of a procedure requiring central venous access. A dialysis catheter is a specialized type of central venous catheter used for dialysis. Dialysis catheter placement involves the insertion of a catheter into a large vessel, utilizing X-ray guidance. The challenges of inserting a hemodialysis catheter in terms of guidance and positioning are similar to those of a central venous catheter, only they are typically larger and require a peel-away sheath for insertion.

Another therapy achieved via providing access to the venous system is the percutaneous treatment of varicose veins. Published population studies indicate that approximately 25 million people in the U.S. and 40 million people in Western Europe suffer from symptomatic venous reflux disease. Percutaneous treatment of varicose veins involves the placement of an energy delivery catheter (laser or RF) after navigation the vasculature to locate the treatment site. One common treatment site is the sapheno-femoral junction and less common sites are the sapheno-popliteal junction and sites of perforator veins, which connect the superficial venous system to the deep venous system of the leg at a variety of different locations, mostly below the knee. As such, in the case of percutaneous treatment of varicose veins using specific venous junctions, the position the laser or the RF catheter at an optimal location with respect to the venous junction is critical for the success of the intervention.

In addition to guiding the catheter through the vasculature, the location of the catheter tip is very important to the success of the procedure. Catheters will generally function equally well for pressure measurement and fluid infusion if the tip is situated in any major vein, above or below the heart. For dialysis or the infusion of irritant/hypertonic fluids, a high rate of blood flow past the catheter tip is desirable and this requires the placement of the luminal opening in as large a vessel as possible. However, the package inserts of many central venous catheters give very strong warnings about the absolute requirement for catheter tips to lie outside the heart to avoid perforation and subsequent pericardial tamponade. Likewise positioning the catheter tip away from small peripheral veins is important to avoid damaging the vein wall or occluding the vein due the caustic effects of the infusing solution. It is also of major interest that the catheter tip stays in place after placement for the whole duration of the treatment. If the catheter tip moves, not only its effectiveness diminished but, in some situations, it can perforate the heart. In the United States, the Food and Drug Administration has issued advice emphasizing this point. Typically, the interventional radiologist uses a fluoroscopic agent to delineate the veins in the body and subsequently verifies the correct positioning of the catheter tip using a post-operative X-ray. Currently, post-operative X-ray is performed routinely while some studies have shown that only 1.5% of the cases are subject to complications that would indeed require X-ray imaging.

Current methods for guiding PICC lines include external electromagnetic sensors and intravascular, e.g, ECG. N the case of electromagnetic sensors, the endovascular device is guided by assessing the distance between an electromagnetic element at the tip of the device, e.g., a coil and an external (out of body) receiver. This method is inaccurate because it does not actually indicate location in the vascular but distance to an outside reference. In the case of ECG-guided catheters, the classic increase in P-wave size, known as "P-atriale", is a widely accepted criterion for determining location of central venous catheter tips in the proximity of the sino-atrial node. Current methods include using a catheter filled with saline and an ECG adaptor at the proximal end connected to an ECG system. This method is inaccurate because it does not indicate location in the blood vessel but the proximity of the sino-atrial node. Because of known inaccuracies, all the current methods in use do explicitly require the use of a confirmatory chest X-ray to verify and confirm location of the tip of the endovascular device at the desired target in the vasculature. Most prior art relating to the use of intravascular ultrasound or electrical mapping of heart activity for diagnostic and therapeutic purposes addresses problems independently: some addresses ultrasound guidance on the arterial side such as that described by Franzin in Doppler-guided retrograde catheterization using transducer equipped guide wire (U.S. Pat. No. 5,220,924) or that described by Katims in Method and apparatus for locating a catheter adjacent to a pacemaker node of the heart (U.S. Pat. No. 5,078,678). Such approaches have intrinsic limitations which does not make them suited to solve the problem addressed by the current invention. The limitations of the Frazin approach have been extensively explained in VasoNova patent applications US 20070016068, 20070016069, 20070016070, and 20070016072. Limitations of an approach based exclusively on measuring right-atrial electrocardiograms have been described in the literature, for example in [1]: W. Schummer et al., Central venous catheters—the inability of 'intra-atrial ECCG' to prove adequate positioning, British Journal of Anaesthesia, 93 (2): 193-8, 2004.

What is needed are methods and apparatuses to optimize guidance and placement of catheters in order to reduce the risk associated with wrong placement and the cost associated with the X-ray imaging. Further there remains a need for a catheter guidance and placement system that may be used to safely guide and place catheters in healthcare provider or clinical environments other than in the radiology department or surgical suite wherein a radiological or other external imaging modality is used to confirm catheter placement. As such, there remains a need in the medical arts for instruments, systems and associated methods for locating, guiding and placing catheters and other instruments into the vasculature generally. In addition remains a need in the medical arts for instruments, systems and associated methods for locating, guiding and placing catheters and other instruments into the vasculature to meet the challenges presented by the unique characteristics and attributes specific to the vascular system of interest. The current invention overcomes the above described limitations by making use of physiological parameters like blood flow and ECG measured in the vasculature and is based on the fact that physiological parameters and their relationship is unique to the locations in the vasculature where the endovascular devices needs to be placed. The current invention describes an apparatus for identifying the unique physiological signature of a certain location in the vasculature and a method to guide the endovascular device to that location based on the physiological signatures.

SUMMARY OF THE INVENTION

An aspect of the invention includes an endovenous access and guidance system. The system comprises: an elongate flexible member adapted and configured to access the vasculature of a patient; sensors disposed at a distal end of the elongate flexible member and configured to provide intravascular electrocardiogram signals and blood flow velocity profile information of the vasculature of the patient using in vivo non-image based ultrasound or near infrared light, temperature measurements, pressure measurements and other types of sensors and measurements which can provide blood velocity information, a processor configured to receive, process, and correlate blood flow velocity information and intravascular electrocardiogram signals of the vasculature of the patient provided by the sensors and to provide position information regarding the position of the distal end of the elongate flexible member within the vasculature of the patient; and an output device adapted to output the position information from the processor. In some embodiments, the elongate flexible member is further adapted to provide a catheter, a guidewire, and/or a stylet. In other embodiments, the device is adapted to deliver therapy to a patient, or provide vascular access for another device. In still another embodiment, the system is adapted to further comprise a sensor attachment mechanism adapted to removably detach the sensors from the elongate flexible member while the elongate flexible member remains in the vasculature of the patient. In yet another embodiment, the system is configured such that the processor processes in vivo non-image based ultrasound information and intravascular electrocardiogram signals of the vasculature system of the patient provided by the sensors to indicate in the output information the proximity of the sensors to a structure within the vasculature of the patient. In still other embodiments, the processor can be further configured to process in vivo non-image based ultrasound information and intravascular electrocardiogram signals of the vasculature system of the patient to indicate in the output information movement of the elongate flexible member in a desired direction within the vasculature of the patient. Alternatively, the processor is further configured to process in vivo non-image based ultrasound information and intravascular electrocardiogram signals of the vasculature system of the patient based on a parameter selected from a group consisting of: a blood flow direction, a blood flow velocity, e.g., the highest, the lowest, the mean or the average velocity, a blood flow signature pattern, a pressure signature pattern, A-mode information, a preferential non-random direction of flow, the shape of the different waveforms and complexes charactering the intravascular electrocardiogram, e.g., P-wave, QRS complex, T-wave, the peak-to-peak amplitudes, the absolute and relative amplitude changes and other distinctive elements of the intravascular ECG. Such parameters can be used either individually or in combination in order to increase the reliability of detecting locations in the vasculature based on functional behavior and physiological parameters measurements, for example the P-wave changes indicative or the proximity of the sinoatrial node near the caval-atrial junction and together with the venous blood flow signature pattern indicative of the caval-atrial junction. Furthermore, the behavior of such parameters in time is also indicative of location in the vasculature, e.g. evident pulsatile variations of the blood flow signature pattern may be indicative of a location in the internal jugular vein. In another aspect of the invention, the system further comprises a catheter, stylet, or guidewire electrode for recording intravascular electrocardiograms which can also be used as a mechanism for steering, centering, and separating the endovascular member away from the vessel wall.

Another aspect of the invention includes a method for positioning an instrument in the vasculature of a body. The method comprises the steps of: accessing the vascular system of the body; positioning an instrument in the vascular system of the body; using the instrument to transmit an ultrasound signal into the vascular system of the body; using the instrument to receive a reflected ultrasound signal from the vasculature indicating flow rates between 2 and 20 cm/s; using the instrument to measure intravascular electrical activity of the heart, processing the reflected ultrasound and electrocardiogram signals to determine one or more parameters and their temporal behavior from a group consisting of: a blood flow direction, a blood flow velocity, e.g., the highest, the lowest, the mean or the average velocity, a blood flow signature pattern, a pressure signature pattern, A-mode information, a preferential non-random direction of flow, the shape of the different waveforms and complexes charactering the intravascular electrocardiogram, e.g., P-wave, QRS complex, T-wave, the peak-to-peak amplitudes, the absolute and relative amplitude changes and other distinctive elements of the intravascular ECG; and advancing the instrument within the vasculature using the one or more of the determined parameter or parameters within the vasculature. In yet other embodiments, processing the reflected ultrasound signal and the intravascular or intracardiac electrocardiogram signal and their correlation to determine the position of the instrument relative to the caval-atrial junction and other specific location within the body is performed. In other aspects of the invention, the specific target vasculature for positioning an instrument is included, for example, the specific structure is a valve of a heart, a blood vessel wall, a heart wall, a pacemaker node of the heart. In another aspect of the invention, the method can further comprise identifying a certain obstructing structure in a blood vessel or within the lumen of an endovascular device which can obstruct either the advancement of the endovascular device in the blood vessel or the delivery of a payload through a lumen of the devices, e.g., a blood clot In another aspect of the invention, the method can further comprise: using the instrument determine a location to secure a device within the vasculature of a body; and securing the device to the body to maintain the device in the location determined by the instrument. In still another aspect of the method, the method can further comprise: using the instrument to calculate the current position of the device; and determining if the device is in the location determined by the instrument by comparing the current calculated position of the device to the location determined by the instrument. In some aspects of the method, the method further comprises processing the reflected ultrasound signal and the intravascular or intracardiac electrocardiogram to determine the position of the instrument within the lower third of the superior vena cava. In still other aspects the method further comprising processing the reflected ultrasound signal and the intravascular or intracardiac electrocardiogram to determine the position of the instrument within the right atrium relative to the coronary sinus. In still other aspects, the method further comprising processing the reflected ultrasound signal and the intravascular or intracardiac electrocardiogram to determine the position of the instrument within the left atrium relative to a pulmonary vein. In one embodiment, the methods described above comprise the following steps: 1. The sensor-based endovascular devices having at least a Doppler sensor and an intravascular ECG sensor is placed in the vasculature of the patient through a vascular access site. A baseline ECG and a baseline blood velocity profile are captured in the blood vessel at location A1 and displayed and/or stored by the system. Specifically one or more of the following physiological measurements are considered: the blood velocity profile, the highest, the lowest, the mean or the average blood velocity, the P-wave amplitude, the QRS-complex amplitude and the ratio between the P-wave and the QRS-complex amplitudes, 2. The sensor-based endovascular device is advanced to a location A2 in the vasculature and the same parameters are again analyzed which have been analyzed at location A1. 3. Several algorithms are then applied to compare the information at location A2 with the information at location A1 as described in the present invention. 4. In addition, the information at location A2 can be compared against information contained in a knowledge base regarding the relationship between such information and locations in the vasculature, as further described in the present invention. 5. Decision criteria are then applied to the processed information in order to establish correlation with the anatomical location as further described in the present invention. In another embodiment, the P-wave and/or the QRS complex of the ECG can be used to gate the acquisition/and or analysis of the blood flow velocity information in order to restrict the analysis to only a segment of the heart cycle and thus increase reliability of information and accuracy of location identification.

In one embodiment of the invention, there is an endovascular access and guidance system including some or all of the following components: an elongate body with a proximal end and a distal end; a non-imaging ultrasound transducer on the elongate body configured to provide in vivo non-image based ultrasound information of the vasculature of the patient; an endovascular electrogram lead on the elongate body in a position that, when the elongate body is in the vasculature, the endovascular electrogram lead electrical sensing segment provides an in vivo electrogram signal of the patient; a processor configured to receive and process a signal from the non-imaging ultrasound transducer and a signal from the endovascular electrogram lead; and an output device configured to display a result of information processed by the processor.

These components may be modified or removed depending upon the specific application of a guidance system. The output device may display a result related to a position of the elongate body within the vasculature of the patient. The processor may be configured to process a signal from the non-image ultrasound transducer and to indicate in the output device information related to the presence of a structure in the field of view of the non-imaging ultrasound transducer. A result of information processed by the processor comprises: an indication of a position or a movement of the elongate body within the vasculature based on in vivo non-image based ultrasound information and in vivo electrogram information.

The endovascular access and guidance system may also include a driver coupled to the ultrasound transducer adapted to drive the ultrasound transducer in response to an electrogram signal. The driver coupled to the ultrasound transducer is adapted to drive the ultrasound transducer in a plurality of ultrasound transmission modes.

The endovascular access and guidance system may also include a second endovascular electrogram lead on the elongate body positioned distal to the endovascular electrogram lead wherein the processor is further configured to receive and process a signal from the second endovascular electrogram lead. In addition, the processor is further configured to compare the signal from the endovascular electrogram lead and the second endovascular electrogram lead. In one aspect, the signal from the endovascular electrogram lead includes a target electrogram signal and the second endovascular electrogram lead comprises a baseline electrogram signal. In one aspect, the target electrogram signal and the baseline electrogram signal are related to ECG, to EMG or to EEG, alone or in any combination.

The endovascular access and guidance system may also include an additional sensor for detecting a physiological parameter of the vasculature, the sensor positioned along the elongate body. The processor may also be configured to receive and process a signal from the additional sensor. The additional sensor for detecting a physiological parameter of the vasculature may be, for example, a pressure sensor or an optical sensor.

The processor may also be configured to receive and process a signal from the non-imaging ultrasound transducer comprising a signal from at least one of the group consisting of: a venous blood flow direction, a venous blood flow velocity, a venous blood flow signature pattern, a pressure signature pattern, A-mode information and a preferential non-random direction of flow and to receive and process a signal from the endovascular electrogram lead the signal comprising at least one of the group consisting of: an electrocardiogram signal, a P-wave pattern, a QRS-complex pattern, a T-wave pattern, an EEG signal and an EMG signal.

In still another aspect, the endovascular access and guidance system has a processor configured to store a signal received from the non-imaging ultrasound transducer and a signal received from the endovascular electrogram lead. The processor may also be configured to process a portion of the stored signal received from the non-imaging ultrasound transducer that corresponds to a signal received from the endovascular electrogram lead. The signal received from the endovascular electrogram lead comprised a P-wave.

According to one aspect of the invention, an endovascular device includes an elongate body with a proximal end and a distal end; a non-imaging ultrasound transducer on the elongate body; and an endovascular electrogram lead on the elongate body in a position that, when the endovascular device is in the vasculature, the endovascular electrogram lead is in contact with blood. In one aspect, the endovascular electrogram lead is positioned at the elongate body distal end. Additionally or alternatively, the electrical sensing segment of an endovascular electrogram lead is positioned: within 3 cm of the elongate body distal end; within 3 cm of the non-imaging ultrasound transducer; and/or proximal to the non-imaging ultrasound transducer.

In an alternative of the endovascular device, the device also includes a second endovascular electrogram lead on the elongate body in a position that, when the endovascular device is in the vasculature, the second endovascular electrogram lead is in contact with blood. Additionally or alternatively, the electrical sensing segment of the second endovascular electrogram lead is positioned about 5 cm from the endovascular electrogram lead or positioned about 5 cm from the elongate body distal end.

In other embodiments of the endovascular device, the electrical sensing segment of the second endovascular electrogram lead is positioned at a distance spaced apart from the endovascular electrogram lead so that the second endovascular electrogram lead detects a baseline electrogram signal when the endovascular electrogram lead is detecting a target electrogram signal; at a distance related to the length of the superior vena cava such that when the endovascular electrogram lead is in the superior vena cava the second endovascular electrogram lead is outside of the superior vena cava; such that when the electrical sensing segment of the endovascular electrogram lead is positioned to detect a targeted electrogram signal from the heart the electrical sensing segment of the second endovascular electrogram lead is positioned to detect a comparison baseline ECG signal; such that when the electrical sensing segment of the endovascular electrogram lead is positioned to detect a targeted electrogram signal from the brain the electrical sensing segment of the second endovascular electrogram lead is positioned to detect a comparison baseline EEG signal; and/or such that when the electrical sensing segment of the endovascular electrogram lead is positioned to detect a targeted electrogram signal from a muscle the electrical sensing segment of the second endovascular electrogram lead is positioned to detect a comparison baseline EMG signal.

In other aspects of the endovascular device, the endovascular electrogram lead is moveable from a stowed condition within the elongate body and a deployed condition outside of the elongate body. In one alternative, the stowed endovascular electrogram lead curves the distal end of the endovascular device. Additionally, when the endovascular electrogram lead is in the stowed condition the electrical sensing segment is positioned to detect an electrogram signal.

One embodiment of the endovascular device may also include a steering element connected to the endovascular lead for directing the proximal end of the elongate body and the steering element may also provide torque to the elongate body distal end.

One embodiment of the endovascular electrogram lead in use extends at least partially about the elongate body and may include and an atraumatic tip. In one aspect, the endovascular device has an endovascular electrogram lead that is formed from a shape memory alloy. Additionally or alternatively, the endovascular electrogram lead is adapted for use to move the ultrasound sensor away from a blood vessel wall.

In another alternative, the endovascular device includes a coated metal braided structure and a portion of the coating on the metal braided structure is removed and the exposed metal braided structure functions as an endovascular electrogram lead electrical sensing segment.

In another alternative, the endovascular device includes an atraumatic tip on the distal end of the endovascular device. In one aspect, the atraumatic tip comprises an ultrasound lens and the lens may, for example, be a divergent lens.

The endovascular device may also include an opening in the elongate body; and a lumen within the elongate body in communication with the opening and the elongate body proximal end.

The endovascular device may also include an additional sensor on the endovascular device for measuring a physiological parameter. The additional sensor is an optical sensor for use when the physiological parameter is related to an optical property detected within the vasculature. The additional sensor is a pressure sensor for use when the physiological parameter is related to a pressure measurement obtained within the vasculature. The additional sensor is an acoustic sensor for use when the physiological parameter is related to an acoustic signal detected within the vasculature.

The elongate flexible member may be configured as or to work in cooperation with an endovascular device such as, a catheter, a guide wire, or a stylet.

Moreover, the elongate flexible member may also be adapted to deliver a therapy to the patient and/or adapted to provide endovascular access for another device.

In one aspect, the method of positioning an endovascular device in the vasculature of a body is accomplished by advancing the endovascular device into the vasculature and then transmitting a non-imaging ultrasound signal into the vasculature using a non-imaging ultrasound transducer on the endovascular device. Next, there is the step of receiving a reflected ultrasound signal with the non-imaging ultrasound transducer and then detecting an endovascular electrogram signal with a sensor on the endovascular device. Then there is the step of processing the reflected ultrasound signal received by the non-imaging ultrasound transducer and the endovascular electrogram signal detected by the sensor. Finally, there is the step of positioning the endovascular device based on the processing step.

The method of positioning an endovascular device in the vasculature of a body may also include additional or modified steps according to the specific application or process being performed. Numerous additional alternative steps are possible and may be used in a number of combinations to achieve the guidance and positioning results described herein. Additional steps may include verifying that the length of the endovascular device inserted into the body is equivalent to the estimated device length prior to the procedure and/or inputting into the system the length of the endovascular device inserted in the body. Additionally, the step of detecting an endovascular electrogram signal with a sensor positioned on a patient may be added. The sensor may be on the patient or a second or additional sensor on an endovascular device. There may also be added the step of comparing the endovascular electrogram signal from the sensor on the device or patient to the endovascular electrogram signal from the second sensor on the device.

The processing methods and algorithms may also be modified or combined to identify important or unique signatures useful in guidance, localization or correlation. The method may include different or customized software or programming for processing ultrasound and/or electrogram signal information. The processing may include processing of reflected ultrasound signal to identify the caval-atrial junction or to determine the highest average velocity of a velocity profile. The processing may include processing of the endovascular electrogram signal to determine: peak to peak amplitude changes in an electrogram complex; peak to peak amplitude changes of an QRS complex in an electrocardiogram; peak to peak amplitude changes of an R-wave in an electrocardiogram and or peak to peak amplitude changes of an P-wave in an electrocardiogram and, additionally or alternatively, to use electrogram information as a trigger to acquire and/or process ultrasound information.

The processing methods and algorithms may also be modified or combined to identify important or unique signatures to determine the position of a guided endovascular device relative to anatomical structures or positions in the body. Examples of these methods include performing the processing step to determine the position of the endovascular device relative to: the caval-atrial junction, the sinoatrial node, the superior vena cava, the internal jugular vein, and the subclavian vein.

The method of positioning an endovascular device in the vasculature of a body may be further modified to include using the endovascular device to determine a location to secure a device within the vasculature of a body and then securing the endovascular device along with the device to the body to maintain the device in the location determined by the endovascular device. The method of positioning an endovascular device in the vasculature of a body may also include the steps of calculating a current position of the device and then comparing the calculated current position of the device to a location indicated by the processing step.

The steps of the method may be performed in any order or repeated in whole or in part to achieve the desired positioning or placement of the guided endovascular device. For example, the method of positioning an endovascular device in the vasculature of a body may include performing the processing step and the positioning step until the endovascular device is positioned within the right atrium relative to the coronary sinus. Alternatively, the method of positioning an endovascular device in the vasculature of a body may include performing the processing step and the positioning step until the endovascular device is positioned within the left atrium relative to a pulmonary vein. Alternatively, the method of positioning an endovascular device in the vasculature of a body may also include performing the processing step and the positioning step until the endovascular device is positioned within the aorta.

This aspect may be modified to include, for example, an additional step of displaying a result of the processing step. The processing step may also include information related to venous blood flow direction. The venous flow direction may also include a flow directed towards the sensor and a flow directed away from the sensor. Additionally or alternatively, the result of the processing step may also include one or more of information related to venous blood flow velocity, information related to venous blood flow signature pattern, information related to a pressure signature pattern, information related to ultrasound A-mode information; information related to a preferential non-random direction of flow within a reflected ultrasound signal, information related to electrical activity of the brain, information related to electrical activity of a muscle, information related to electrical activity of the heart, information related to the electrical activity of the sinoatrial node; and information about the electrical activity of the heart from an ECG.

In another aspect, the displaying step may also be modified to include a visual indication of the position of the device. The displaying step may also be modified to include a visual or color based indication of the position of the device alone or in combination with a sound based indication of the position of the device.

The method of positioning an endovascular device in the vasculature of a body may also be modified to include the step of collecting the reflected ultrasound signal in synchrony with an endovascular electrogram signal received by the sensor. Additional alternatives are possible such as where the endovascular electrogram comprises electrical activity from the heart, from the brain or from a muscle. The collection step may be timed to correspond to physiological actions or timings. For example, the collecting step is performed in synchrony during the PR interval or in synchrony with a portion of the P-wave.

Other portions of an EEG, ECG or EMG electrogram may also be used for timing of collecting, processing and/or storing information from device based or patient based sensors. In one aspect of the method of positioning an endovascular device in the vasculature of a body, the transmitting step, the receiving step and the processing step are performed only when a selected endovascular electrogram signal is detected. In one version of the method, the selected endovascular electrogram signal is a portion of an ECG wave. In another version of the method, the selected endovascular electrogram signal is a portion of an EEG wave. In still another version of the method, the selected endovascular electrogram signal is a portion of an EMG wave.

The method of positioning an endovascular device in the vasculature of a body may also include identifying a structure in the vasculature using non-imaging ultrasound information in the reflected ultrasound signal. In one aspect, the non-imaging ultrasound information comprises using A-mode ultrasound to identify the structure in the vasculature. In another aspect, the non-imaging ultrasound information includes using Doppler ultrasound information to identify a flow pattern in proximity to the structure.

An another aspect of the method of positioning an endovascular device in the vasculature of a body the processing step is performed only on a portion of the reflected ultrasound signals that correspond to a selected electrogram trigger signal. This method may be employed, for example, when the selected electrogram trigger signal is a portion of an ECG wave, a portion of an EEG wave or a portion of an EMG wave.

In still other methods of positioning an endovascular device in the vasculature of a body, the processing step may be modified to include processing the reflected ultrasound signal by comparing the flow energy directed away from the endovascular device to the flow energy directed towards the endovascular device. In one aspect, there is a step of selecting for comparison the flow energy related to blood flow within the range of 2 cm/sec to 25 cm/sec.

In still other alternatives, the method of positioning an endovascular device in the vasculature of a body includes a processing step that has a step of processing the reflected ultrasound signal to detect an indicia of pulsatile flow in the flow pattern. The indicia of pulsatile flow may be any of a number of different parameters. The indicia of pulsatile flow may be: a venous flow pattern; an arterial flow pattern or an atrial function of the heart.

The method of positioning an endovascular device in the vasculature of a body may also include modification to the processing step to include the step of processing the endovascular electrogram signal to compare the relative amplitude of a P-wave to the relative amplitude of another portion of an electrocardiogram. In one aspect, the another portion of an electrocardiogram includes a QRS complex. The processing step may also be modified to include processing the reflective ultrasound signal to determine a blood flow velocity profile and processing the detected endovascular electrogram signal to determine a shape of the intravascular electrocardiogram. The processing step may be further modified to include the step of correlating the blood flow velocity profile and the shape of the intravascular electrocardiogram to determine the location of the endovascular device within the vasculature.

In one aspect, there is an endovascular access and guidance system with one or more of the following components:

an elongate flexible member adapted and configured to access the vasculature of a patient; a sensor disposed at a distal end of the elongate flexible member and configured to provide in vivo non-image based ultrasound information of the vasculature and of the heart of the patient; a sensor disposed at a distal end of the elongate flexible member and configured to provide in vivo electrical signals (electrocardiograms) of the vasculature and of the heart of the patient; a processor configured to receive and process in vivo non-image based ultrasound information and electrocardiogram information of the vasculature and the heart of the patient provided by the sensors and to provide position information regarding the position of the distal end of the elongate flexible member within the vasculature and the heart of the patient; and/or an output device adapted to output the position information from the processor.

In one configuration, the processor used in the endovascular access and guidance system is configured or programmed to perform one or more of the following:

process in vivo non-image based ultrasound information of the vasculature system of the patient provided by the sensor to indicate in the output information the presence of structures and objects in the field of view; process in vivo non-image based ultrasound information and the electrocardiogram information of the vasculature system of the patient to indicate in the output information movement of the elongate flexible member in a desired direction within the vasculature of the patient; and process in vivo non-image based ultrasound information of the vasculature system of the patient based on a parameter selected from a group consisting of: a venous blood flow direction, a venous blood flow velocity, a venous blood flow signature pattern, a pressure signature pattern, A-mode information and a preferential non-random direction of flow, electrocardiogram signals, P-wave pattern, QRS-complex pattern, T-wave pattern.

The endovascular access and guidance system may include two or more additional sensors wherein the sensor and the two or more additional sensors are attached to the elongate flexible member to allow for measurements at different locations along the flexible member. The endovascular access and guidance system may also have a steering element for directing the device tip in response to feedback information derived from the acquired data. The endovascular access and guidance system may also have a torque control element for directing the device tip in response to feedback information derived from the acquired data.

In one aspect, there is a method for positioning an instrument in the vasculature system of a body by performing one or more or some of the steps of: accessing the vasculature of the body; positioning an instrument in the vasculature of the body; using the instrument to transmit an ultrasound signal into the venous system of the body; using the instrument to receive a reflected ultrasound signal from the vasculature indicating flow rates between 2 and 20 cm/s; using the instrument to record endovascular electrocardiograms indicating the proximity of the sinoatrial node of the heart; processing the reflected ultrasound signal and electrocardiogram to determine one or more parameters from a group consisting of: a venous blood flow direction, a venous blood flow velocity, a venous blood flow signature pattern, a pressure signature pattern, A-mode information and a preferential non-random direction of flow, electrocardiogram signals, P-wave pattern, QRS-complex pattern, T-wave pattern; and advancing the instrument within the vasculature using the one or more of the determined parameter or parameters within the vasculature.

The method for positioning an instrument in the vasculature of a body may also be modified or adjusted to include one or more of the steps of:

transmitting or receiving an A mode ultrasound signal into or from the vasculature of the body using the instrument that is being positioned; transmitting or receiving Doppler ultrasound signal into or from the vasculature of the body; transmitting or receiving a non-imaging target tracking ultrasound signal into or from the vasculature of the body; recording endovascular and intracardiac electrocardiograms from the vasculature of the body using the instrument; processing the reflected ultrasound signal and the endovascular electrocardiogram to determine a flow pattern determines a flow direction within the vasculature towards the instrument and further comprises processing the reflected ultrasound signal to determine a flow pattern determines a flow direction away from the instrument; processing the reflected ultrasound signal and the endovascular electrocardiogram to determine the presence of a signal indicating a specific blood flow pattern and a specific electrocardiogram pattern; processing the reflected ultrasound signal and the endovascular electrocardiogram and the endovascular electrocardiogram to determine the position of the instrument relative to the caval-atrial junction and to the sinoatrial node; processing the reflected ultrasound signal to determine the presence of a signal indicating a specific structure, including when the specific structure is a blood clot; processing the reflected ultrasound signal and the endovascular electrocardiogram and the endovascular electrocardiogram to determine the position of the instrument relative to the internal jugular vein; processing the reflected ultrasound signal and the endovascular electrocardiogram and the endovascular electrocardiogram to determine the position of the instrument relative to the subclavian vein; determining a location to secure a device within the vasculature of a body using information collected by the instrument; and securing the device to the body to maintain the device in the determined location; calculating the current position of the device using information from the instrument; and determining, based on the calculating step, if the device is in the location determined by the instrument by comparing the current calculated position of the device to the location determined by the instrument; processing the reflected ultrasound signal and the endovascular ECG to determine the position of the instrument within the right atrium relative to the coronary sinus; and/or processing the reflected ultrasound signal and the endovascular ECG to determine the position of the instrument within the left atrium relative to a pulmonary vein.

INCORPORATION BY REFERENCE

All patents, publications and patent applications mentioned in this specification are herein incorporated by reference in their entirety to the same extent as if each individual patent, publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 12 illustrates the use of intravascular ECG signals in case of a-fib patients.

FIG. 13 also illustrates the use of A-mode imaging for clot identification inside the blood stream or inside an endovascular member.

DETAILED DESCRIPTION OF THE INVENTION

Figure 1:
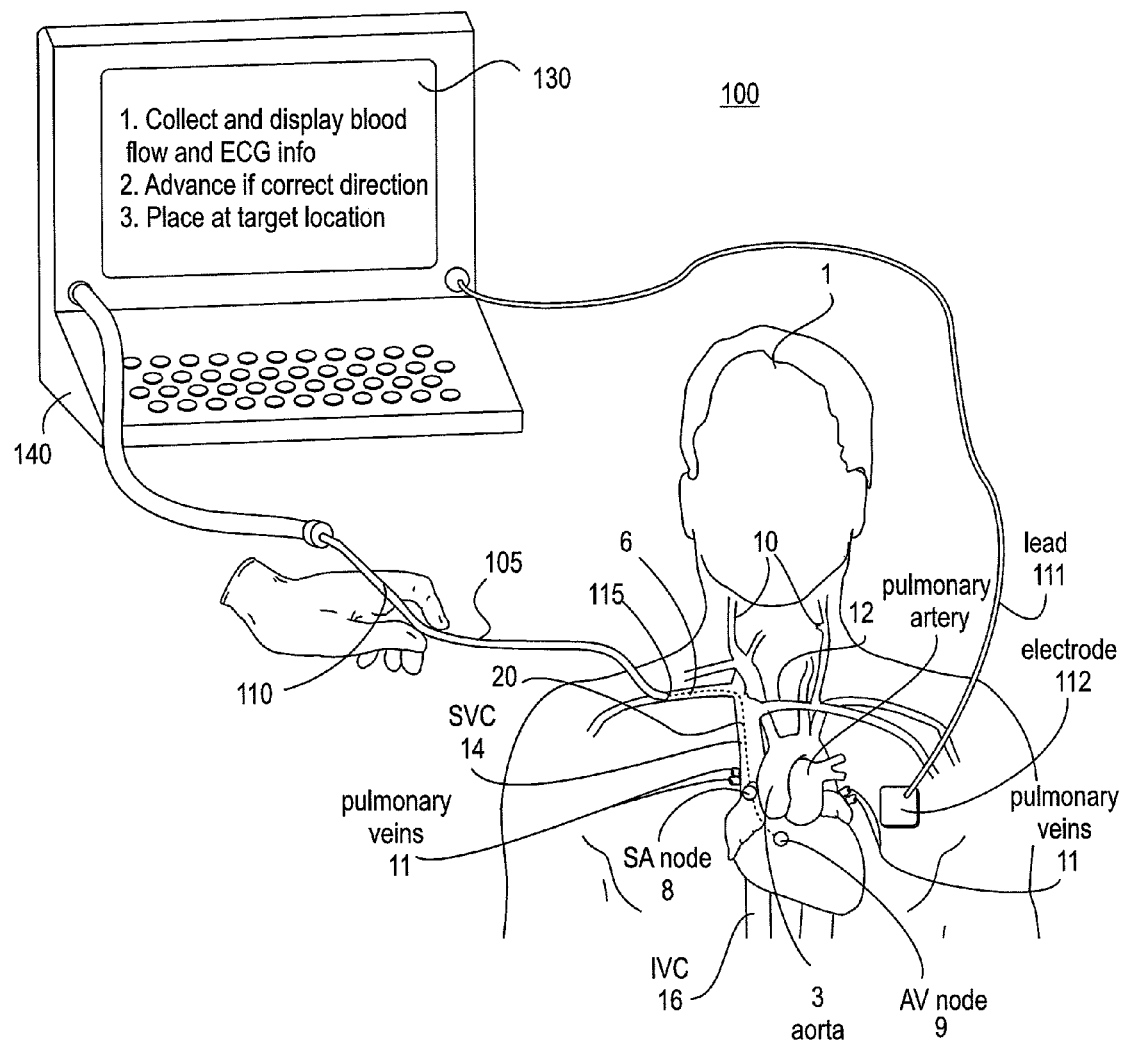
FIG. 1 illustrates an overview of the endovascular device guiding apparatus and method disclosed in the present invention.

Embodiments of the present invention provide guided vascular access devices, systems for processing signals from the guided vascular access devices and user interface for providing information to a user based on outputs from the processing system. FIG. 1 illustrates one embodiment of an exemplary endovascular access and guidance system 100. The system 100 includes an elongate body 105 with a proximal end 110 and a distal end 115. The elongate body 105 is any of a variety of endovascular devices adapted to insertion into and navigation through the vasculature of the patient 1. FIG. 1 illustrates the distal end 115 inserted into the basilic vein 6. The expected path of travel (dashed line 20) in this illustrative example is into the a portion of the heart 20 or within the superior vena cava 14 in proximity to the sinoatrial node (SA node) 8. The aorta 3, the pulmonary arteries, pulmonary veins 11, the jugular veins 10, the brachiocephalic vein 12, inferior vena cava 16 and atrioventricular node (AV node) 9 are also represented in this view.

Not shown in FIG. 1 but further described below, the elongate body 105 includes at least two sensors for measuring physiological parameters in the body. In some embodiments, one sensor is a non-imaging ultrasound transducer on the elongate body 105 configured to provide in vivo non-image based ultrasound information of the vasculature of the patient 1. In some embodiments, the other sensor is an endovascular electrogram lead on the elongate body 105 in a position that, when the elongate body 105 is in the vasculature, the endovascular electrogram lead electrical sensing segment provides an in vivo electrogram signal of the patient 1. FIG. 1 illustrates the use of a second electrogram sensor that is outside of the vasculature. The electrode 112 is positioned external to the vasculature of the patient 1. The electrode 112 detects electrogram information that is transmitted via lead 111 to the processor 140.

Alternatively, in place of the electrode 112 or in addition to the electrode 112 another electrogram sensor may be placed on the elongate body 105. More than one electrogram sensor may be provided on the elongate body. In this case, the processor 140 would also be configured to receive, process, compare and correlate the electrogram information from the additional electrogram sensor (or other sensors) provided by the elongate body 105. The electrogram leads or sensors on the elongate body 105 may also be placed relative to the elongate body 105 and to one another in order to obtain a target electrogram signal and a baseline electrogram signal in order to facilitate the position and location capabilities of the guidance system 100. The target and baseline electrogram information may be related to one or more of: (a) electrical activity of the heart including all or a portion of an electrocardiogram (ECG); (b) electrical activity of the brain including all or part of an electroencephalogram (EEG); and (c) electrical activity of a muscle or muscle group including all or part of an electromyogram (EMG) related to that muscle or muscle group. Additional details of the sensors and the various alternative configurations of the elongate body 105 are described below in at least FIGS. 2-5B.

The system 100 also includes a processor 140 configured to receive and process a signal from the non-imaging ultrasound transducer and a signal from the endovascular electrogram lead. The processor 140 includes conventional processing capabilities to receive and process ultrasound and electrogram signals as with conventional ultrasound and electrogram signals. The conventional processing capabilities include those conventional components needed to receive process and store the corresponding sensor data. If sensors on the elongate body are used to detect ECG activity, then appropriate electrocardiography components and processing capabilities is provided. The same is true for EEG signal processing, EMG signal processing, acoustic sensor processing, pressure sensor processing, optical sensor processing and the like.

However, unlike conventional ultrasound and electrogram systems, processor 140 includes programming and processing capabilities to process the signals from the sensors to identify and correlate flow and electrical patterns to aid in the guidance, positioning and confirmation of location of the elongate body 105 as described herein.

In one aspect, the processor 140 is adapted and configured using software, firmware or other programming capabilities to receive and process a signal from the non-imaging ultrasound transducer that contains at least one signal of the group consisting of: a venous blood flow direction, a venous blood flow velocity, a venous blood flow signature pattern, a pressure signature pattern, A-mode information and a preferential non-random direction of flow. Additionally, the processor 140 is further adapted and configured using software, firmware or other programming capabilities to receive and process a signal from the endovascular electrogram lead that contains at least one signal from the group consisting of: an electrocardiogram signal, a P-wave pattern, a QRS-complex pattern, a T-wave pattern, an EEG signal and an EMG signal.

In one aspect, the signal from one sensor is the trigger for acquisition or processing of a signal from another sensor. In this manner, the data from two different physiologic sensors may be correlated in time and to the trigger signal. Alternatively, rather than triggering acquisition data from the triggered sensor, all sensor data could be collected and/or stored and the trigger could instead result in the processing of only the subset of the data based on the trigger data. In either triggering scheme, the trigger sensor data and the triggered sensor data are processed together to yield the benefits described below. One example of triggering is the use of the P-wave detection from an electrogram sensor as the triggering signal for acquiring ultrasound data from an ultrasound sensor. As described below, the unique P-wave signal detected when an electrogram lead is positioned in the superior vena cava near the sino-atrial node 8 can be used to confirm the detection of the unique blood flow pattern that also occurs in this area of the vasculature. In this way, the existence of both unique physiological signals from two different physiological systems increases the accuracy of the guidance system embodiments described herein.

The system 100 also includes an output device 130 configured to display a result of information processed by the processor 140. The display device may, like the processor 140, include capabilities found in conventional display devices. The display device 140 of the invention differs from the conventional display in that the display is configured to display information related to the unique processing and results determined by processor 140. In one aspect, the output device 140 displays a result related to a position of the elongate body within the vasculature of the patient. In another aspect, a result of information processed by the processor includes an indication of a position or a movement of the elongate body 105 within the vasculature based on in vivo non-image based ultrasound information and in vivo electrogram information. The display 130 would be configured to display this information for a user to perceive in any suitable manner such as visually, with colors, with pictograms, with sounds or in other appropriate manners.

Other aspects of embodiments the invention relate to the use of intravascularly measured physiological parameters for locating, guiding, and placing catheters in the vasculature. In one aspect, embodiments of the present invention relate to an endovascular member assembly with built-in sensors for measuring of physiological parameters such as blood flow, velocity, pressure, or intravascular ECG. In a different aspect, embodiments of the invention relate to data processing algorithms that can identify and recognize different locations in the vasculature based on the pattern of physiological parameters measured at that location. In still another different aspect, embodiments of the present invention relate to data processing algorithms that can identify and recognize structures such as objects of interest in the vasculature or in endovascular members, e.g., blood clots based on the pattern of parameters measured, e.g, A-mode and blood flow velocity. In an additional aspect, embodiments of the present invention relate to an instrument that has a user interface which shows guiding and positioning information and presents the objects of interest, e.g., blood clots. For example, in this aspect the processor is further configured to process a signal from the non-image ultrasound transducer and to indicate in the output device information related to the presence of a structure in the field of view of the non-imaging ultrasound transducer.

In still another aspect, embodiments of the invention relate to the method of guiding and positioning an endovascular member within the vasculature by the user based on location information provided by the sensor-based endovascular member. Other various aspects of embodiments the invention relate to the use of intravascularly measured physiological parameters for locating, guiding, and placing catheters or stylets or guide wires for use as guides to particular locations within the vasculature that have been identified using the guided vascular access devices and systems described herein.

The present invention provides a new methods, devices and systems for intravascular guidance and placement of endovascular devices based on the recognition of patterns in the signals for different physiological parameters and correlation of those signal patterns. In one exemplary application, a catheter, such as a peripherally inserted central catheter (PICC) is inserted, advanced, positioned and monitoring within the vasculature based on the recognition of blood flow patterns, of the electrocardiogram signals and of their correlation at the locations of interest.

One benefit of the new apparatus and method introduced herein is that it increases the probability of correct placement of an endovascular device in a placement procedure performed at the bedside. Moreover, because of the accuracy and redundancy of the positioning methods described herein, it is believed that the use of the inventive methods, devices and systems will allow for endovascular device placement without the need for imaging guidance, in particular without X-ray imaging and/or imaging for confirmation of placement and lack of device migration. Another benefit of the new apparatus and method introduced herein is that it allows the detection of blood clots in the vasculature or in catheters such identifying the cause for a malfunctioning catheter, e.g., a central line.

Yet another benefit is related to the fact that the guided vascular access devices and the systems described herein may be inserted into the existing healthcare workflow for placing endovascular devices into the vasculature. More specifically, embodiments of the invention provide new sensor based endovascular devices, systems and methods for intravascular guidance and placement of, for example, sensor based catheters and/or guide wires. Then, the properly positioned sensor based endovascular device is used to then guide the deployment of other endovascular devices or facilitate the performance of other diagnostic or therapeutic procedures in the body such as, for example: (a) location of heart valves for replacement heart valve procedures; (b) identification of the renal veins for therapy in those veins or in the kidneys; (c) identification of renal veins and/or the inferior vena cava for IVC filter placement; (d) location of coronary sinus for placement of pacing leads or mitral valve modification devices; and (e) location of pulmonary veins for sensor placement and/or performance of therapy such as ablation treatment for atrial fibrillation; as well as a wide variety of other diagnostic or therapeutic procedures that would benefit from the placement of device or performance of therapy at specific locations in the vasculature identified by the sensor correlation techniques described herein.

In some embodiments, the systems and methods of embodiments of the inventive guidance system described herein are utilized to locate, guide and position catheters and/or guide wires equipped with sensors described herein within the vessels of the venous system. The embodiments described herein may also be utilized in the vessels of the arterial system as well. In one aspect, the guided vascular access devices described herein may be used for the guidance, positioning, and placement confirmation of intravascular catheters used in a wide number of clinical applications. Exemplary clinical applications that would benefit from embodiments of the invention include the placement of, for example, central venous access catheters (PICC), hemodialysis catheters and the placement of catheters, positioning of endovascular devices in the vasculature of the brain for treatment of stroke, placement of leads or other brain based therapy or therapy devices or treatment systems for percutaneous treatment of varicose veins. Moreover, particular muscles or muscle groups may be selected for EMG stimulation and/or sensor collection in support of one of more methods and devices described herein where the EMG signals are used to confirm and/or correlate a position in the vasculature. This aspect may be particularly helpful when identifying portions of the vasculature in the legs for localization of varicose veins, localization of the femoral veins or positioning of a vessel harvesting device within the great saphenous vein, for example.

While desiring not to be bound by theory, it is believed that certain locations in the vasculature can be identified by specific blood flow and electrogram patterns, electrogram signal patterns and correlation between these blood flow patterns at those locations. These patterns may be based on, for example, blood pressure, Doppler blood flow measurements, and intravascular electrocardiogram. Moreover, it is believed that the direction of travel for an sensor equipped endovascular device can be determined relative to the direction of blood flow by using the Doppler effect, relative changes in the intravascular electrogram signal and in the correlation between the blood flow and electrogram information.

For example, in the case of a Peripheral Inserted Central Catheter (PICC) line, by determining and real-time monitoring the direction of the catheter movement in the blood vessels using the sensors, techniques, data acquisition and processing described herein (for example blood flow and electrogram information), a user receives feedback on advancing a guided vascular access device to allow the PICC to advance along a desired path from an insertion vein into the vena cava and towards the sinoatrial node. The system may also recognize unintended entry into other veins because of the differences in flow patterns signals and electrogram signals or other signals received from the sensors. As such, the system may recognize unintended entry into the right atrium, inferior vena cava, jugular vein, the subclavian vein. Additionally, the system may detect when a sensor is against the vessel wall. By monitoring the data acquired from sensors positioned on the endovascular access device, the user can be notified when the device tip reaches the ideal placement in the lower third of the superior vena cava, at the caval-atrial junction and/or in the proximity of the sinoatrial node. The system recognizes these locations of the vena cava, and other vascular components, by analyzing sensor acquired data to identify unique flow patterns and electrogram signatures and to correlate these unique signatures in order to confirm placement, location and/or guidance.

The ultrasound technology described herein is a non-imaging ultrasound used in combination with intravascular electrograms, or other physiological parameter sensor data. The unique flow patterns may be discerned using non-imaging ultrasound and as such does not require all the elements that make ultrasound imaging possible, such as scanning with a moving transducer or working with phased arrays and beam forming, and the like. As such, embodiments of the present invention provide a vascular access and guidance system with a hand-held, simple, inexpensive user interface. Non-imaging ultrasound includes a number of various ultrasound techniques and processing configurations, by way of non-limiting example: A-beam ultrasound, Doppler ultrasound, continuous wave Doppler ultrasound, pulsed Doppler ultrasound, color Doppler ultrasound, power Doppler ultrasound, bi-directional Doppler ultrasound, and ultrasound techniques that provide for the determination of velocity profile based on correlation of blood flow and time.

One benefit of the methods, devices and systems described herein is the use of a "multi-vector" or "multi-parameter" approach. The multi-vector approach refers to the use of the blood flow information, the electrical activity information and the relationship between the two. The physiological information is analyzed in order to identify the location in the vasculature where the information was acquired. Because body functions are unique at certain corresponding unique locations in the vasculature, embodiments of the present invention can use measurements of the body functions and detect location in the body.

Figure 17:
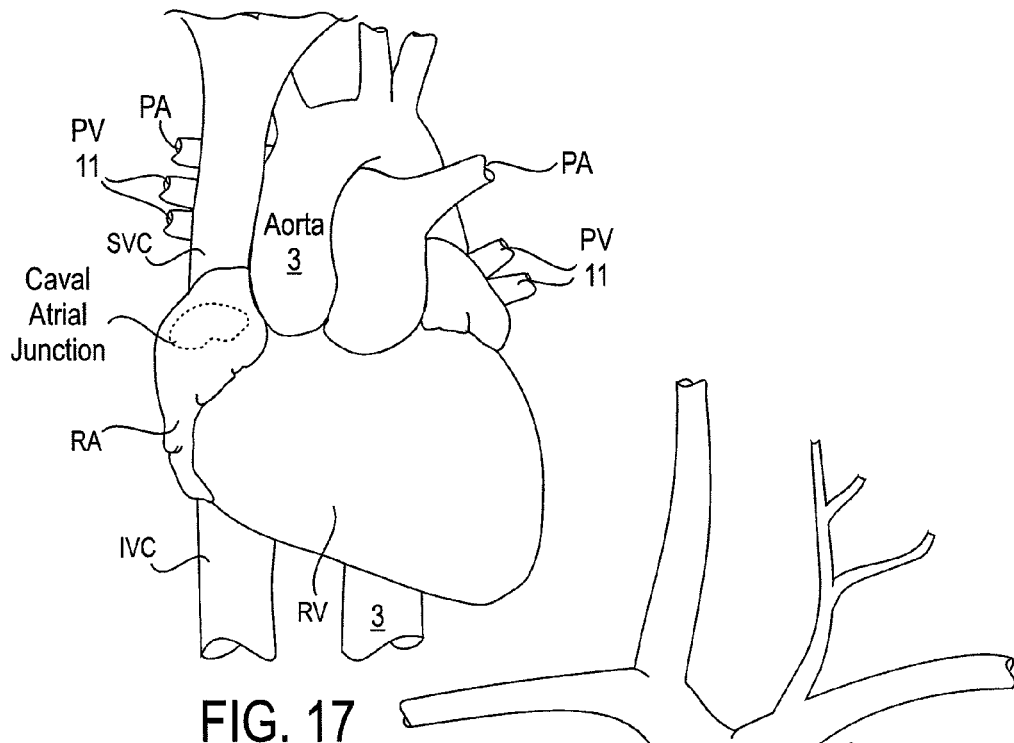
FIGS. 17 and 18 are various views of the heart and surrounding vasculature.
Figure 18:
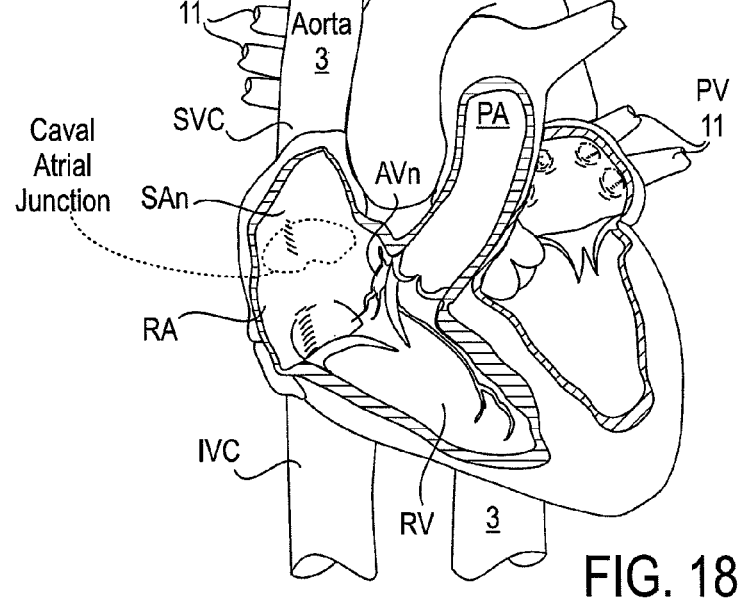

In particular, the present invention describes the use of the blood flow profile and of the intravascular ECG to detect the proximity of the sinoatrial node and of the caval-atrial junction. FIG. 17 illustrates the anatomical location of the caval-atrial junction at the confluence between the superior vena cava (SVC) and inferior vena cava (IVC just before entering the right atrium (RA). FIG. 18 illustrates the anatomical location of the sinoatrial node at the caval-atrial junction. The function of the vasculature and the function of the heart are unique at the caval-atrial junction both in terms of blood flow profile and of electrical activity of the heart.

For example, the system according to the present invention identifies the blood flow profile characteristic of the caval-atrial junction and ECG waveform patterns characteristic of the proximity of the sinoatrial node and, when both these patterns are present, indicates to the user that the desired target location has been reached. One benefit of this approach is that the blood flow and the electrical activity are independent physiological parameters and thus by considering them together, the accuracy of the location information is significantly improved. In addition the intravascular electrogram signal can be used for selective (gated) acquisition and processing of the blood flow information, depending upon the specific characteristics of the electorgram signal being utilized. For example when the electrogram signal is produced by the heart from the gating acquisition may be based on one or more integrals of the heart cycle. This selective approach also increases the accuracy of determining blood flow patterns corresponding to locations in the vasculature.

Endovascular Member with Sensors for Guidance

Figure 2:
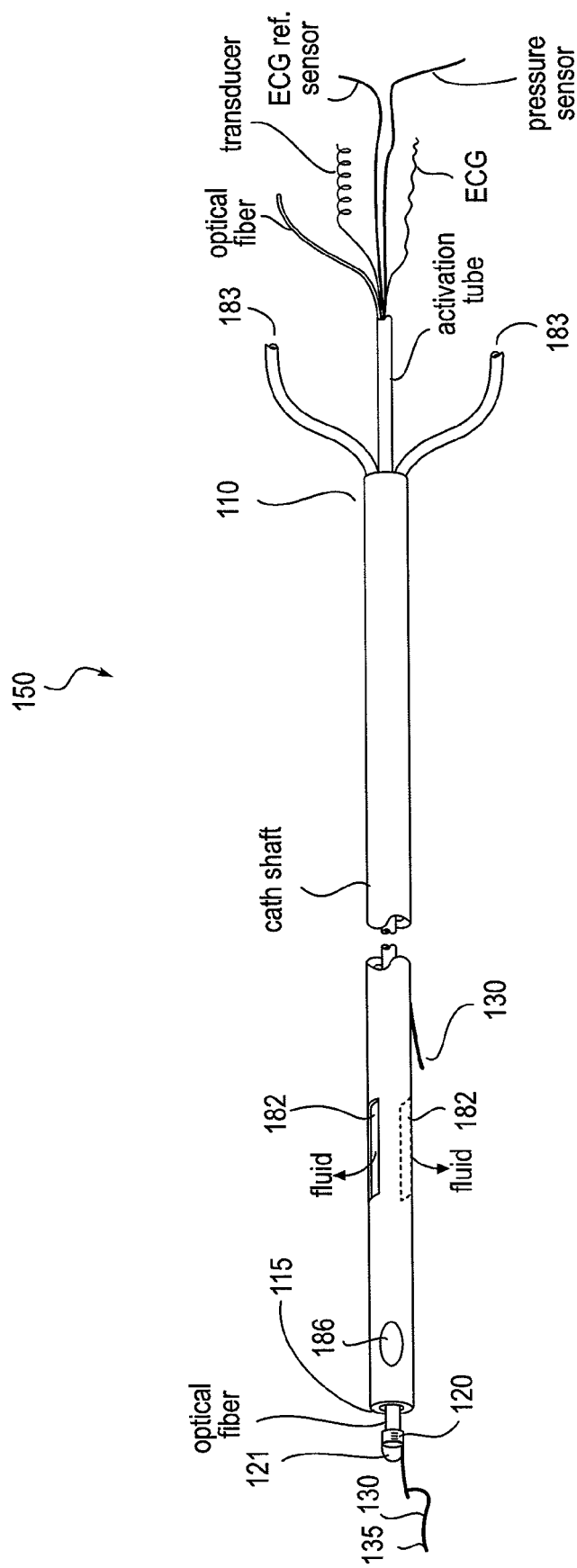
FIG. 2 illustrates an endovascular device with multiple sensors.

FIG. 2 illustrates an endovascular device 150 having an elongate body 105 with a proximal end 110 and a distal end 115. There is a non-imaging ultrasound transducer 120 on the elongate body 105. There is an atraumatic tip 121 on the endovascular device 150. The atraumatic tip 121 may also include an ultrasound lens. The ultrasound lens may be used to shape the ultrasound signal produced by the ultrasound transducer 120. In one aspect the ultrasound lens is a divergent lens.

The endovascular device 150 also has an opening 182 in the elongate body 105 and a lumen within the elongate body 105 in communication with the opening 182 and the elongate body proximal end 110. As illustrated, there may be one or more openings 182 in communication with one or more lumens or tubes 183. Also shown on the proximal end 110 are the various connections to the sensors and lumens in the endovascular device 150. These connections are conventional and may take any suitable form to connect the endovascular device to the other guidance system 100 components such as the processor, display or fluid delivery device. As such, by using additional lumens or other access features, the elongate body 105 or endovascular device 150 is adapted to deliver a therapy to the patient such as by delivering drugs, therapeutic or diagnostic agents through the openings 182 or between the inner and outer tubes. In yet another alternative configuration, the elongate body 105 or the endovascular device 150 is adapted to provide endovascular access for another device.

The endovascular device 150 also illustrates how other additional and optional sensors may be provided. Embodiments of the endovascular device 150 may contain any of a number of different sensors. The sensor is selected based on the physiological parameter to be measured and used in the guidance, positioning and correlation methods described herein. By way of non-limiting example, the device may include an ultrasound sensor, a conductive wire, a pressure sensor, a temperature sensor, a sensor for detecting or measuring electrical potential and voltages and other sensors suited to collecting physiological information and providing information to the processor 140 for processing in an algorithm or for other suitable form of analysis based on the techniques described herein. The sensor-based endovascular device 150 can be used independently to deliver a payload into the vasculature, e.g., a drug or to draw blood or it can be inserted into the one of the lumens of another endovascular device, e.g., a catheter. Then the entire assembly can be inserted into the patient's body, e.g., for a PICC placement procedure, or through a catheter 90 (see FIG. 4C).

Additionally or alternatively, the endovascular device 150 can be configured as any type of catheter, stylet, guidewire, an introducer, a combination thereof or any other type of device which allows for vascular access. The endovascular device and the corresponding connection from the sensors to the proximal end can either be fixed in the endovascular device, or pre-inserted and removable after procedure, or reinsertable for location verification post placement. In one embodiment the endovascular device integrates a single lead electrode for electrical activity monitoring. In a different embodiment, the endovascular device may integrate several electrodes (leads), for example one at the very distal tip of the endovascular member and one more proximal such that the distal electrode can detect the electrical activity of the heart while the more proximal electrode can serve as a reference for measuring since the more proximal electrode is closer to the patient's skin and further away from the heart. In addition to providing electrical mapping, the lead/electrode can be used as a steering element to steer and position the endovascular device as illustrated in FIGS. 3A, 3B, 4A and 4B.

According to the embodiments of the present invention physiological information is acquired by sensors and transmitted to a processor. The processor uses algorithms which analyze and process the sensor data to provide information on the location of the sensor core assembly and of the corresponding endovascular device in the patient's vasculature. Since high degree of accuracy is desired, different types of physiological information, ideally independent from each other, such as blood flow information and electrogram information are used to accurately characterize the direction of movement and location. In one aspect of the present invention, the described clinical need is met by gathering physiological information regarding blood flow using ultrasound and regarding the electrical activity of the heart by acquiring endovascular electrical signals.

By way of example, the endovascular device embodiments of FIGS. 3A, 3B, 5A, 5B, consists of an elongate body 105 that may be configured as any of a catheter, a stylet, or a guidewire that is configured for endovascular access. Moreover, the catheter, stylet or guidewire may be of the one part or two part construction described herein.

The endovascular device 150 may be configured as a single structure (FIGS. 3A, 3B, 4A, 4B, 5A and 5B, also be a removable device or sensor core assembly may consist of a non-imaging ultrasound transducer mounted at the end of a piece of tubing. The tubing can be single or multi-lumen and can be made of any of a variety of polymeric, or elastomeric materials. The lumens may be used to support the sensors on the tubing or may be used for delivery of therapeutic or diagnostic agents. One or more physiological parameter monitoring sensors may be positioned on the tubing as described herein. The endovascular device may have a two part construction as shown in the illustrative embodiment of FIG. 2 where the ultrasound transducer is on a tube (an inner tube) within another tube (an outer tube).

In the illustrative embodiment of FIG. 2, the inner tube carries the ultrasound transducer. The outer tube, possibly a multi-lumen tube, has a lumen for the inner tube. Additionally, lumens 183 are provided to correspond to the openings 182. The outer tube also supports the additional sensors (one sensor 186 is shown). The wiring or other connections for the additional sensors 186 or electrogram lead may also be provided with their own lumen or lumens. The proximal end 110 and the various leads and lumens and other connections may be placed into a single connector used to attach the endovascular device 150 to the other components of the system 100.

Whether the endovascular device 150 is a single tube or a multiple tube construction, the device include an additional sensor 186 on the endovascular device for measuring a physiological parameter. In one aspect, the additional sensor is an optical sensor and the physiological parameter is related to an optical property detected within the vasculature. In another aspect, the additional sensor is a pressure sensor and the physiological parameter is related to a pressure measurement obtained within the vasculature. In another aspect, the additional sensor is an acoustic sensor and the physiological parameter is related to an acoustic signal detected within the vasculature.

There is an endovascular electrogram lead 130 on the elongate body 105 in a position that, when the endovascular device 150 is in the vasculature, the endovascular electrogram lead 130 is in contact with blood. There are two endovascular leads 130 in the illustrated embodiment of FIG. 2. As shown, there is an endovascular electrogram lead 130 positioned at the elongate body distal end 115.

As used herein, an electrogram lead 130 contains at least one electrical sensing segment 135. The electrical sensing segment 135 is that portion of the electrogram lead 130 that is used for detecting or sensing the electrical activity being measured. The electrical sensing segment 135 could be a portion of the lead 130 that is not insulated, it could be a separate structure, like an electrode, that is joined to the lead 130 or it could be a structure within the endovascular device (see FIG. 5B). In one aspect, the electrical sensing segment of an endovascular electrogram lead is positioned within 3 cm of the elongate body distal end 115. In another aspect, the electrical sensing segment 135 of an endovascular electrogram lead 130 is positioned within 3 cm of the non-imaging ultrasound transducer 120. As shown in FIG. 2, this aspect relates to the lead 130 that extends from the distal end or to the spacing of proximally positioned endovascular lead 130. Additionally or alternatively, the electrical sensing segment 135 of an endovascular electrogram lead 130 is positioned proximal to the non-imaging ultrasound transducer 120.

Figure 3A:
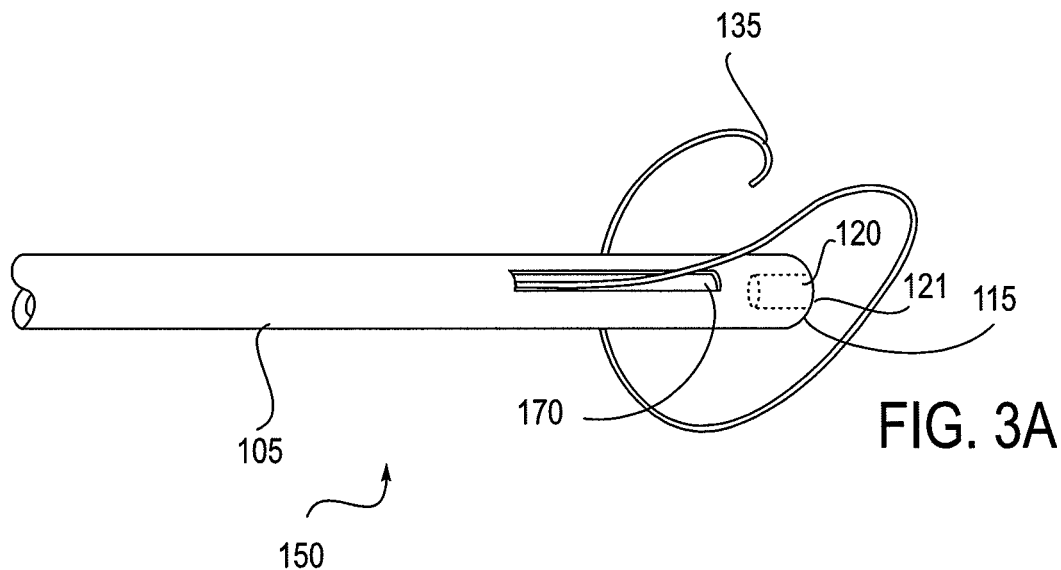
FIG. 3A-3B illustrates an intravascular ECG electrode which can be used for steering and moving the endovascular member away from the vessel wall.

FIG. 2 also illustrates an endovascular device with a second endovascular electrogram lead 135 on the elongate body 105. The second endovascular lead is shown in a position that, when the endovascular device 150 is in the vasculature, the second endovascular electrogram lead 130 is in contact with blood. Endovascular leads 130 (and/or the corresponding electrical sensing segment or segments 135) may extend from the elongate body 105 as shown in FIGS. 2 and 3A or may be integral to or within the elongate body as shown in FIGS. 3B, 4A, 4B 5A, and 5B. In one embodiment, the electrical sensing segment 135 of the second endovascular electrogram lead 130 (the proximal electrogram lead 130 in FIGS. 2 and 4B) is positioned about 5 cm from the other endovascular electrogram lead 130. Alternatively, electrical sensing segment 135 of the second endovascular electrogram lead 130 is positioned about 5 cm from the elongate body distal end 115.

The use of two electrogram leads can be used to enhance the measurement accuracy of the electrical signals being used in the guidance system. In this regard, the electrical sensing segment of the second endovascular electrogram lead is positioned at a distance spaced apart from the endovascular electrogram lead so that the second endovascular electrogram lead detects a baseline electrogram signal when the endovascular electrogram lead is detecting a target electrogram signal. In this way, the system may rely completely on electrical signals completely within the vasculature to obtain a baseline measurement thereby eliminating the need for an external sensor as shown in FIG. 1. In this regard, the electrical sensing segment of the second endovascular electrogram lead is positioned such that when the electrical sensing segment of the endovascular electrogram lead is positioned to detect a targeted electrogram signal from the heart the electrical sensing segment of the second endovascular electrogram lead is positioned to detect a comparison baseline ECG signal. Alternatively, the electrical sensing segment of the second endovascular electrogram lead is positioned such that when the electrical sensing segment of the endovascular electrogram lead is positioned to detect a targeted electrogram signal from the brain the electrical sensing segment of the second endovascular electrogram lead is positioned to detect a comparison baseline EEG signal. In another alternative, electrical sensing segment of the second endovascular electrogram lead is positioned such that when the electrical sensing segment of the endovascular electrogram lead is positioned to detect a targeted electrogram signal from a muscle the electrical sensing segment of the second endovascular electrogram lead is positioned to detect a comparison baseline EMG signal.

There are also embodiments where the spacing between the electrogram leads is related to the target anatomy or anatomical structures. In one example, the electrical sensing segment of the second endovascular electrogram lead is positioned at a distance related to the length of the superior vena cava such that when the endovascular electrogram lead is in the superior vena cava the second endovascular electrogram lead is outside of the superior vena cava. Similarly, following the EEG and EMG examples above, one lead would be near a target region of the brain or a muscle and the second would be positioned so that it would detect baseline electrical levels.

The conductive element for an electrogram lead can be made up of any suitable biocompatible conductive material such as stainless steel, a saline column or SMAs (smart memory alloys or shape memory alloys), e.g., nitinol. The endovascular devices and sensors described herein are suited and configured for use in the vasculature and are thus sized and have appropriate finishes or coatings to facilitate endovascular use. Typical diameters of the conductive element are between 0.005" and 0.010". Typical lengths of the conductive element or the endovascular device are between 1 and 8 feet.

Figure 3B:
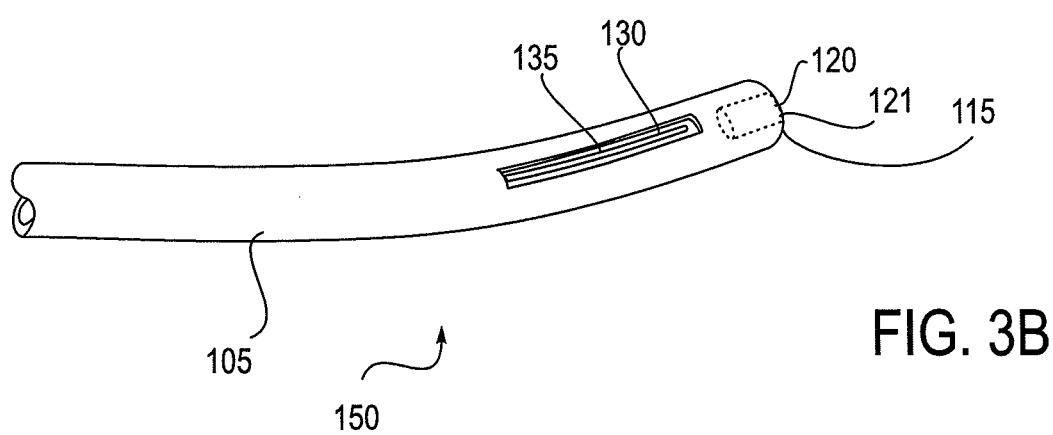

Moreover, in some aspects, the conductive element is sized and configured to perform multiple functions or functions in addition to signal detection and transmission. For example, the conductive element or electrogram lead may be used for steering, tip positioning, and others. FIGS. 3A and 3B illustrate an embodiment of an endovascular device 150 with an elongate body with a proximal end and a distal end. There is a non-imaging ultrasound transducer on the elongate body. There is an endovascular electrogram lead on the elongate body in a position that, when the endovascular device is in the vasculature, the endovascular electrogram lead is in contact with blood. The electrical sensing segment 135 is positioned to detect an electrogram signal. The electrical sensing segment 135 is positioned in the window 170 and can access blood. The window 170 is an opening into a lumen within the elongate body that forms a sliding seal about the electrogram lead 130. In this way, blood in contact with the window and the lead is prevented from flowing down the interior of the elongate body.

As best seen in FIGS. 3A and 3B, the endovascular electrogram lead 130 is moveable from a stowed condition within the elongate body (FIG. 3B) and a deployed condition outside of the elongate body (FIG. 3A). As best seen in FIG. 3A, the electrogram lead or conductive element can be deployed through a side opening or window 170 in the sidewall of the elongate body 105. In one embodiment, the window 170 is positioned at or near the distal end of an endovascular member. As shown in FIG. 3A, the electrogram lead 135 also serves the purpose of being able to distance the tip 115 or the ultrasound sensor 121 of the endovascular member away from the inner wall of the blood vessel. In this way, the endovascular electrogram lead is adapted for use to move the ultrasound sensor away from a blood vessel wall.

The deployed shape of the electrogram lead 135 shown in FIG. 3A may include shapes that curve completely or partially about the elongate body 105 and may be positioned proximal to the distal end, span the distal end or be positioned distal to the distal end. In one aspect the electrogram lead 135 is formed from a shape memory metal or material that is appropriately pre-set into the desired deployed shape. In one embodiment, the endovascular lead 130 is made of nitinol. The endovascular lead 130 may also include an atraumatic tip 139. The atraumatic tip 139 may be formed from the electrogram lead (a curved end, shaped end or rounded end) or may be a separate structure attached to the distal end to provide the atraumatic capability.

The endovascular electrogram 130 may be used to perform a number of additional and optional functions. As shown in FIG. 3B, when the endovascular electrogram lead is in the stowed condition, the lead curves the distal end 115. In this configuration, a steering element (such as those shown in FIGS. 4A and 4B) may be used to turn, twist or apply torque to the elongate body using the endovascular lead 130. In this way, the endovascular electrogram lead 130 may also be used for steering, placement or other guidance requirements of the user.

Figure 4A:
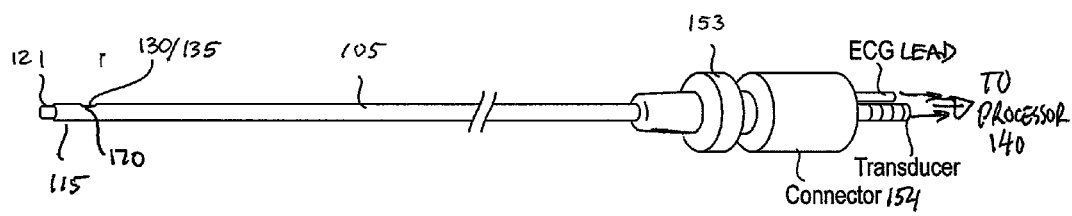
FIG. 4A-4C illustrates the concept of removable sensor core, whereby a stylet with integrated sensors can be inserted into and removed from an endovascular device like a catheter at any time.
Figure 4B:
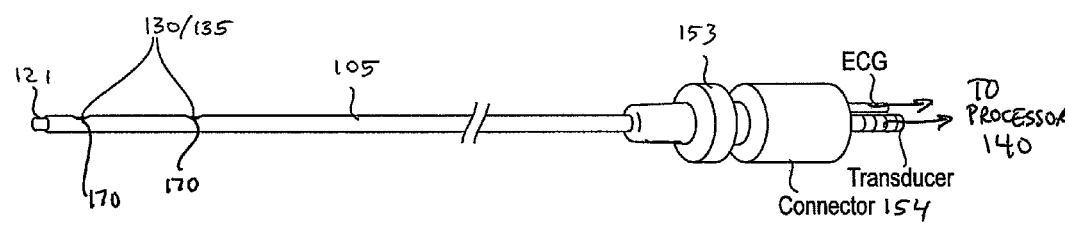

FIGS. 4A and 4B illustrate alternative exemplary embodiments of an endovascular device referred to as a sensor core assembly. The sensor core assembly derives its name from the compact size that allows it to be inserted into or ride along with in a lumen on or in another endovascular device. In this way, the functionality and advantages of the systems and methods described herein may be applied to a wide variety of devices positioned within or used within the vasculature. As such, the sensor core assembly can be pre-inserted (if used for guidance and initial placement) or later inserted (if used for position confirmation) into one of the lumens (inside or alongside) of another endovascular device, e.g. in into a PICC catheter.

The endovascular devices illustrated in FIGS. 4A and 4B also illustrate a steering element 153 on the proximal end. The steering element may be used to rotate one or both of the elongate body, a steering element in the elongate body or an electrogram lead 130 configured for concurrent use as a steering element. In use, the user would grasp the steering element 153 and manipulate as needed to produce the desired movement of the elongate body, the distal tip or the endovascular device. The steering mechanism 153 and the endovascular lead 130 may also be sized and configured that the lead, turned by the steering mechanism may apply torque or impart rotation to the elongate body or otherwise facilitate manipulation, steering or control of the endovascular device.

The embodiments illustrated in FIGS. 4A and 4B illustrate a connector or hub 154 on the proximal end that provides an appropriate and consolidated connection point for the sensors and other components of the endovascular device to the guidance system 100. The connector 154 and steering device 153 may be adapted and configured to allow relative movement between them so that the steering element 153 may be used without interrupting the connectivity provided by the connector 154.

Figure 4C:
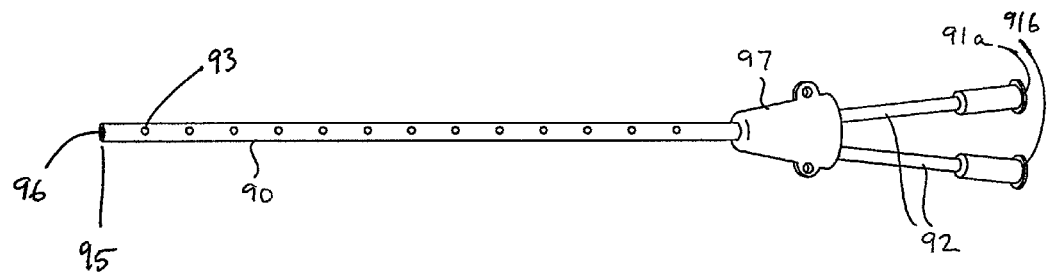

FIG. 4C is a conventional catheter 90 with a body, a distal end 95, a catheter hub 97 on the proximal end. A lumen 96 extends from the distal end, though the body and hub into communication with the tubes 92 and fittings 91a, 91b. The endovascular device 150 (FIGS. 4A and 4B) may be inserted directly into the patient vasculature and guided as described herein to a target site. Thereafter, the catheter 90 (or other device for placement) is run over the device 150 until in the desired position. Alternatively, the endovascular device 150 or sensor core assembly can be inserted in the lumen of an endovascular device (lumen 96 of catheter 90) which is then inserted into the patient's body and guided based on sensor inputs from the endovascular device 150.

In another aspect, the elongate body 105 is itself conductive using a metal wire or has integrated a conductive element such that it can detect electrical activity of the body and transmit resulting electrical signals to the proximal end of the member. The proximal end of the conductive element can be attached to a system for signal processing and graphical user interface. The attachments for the various sensors and components of the endovascular device 150 may be wired or wireless connections may be used.

Figure 5A:
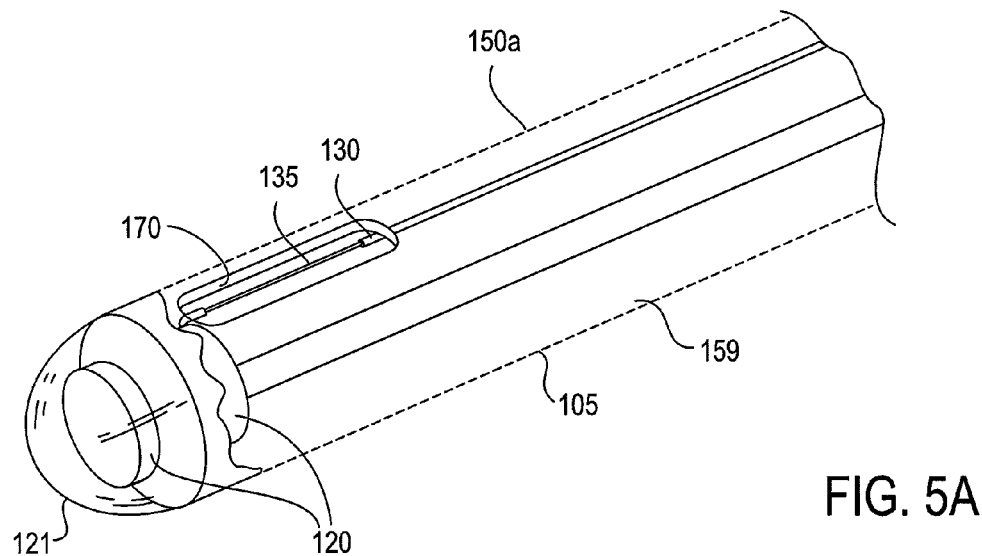
FIG. 5A-5B illustrates an embodiment integrated sensors in an endovascular device with braided shaft and atraumatic tip.
Figure 5B:
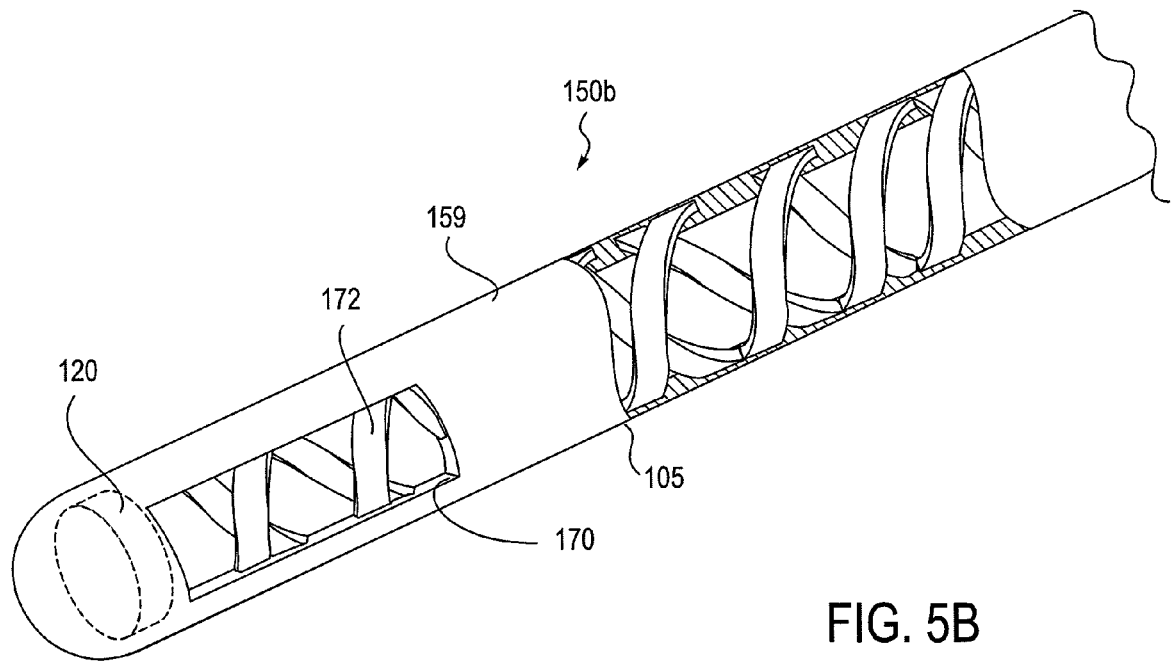

FIG. 5B is illustrates an endovascular device 150b with an elongate body 105 with a proximal end and a distal end. There is a non-imaging ultrasound transducer on the elongate body 120 and an endovascular electrogram lead on the elongate body in a position that, when the endovascular device is in the vasculature, the endovascular electrogram lead is in contact with blood. In this embodiment, the elongate body 105 comprises a coated metal braided structure 172 as best seen in the cut away portion of FIG. 5B. There is a coating 159 (typically an insulating coating may of a biocompatible polymer) over the metallic or conductive braided structure 172. A portion of the coating 159 on the metal braided structure 172 is removed (providing a window 170). The exposed metal braided structure (i.e., that portion exposed in window 170) functions as an endovascular electrogram lead electrical sensing segment 135. The remained of the braid 172 functions as the lead to transmit the signals detected by the exposed section back to the processor or other components of the guidance system 100.

Alternatively, as shown in FIG. 5B, the tube may be metallic or metal braid encapsulated by polymeric material. Additionally or alternatively, a polymeric material like PTFE or polyimide and a polymeric compound, e.g., polyimide and graphite or glass fiber can be used. A separate structure such as a spring, a wire or a mesh wire, made with stainless steel or nitinol for example, may also be inserted into or formed within the inner lumen of the sensor core tube to provide additional column strength and resistance to kinking or extreme bending to the sensor core tube. In addition, the separate wire can also be used for conducting electrical signals generated by the patient. FIGS. 5A and 5B demonstrate examples of these designs.

In the embodiments illustrated in FIGS. 5A and 5B, the sensor core assembly may contain a polymeric tube 159. The outer diameter of the tube may be from 0.010" to 0.030", the inner diameter from 0.008" to 0.028". The polymeric tube may be coated, for example with PTFE. The transducer, which can be 0.010" to 0.030" in diameter is fixed at the distal end of the sensor core assembly with Doppler-transparent adhesive or epoxy which can also be used as a lens or a plurality of microlenses to optimize the ultrasound beam profile.

At the distal end close to the transducer, there may be one or multiple windows 170 or a skived openings of 1 to 5 mm in length and width each that provides the ability for an electrogram element, e.g. the separate wire, to be in direct contact with biological fluid, blood, or tissue. The separate wire or electrogram lead can be made with any conductive material, e.g., nitinol, stainless steel, and is suitably connected to transmit detected electrical signals to the proximal end of the sensor core assembly and to components of guidance system 100. The separate wire may consist of one continuous conductive element or several conductive elements that are connected together.

In the embodiment in FIG. 5B the conductive element 130/135 is provided by a braid which is used to reinforce the shaft of the endovascular device. The braid can be made of any conductive material, e.g., stainless steel or nitinol, and can have any kind of geometries and number of wires. The braid is exposed at the distal end of the endovascular device to allow contact with blood and therefore be capable of detecting electrical activity. In some embodiments the braid servers as a reinforcement layer and therefore is electrically isolated from both the inner and the outer sides. In another embodiment, the tubing used for sensor core assembly can be made with a sleeve which has a mesh in a braid or coil form encapsulated by polymeric material. The sleeve may or may not have a polymeric material only stem at its ends. The mesh can be made with any conductive material, such as Nitinol or stainless steel, and needs to be able to transmit electric signal from the distal end to the proximal end of the sensor core assembly. The mesh may consist of one or multiple types of conductive elements and can be made with one or multiple conductive or non-conductive materials. The mesh may also consist of one or multiple types of continuous conductive element or several conductive elements that are connected to each other. By removing some of the polymeric material and exposing the conductive mesh to biological fluid, blood or tissue, endovascular electrogram signal can be transmitted through the mesh and the system can receive and interpret the signals. A separate polymeric sleeve or other isolating material can be used to isolate the wire attached to the Doppler sensor (coaxial or twisted pair wire or grounded twisted pair wire or any other type of conductive element) from contact with biological fluid, blood or tissue. A Doppler-transparent atraumatic tip can also be added to the distal end of the sensor core assembly. The Doppler-transparent atraumatic tip can also be used as a beam-shaping element for the ultrasound beam.

Endovascular Access and Guidance System
System Architecture

Figure 6:
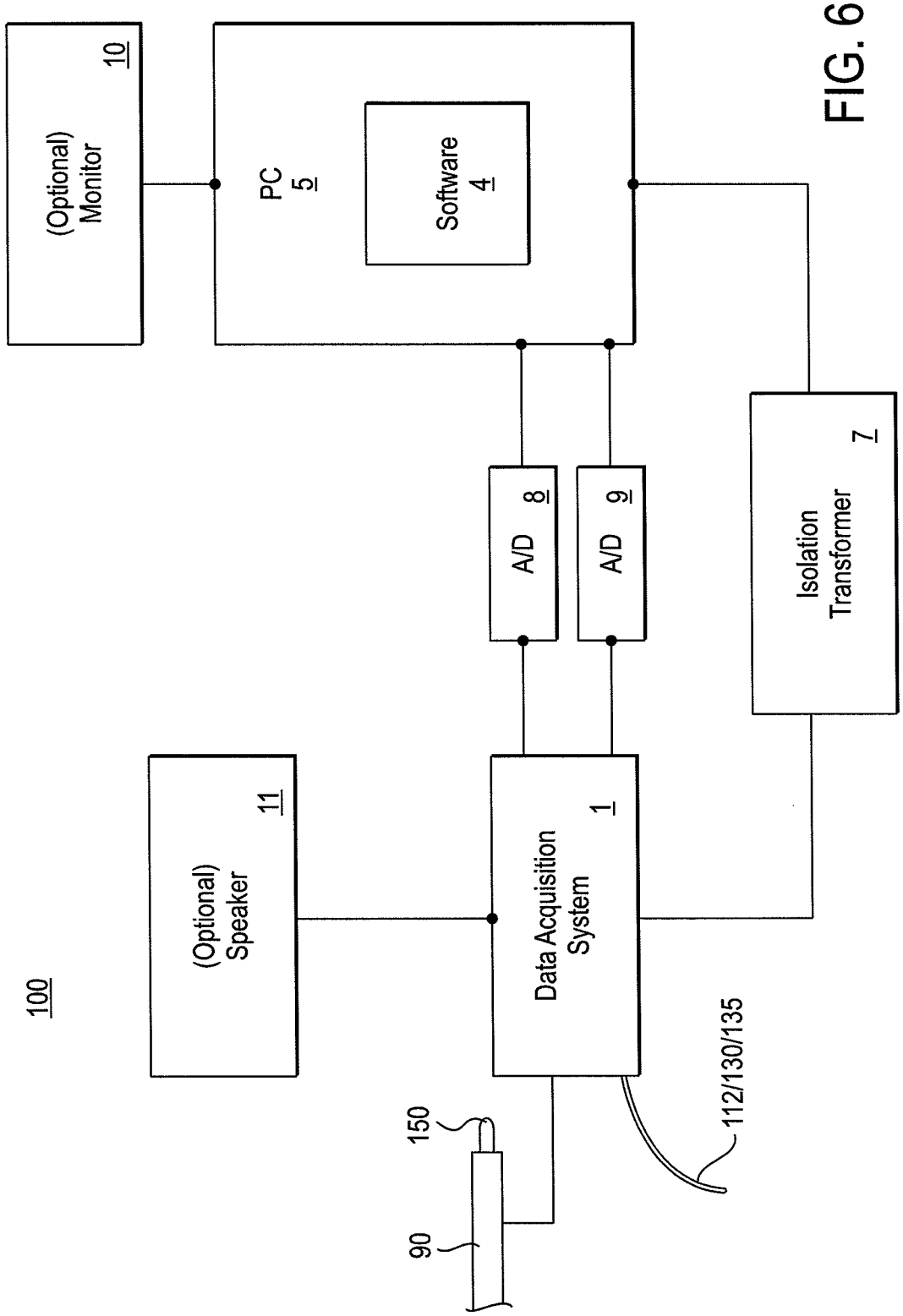
FIG. 6 illustrates another embodiment of integrated sensors in an endovascular device with stylet-like reinforcement that can be used as an ECG electrode.

FIG. 6 illustrates a system 100 that can be used to guide catheter placement using non-imaging ultrasound based blood flow information and electrical activity of the body. In one particular example, the system 100 is used to place an endovascular device 150 in the superior vena cava 14 using blood flow and ECG patterns and relative to the sinoatrial node 8 using intravascular ECG. An exemplary display 140 and/or user interface is shown in FIGS. 7, 8, 9, 13, 14A and 14D and is described below.

Returning to FIG. 6, the system 100 integrates a data acquisition system, two DAQ cards, an isolation transformer and a computing platform, e.g., a PC which has software loaded to process the signals and display information on a screen. The data acquisition system and the PC are powered from a common Isolation Transformer or other suitable power supply. The data acquisition system (1) is capable of acquiring ultrasound signals and electrical signals generated by the body activity, such as electrogram (ECG, EEG and/or EMG) including intravascular and intracardiac electrocardiogram signals. A sensor-based endovascular device 150 as described herein can be connected to the data acquisition system (1). An additional ECG lead 112 can be attached to the patient's skin (see FIG. 1) or provided by lead 130/135 for collecting a reference signal. The optional speaker (11) is used to optionally convert Doppler frequencies, i.e., blood velocities into audible signals or to otherwise provide signals or instructions to inform a user of the position of the device 150. One analog-to-digital converter (8) is used to digitize ultrasound signal information and transfer it to the processor 140 or other suitable computing platform for processing. A second analog-to-digital converter (9) is used to digitize electrogram signals coming from the electrogram lead on the endovascular device and from the reference electrode (either outside or inside the vasculature). Other or additional A/D converters may be provided based on the sensors used in the device 150.

The computing platform (4) can be a generic one like a personal computer or a dedicated one containing digital signal processors (DSP). The computing platform serves two purposes. It provides the processing capabilities of the processor 140 that allows data processing algorithms (5) to run. The various data processing algorithms employed by the various methods of embodiments of the current invention are described in greater detail below. The other purpose of the computing platform is to provide "back-end" functionality to the system 100 including graphical user interface, data storage, archiving and retrieval, and interfaces to other systems, e.g., printers, optional monitors (10), loudspeakers, networks, etc. Such interfaces can be connected in a wired or wireless configuration. Those of ordinary skill will appreciate that the conventional components, their configurations, their interoperability and their functionality may be modified to provide the signal processing and data capabilities of the guidance system 100.

Figure 19:
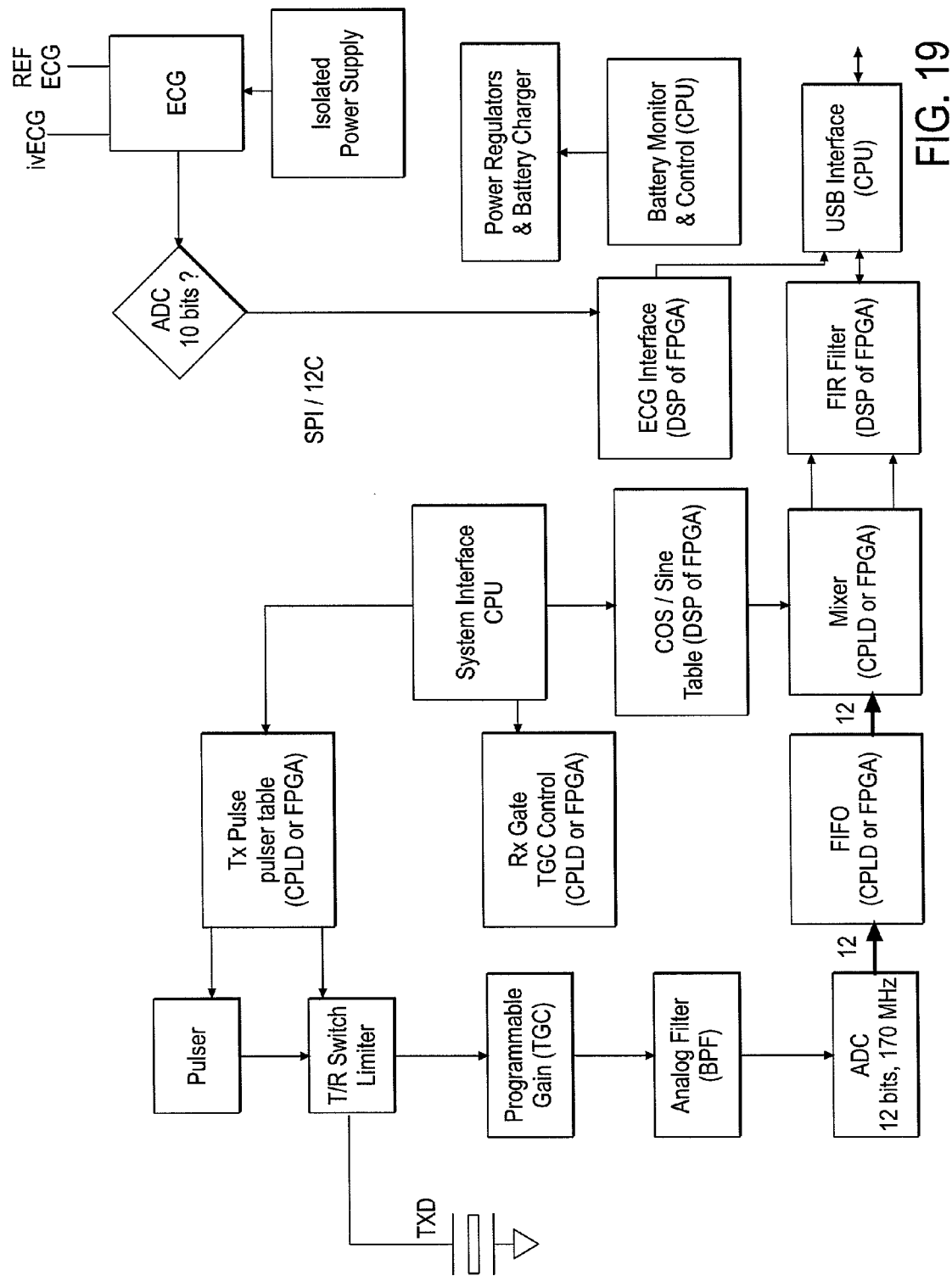
FIG. 19 is a flow chart illustrating the functioning of a data acquisition system of FIG. 6.

FIG. 19 illustrates more detail of the functional blocks of an exemplary Data Acquisition System 1 (from FIG. 6). These components are those found in conventional ultrasound systems.

The signal flow path illustrated and described with regard to FIG. 19 details how two different physiological parameters may be sampled, acquired and digitalized for processing according to the methods and systems described herein. While FIG. 19 may specific reference to ECG and Doppler, it is to be appreciated that the acquisition, conversion, processing and correlation described herein may be applied generally to ultrasound and electrogram signal combinations including a variety of different ultrasound modes and various different types of sources of electrogram signals. Moreover, ablation, acquisition, conversion, processing and correlation steps, components and capabilities may be included in the system 100 as needed depending upon the type and number of sensors employed on the endovascular device 150

Returning to FIG. 19, the ultrasound transducer (TXD) 120 which can be driven as Doppler and A-mode imaging is attached to a transmit/receive (T/R) switch to support pulsed wave operation. In some configurations, the connection between transducer and system may be optically isolated. The Pulser block generates the ultrasound signal used to drive the transducer 120. Exemplary signals are between 7-14 MHz. The Tx pulser table is firmware which allows the system to define the exact shape of the pulse train generated by the Pulser. The Programmable Gain (TGC) block implements variable gain, in particular useful for time-depth gain compensation. The Analog Filter (BPF) is a band-pass filter used to filter out unwanted high and low frequency signals, e.g., noise and harmonics. The Rx Gate and TGC Control block is used to select the sample volume range (depth) and width, i.e., the target volume from where the incoming (i.e. reflected) ultrasound signals are acquired. In the case of Doppler, the sample volume range (depth) and width defines the blood pool volume which is analyzed for velocity information. In the case of A-mode acquisition, the range extends from the transducer face to the entire available depth of penetration, and maximum width. In addition the Rx Gate and TGC Control is used to control the TGC block for the appropriate values with respect to the range and width of the sample volume. The ADC block converts the incoming analog signal into digital signal. Typical values for the high frequency A/D conversion are 12 bit depth of conversion and more than 100 MHz conversion rate. The FIFO block contains ultrasound digitized data corresponding to the sample volume as selected by the Rx Gate and TGC control block. The System Interface block (CPU) allows for the following functional blocks to be programmed algorithmically or by the user via a general purpose computer (CPU): Tx Pulse and Pulser Table, Rx Gate and TGC Control, and the Cos/Sin Table. The Cos/Sin Table is a building block that is used for the quadrature demodulation of the high frequency signal. The quadrature demodulation Cos/Sin table can be implemented either in software as a DSP (digital signal processor) function or as firmware in an FPGA (field programmable gate array). The Mixer multiplies the incoming signal with qudratue cos and sin signals to obtain 90 degrees phase shifted signals which allow for extracting the Doppler frequency shift from the incoming signal. The Mixer block can be implemented either as a DSP or an FPGA function. The FIR (finite impulse response) filter is used to filter the directional Doppler signals. An interface is provided to transfer digital ultrasound and electrogram (or other sensor) information to the host computer (CPU). The interface can interface either as a standard USB interface (shown in FIG. 19), as a network interface using TCP/IP protocols or any other kind of digital bidirectional real-time interface. The Power Regulators & Battery Charger provides power to the Acquisition System and charge the batteries in a battery-powered configuration. The Battery Monitor & Control block provides the interface (control and monitor) of the battery and power by the host computer (CPU). IN this example, the electrogram signal path consists of two connectors to the endovascular device (leads 130/135) and/or a reference lead 112, as needed. The connectors may be optically isolated for patient safety. The ECG block consists of an amplifier of ECG signals powered by the Isolated Power Supply. The ADC digitizes the ECG signal with 8 to 12 bits at a sampling rate of 100 Hz to 1 KHz.

Figure 20:
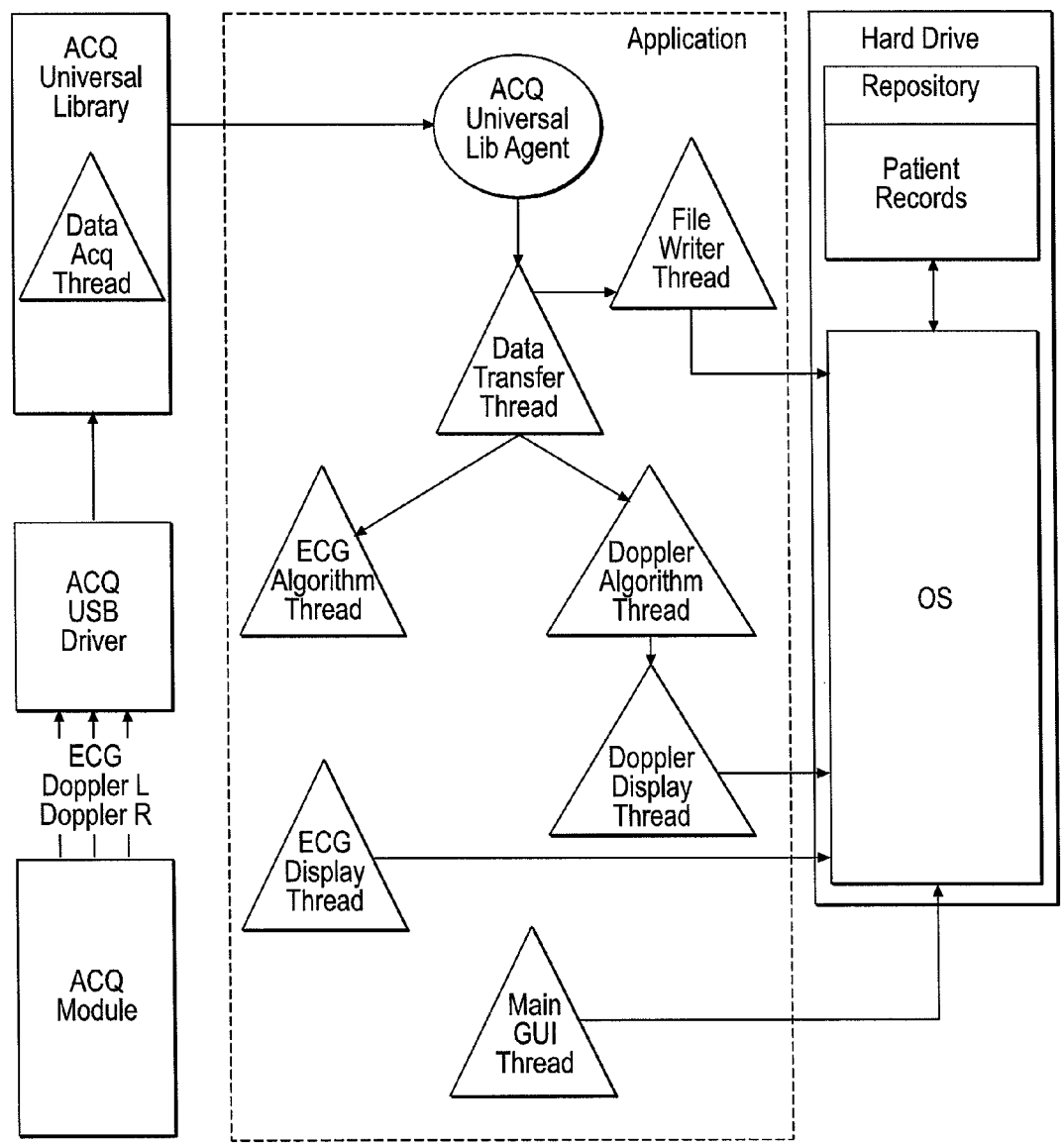
FIG. 20 is a flow chart illustrating an exemplary software block diagram of FIG. 6.

FIG. 20 illustrates an exemplary software block diagram 4 (FIG. 6) for providing the processing capabilities used by embodiments of the present invention. The main software application consists of several real-time threads running concurrently on the host computer platform. The ACQ Universal Lib Agents controls the acquisition of Doppler and ECG data. The Data Transfer Thread distributes the data to the ECG Algorithm Thread, the Doppler Algorithm Thread and the File Writer Thread. The Data Transfer Thread also ensures synchronization between the ECG and the Doppler data streams, such that, for example, ECG gated/synchronized Doppler analysis can be implemented. The File Writer Thread streams unprocessed real-time Doppler and ECG data to a storage device, e.g., hard disk. The benefit of this approach is, that in playback mode, i.e., when reading data from the storage medium through the File Writer Thread, the data can be processed at a later time exactly the same way it was processed at acquisition time. The ECG and Doppler Algorithm Threads implement real-time feature extraction and decision making algorithms as describes herein.

The ECG and Doppler Display Threads display ECG and Doppler information on the graphical user interface (GUI) in real-time. The Main GUI Thread is responsible for user interaction, system settings, and thread and process synchronization and control. In the embodiment illustrated in FIG. 20, the software applications interact with a number of other components. An operating system, e.g., Windows, Linux, or a real-time embedded operating system, e.g. VxWorks provides the infrastructure for the application to run and a number of services, e.g., interface to a database for patient data repository. The ACQ Universal Library provides software functions which control the data acquisition hardware. The ACQ USB Driver or a TCP/IP network driver or any other kind of communication driver controls the communication channel between the Acquisition System (Module) and the host computer platform. Through this bidirectional communication channel Doppler and ECG information is transferred from the ACQ Module and control information is transferred towards the ACQ Module.

Algorithms

Figure 7:
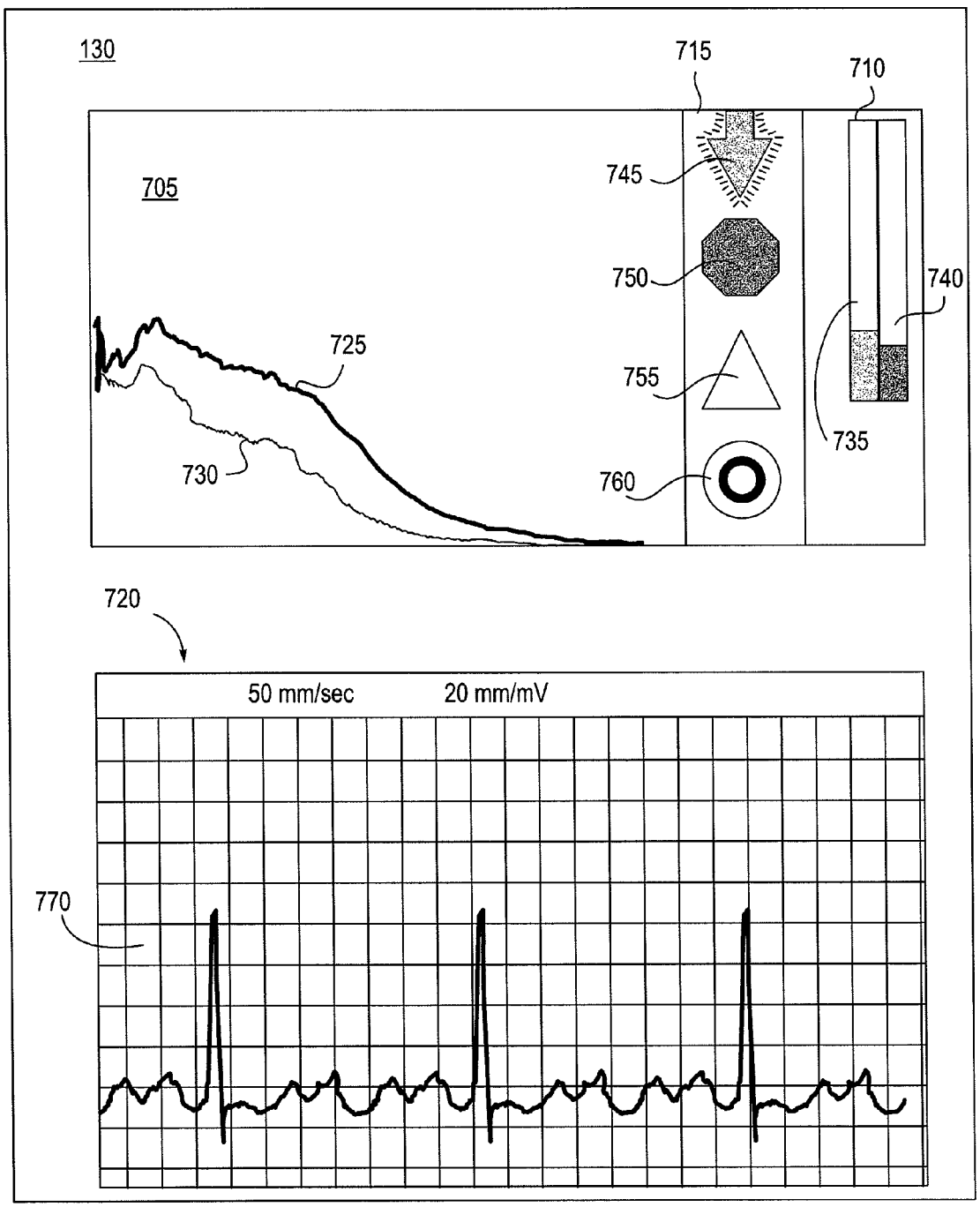
FIG. 7 illustrates the flow velocity profiles, the intravascular ECG signal and their correlation as detected by the device according to the present invention in the superior vena cava as documented by the synchronized fluoroscopic image.
Figure 8:
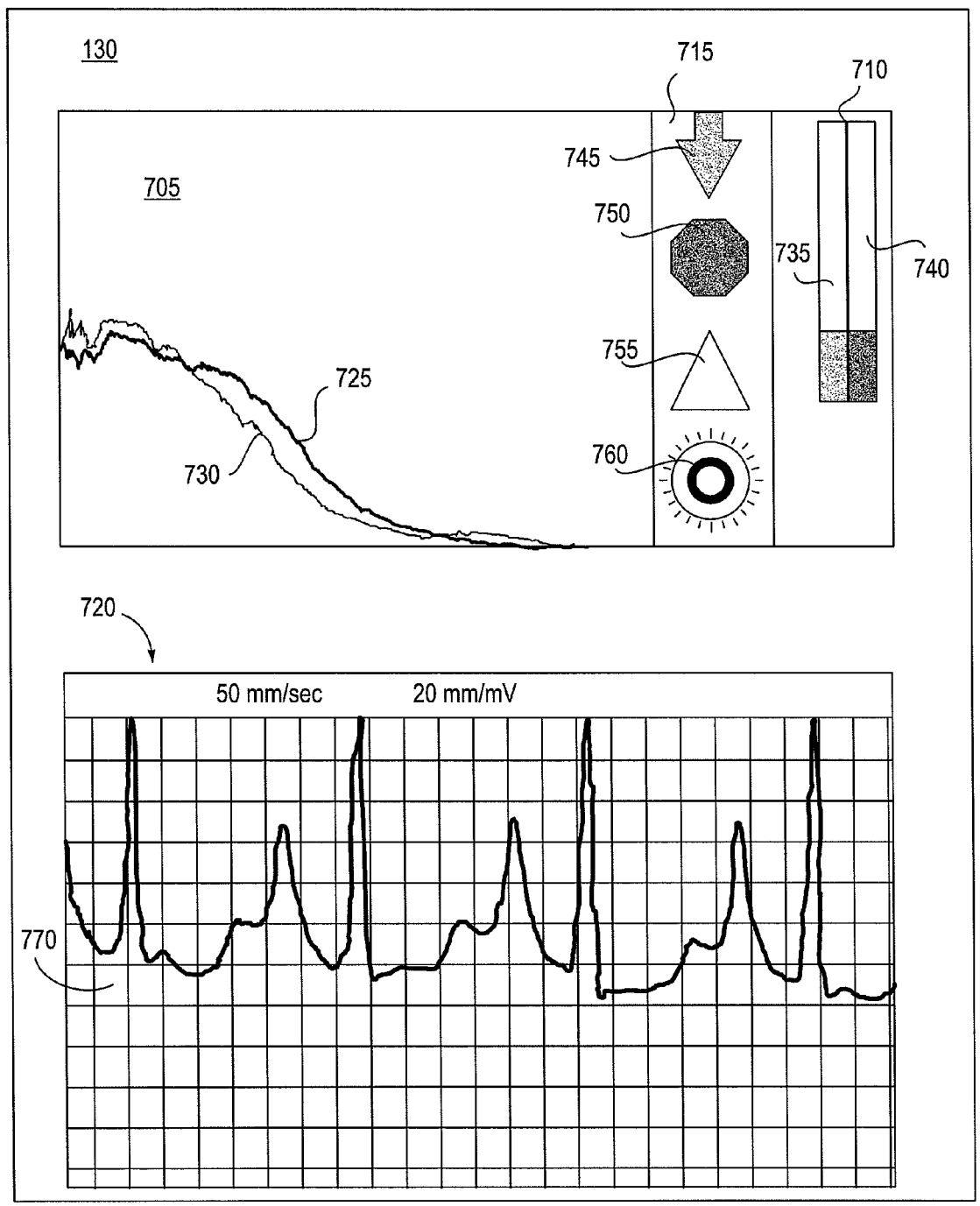
FIG. 8 illustrates the flow velocity profiles, the intravascular ECG signal and their correlation as detected by the device according to the present invention at the caval-atrial junction as documented by the synchronized fluoroscopic image.
Figure 9:
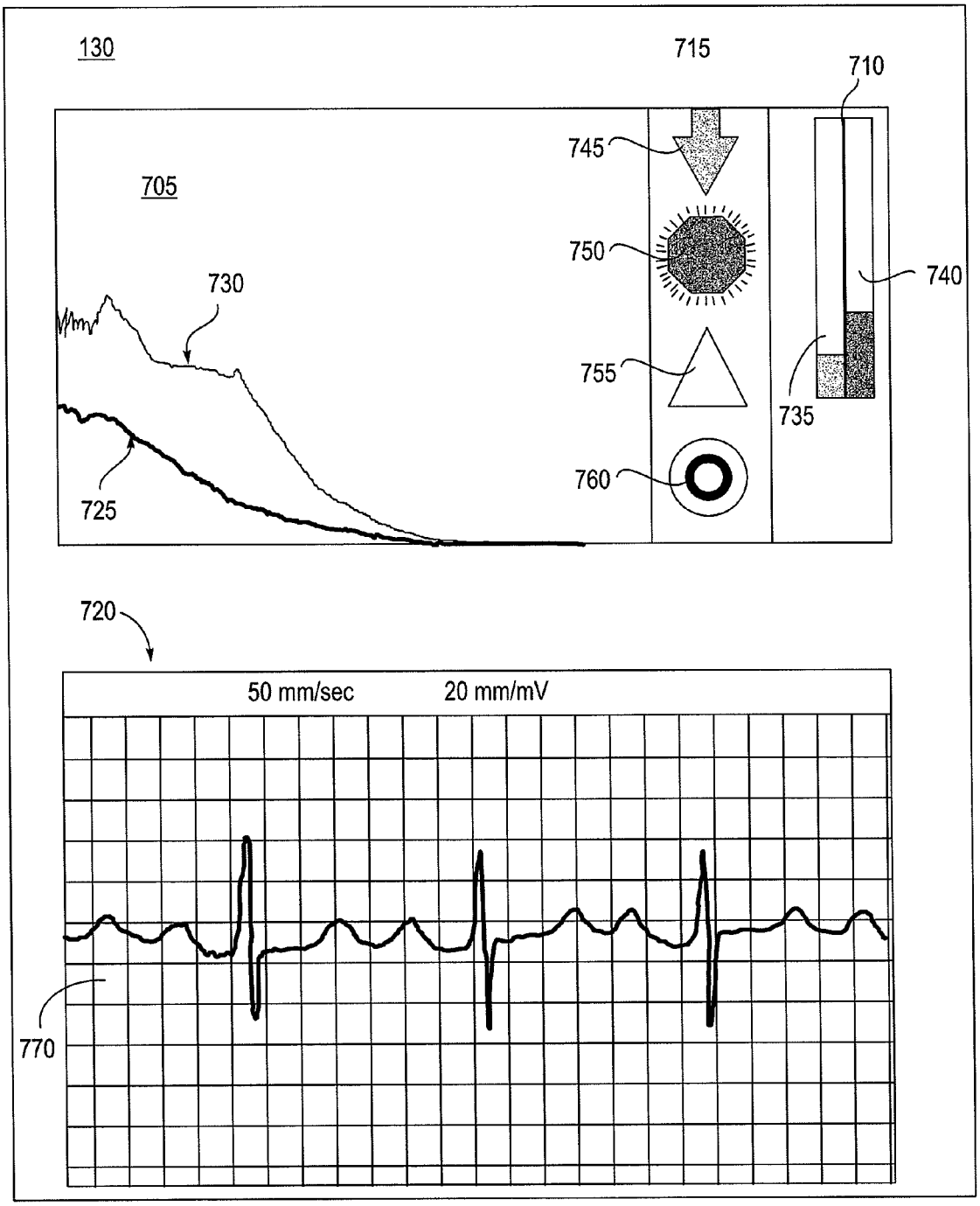
FIG. 9 illustrates the flow velocity profiles, the intravascular ECG signal and their correlation as detected by the device according to the present invention in the internal jugular vein as documented by the synchronized fluoroscopic image.

In one embodiment, the system according to the current invention uses two types of physiological parameters detected by the sensor-based endovascular device 150 in order to determine the location of the endovascular device 150 in the vasculature. In the examples that follow, the parameters are ultrasound determined blood flow patterns and intravascular electrocardiogram patterns. FIGS. 7, 8, and 9 are views of a display 130 that illustrate blood flow and electrocardiogram patterns at different locations in the vasculature.

The display 130 illustrated in FIGS. 7, 8 and 9 includes: a flow velocity profile output 705; a bar graph 710; a plurality of indicators 715; and an electrogram output 720. The flow velocity profile output 705 includes a curve 725 related to the flow away from the sensor and a curve 730 related to the flow towards the sensor. The relative power of these flows towards and away are reflected in the bar graph 710. The bar graph 710 has an indication 740 for flow towards the ultrasound sensor and an indication 735 for flow away from the ultrasound sensor. The bar graph 710 may be color coded. One color scheme would represent flow away as green and flow towards as red. Based on the processing performed as described herein, the system is able to determine several different states or conditions for the endovascular device 150. The indicators 715 are used to represent these conditions to a user viewing the display 140. One indicator may be used to represent movement of the device 150 in the desired direction. In the illustrative embodiment, the arrow 745, when illuminated, indicates proper direction of flow. The indicator may be colored coded, such as green. One indicator may be used to represent improper or undesired movement of the device 150. In the illustrated embodiment, the octagon shape 750 when illuminated, indicates direction to travel in an undesired direction. This indication may be color coded red. Another indication may be provided to indicate to the user that the system cannot determine or is unsure about device 150 position or movement. The triangle 755 is used for this indication. This indicator may be color coded yellow. Another indicator may be used to inform a user that the system has determined that the device 150 is in a position where the sensors on the device are detecting signals of the target location when the system detects, for example, blood flow patterns and electrogram signals of the target location, the indicator 760 is activated. Here, the indicator 760 is one or more concentric rings representing bullseye. This indicator may also be color coded, such as with the color blue. The electrogram output 720 displays the electrogram signals detected by the electrogram leads used by the system. The outputs displayed each of FIGS. 7, 8 and 9 correspond to actual data and results obtained using a device and system as described herein. For comparison, each of the ECG displays 720 are the same scale to facilitate comparison of the ECG wave from at each position. Similarly, the flow curves 725, 730 (and corresponding relative sizes of the bar graph indications 735, 740) are also representative of actual data collected using the devices and techniques described herein.

The display 130 illustrated in FIGS. 7, 8 and 9 includes a flow velocity profile 705 bar graph 710, indicators 715 and an electrogram output 720.

FIG. 7 illustrates the blood flow velocity profile (705), the intravascular ECG (770), indicator 715 (with 745 illuminated) and bar graph 710 when the tip of the endovascular device 150 is in or moving with venous flow towards the superior vena cava (SVC).

When the device moves with the venous flow towards the heart, the blood flow away from the sensor dominates the blood flow towards the sensor as shown by the relative position of curves 725 and 730 and bar graphs 735, 740. The ECG 770 in FIG. 7 illustrates the typical base line ECG expected in most locations when the device 150 is away from the heart.

FIG. 8 illustrates the blood flow velocity profile (705), the intravascular ECG (770), indicator 760 and bar graph 740 when the tip of the endovascular device at the caval-atrial junction. When the device 150 is positioned at a target location, correlation of the various unique signatures of the target location may be used to add confidence to the device position. When the device is at a target site near caval-atrial junction then the blood flow toward/away from the sensor are nearly balanced because of the flows converging from the superior vena cava of the inferior vena cava. This nearly equivalent flow toward/away is represented by the proximity of the curves 725/730 as well as bars 735/740. Importantly, the ECG 770 indicates the prominent P-wave that indicates proximity of the ECG lead to the SA mode. The presence of the larger P-wave is an example of a physiological parameter that is used to correlate the flow information and confirm device placement.

FIG. 9 illustrates the blood flow velocity profile (705), the intravascular ECG (770), indicator 715 and bar graph 710 when the tip of the endovascular device is in the internal jugular vein. When the endovascular device 150 enters the jugular, the flow towards the sensor now dominates the velocity profile as reflected in the relative positions of the curves 730, 725 and the bars 735, 740 in bar graph 710. Additionally, the ECG wave demonstrates a unique QRS polarity (i.e., the QRS complex is nearly equal negative and positive). This distinctive ECG profile is used to confirm that the device 150 has entered the jugular vein. Criteria for feature extraction and location identification can be developed for both the time and the frequency domain as well as for other relationships that exist between criteria in time vs. frequency domains.

Figure 21:
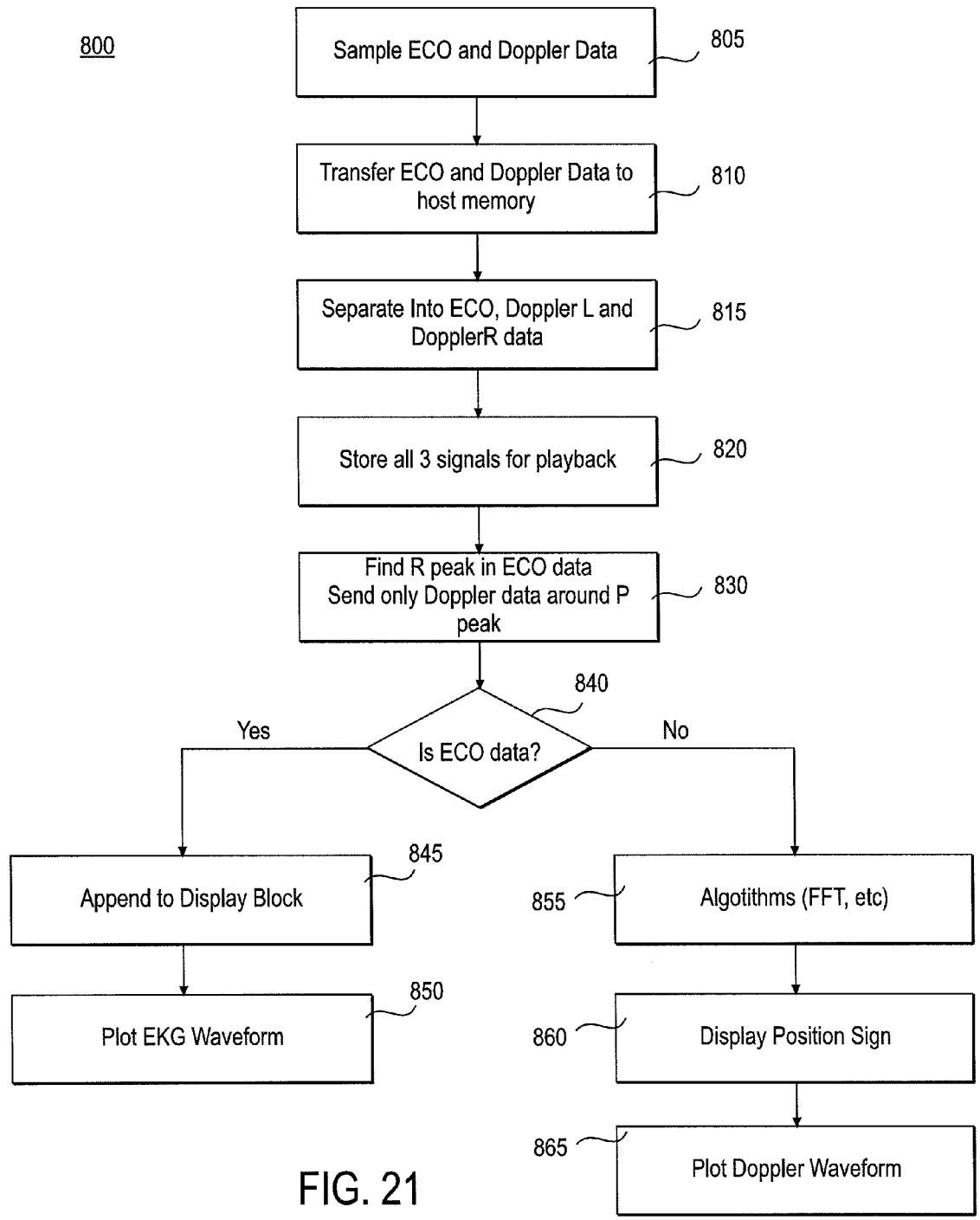
FIG. 21 is a flow chart illustrating an exemplary processing algorithm for multi-parameter signal processing and correlation.

FIG. 21 illustrates the flow chart 800 implementing an exemplary algorithm according to one aspect of the present invention. First, at step 805, Doppler and electrocardiogram/ECG (ECO) signals are sampled at the desired frequency, typically between 20 to 50 KHz/channel for the Doppler data and 100 Hz to 1 KHz for the ECG data. Next, at step 810, the ECG (ECO) and Doppler data are transferred to the host computer memory. Next, at step 815, Doppler directional data (antegrade and retrograde or left and right channel) and ECG data are separated at different memory locations since they come packed together in the incoming data stream from the sampler. Next, at step 820, the three data streams (Doppler antegrade, Doppler retrograde, and ECG) are streamed to the storage in sync. Next, at step 830, the algorithms identifies the R-peak in the ECG data stream and then locates the P-wave segment within 400 to 600 ms to the left of the R-peak. If the answer to block 840 is yes, then the ECG/ECO data is then appended to the display buffer (step 845) and plotted on the graphical user interface (step 850). If the answer in block 840 is no, then the Doppler data corresponding to a desired period in the heart beat, e.g., during the P-wave, during the QRS-complex, or during the entire heart beat is processed as in steps 855, 860 and 865 through FFT and filters and further described below. Based on the results of processing, blood flow direction and tip location information about the endovascular sensor-based device is presented on the display and the Doppler information is plotted on the display.

In general, software controls to algorithms can be applied to the frequency domain after performing a Fast Fourier Transform (FFT) or in the time domain (No FFT). Typical number of points for the FFT are 512, 1024, 2048, 4096. These numbers represent the length of a data vector. The signal can be averaged over time or over the number of samples both in time and frequency domains. The on-line averaging uses a filter window of variable length (between 3 and 25 samples) to average along a data vector. The multi-lines averaging computes the average of a selectable numbers of data vectors. The can spectral power can be computed in frequency domain from the shape of the power spectrum for each of the considered signals (directional Doppler and ECG). The spectral power of the directional Doppler spectra is used to differentiate between retrograde and antegrade blood flow. Selective filtering of certain frequencies is used to remove undesired artifacts and frequency components, e.g., high frequencies indicative of a high degree of turbulence. Selective filtering also offers the ability to look consider certain frequencies as being more important than other in the decision making process. For example the lowest and the highest relevant frequency of the spectrum, i.e., the lowest and the highest relevant detected blood velocity can be associated to certain location in the vasculature and n the blood stream. Threshold values are used to make decisions regarding the predominant flow direction and the presence of the QRS-complex or the P-wave. The threshold values can be computed using an auto-adaptive approach, i.e., by maintaining a history buffer for data and analyzing tendencies and temporal behavior over the entire duration of the history data buffer.

Criteria useful in assessing location in the vasculature based on ultrasound and ECG information are described below. Some of the criteria which can be used to determine sensor location in the vasculature from the blood flow velocity profiles are: a) comparing energy, for example as measured by spectral power in frequency domain, of each of the directions of bidirectional flow; b) bidirectional flow patterns in lower velocity range to detect the caval-atrial junction; c) pulsatility to detect atrial activity; d) the highest meaningful average velocity of the velocity profile and others described herein.

Some of the criteria which can be used to determine sensor location in the vasculature from the intravascular ECG are: a) peak-to-peak amplitude changes of the QRS complex or of the R-wave; b) P-wave relative changes; c) changes in the amplitude of the P-wave relative to the amplitude of the QRS complex or of the R-wave; and others as described herein. The correlation between the shape of the intravascular ECG waveforms and the shape of the blood flow velocity profile as well as the correlation between the relative changes of the two can also be used as criteria for determining positioning, guiding or confirming sensor location in the vasculature.

Returning to FIGS. 7, 8 and 9, in display 705, the horizontal axis represents the Doppler frequency shift proportional to the blood velocity and the vertical axis the amplitude of a certain frequency, i.e., the power (or energy) or how much blood flows at that particular velocity (frequency). The curve 725 illustrates the velocity distribution at the Doppler sensor location of blood flowing away from the sensor. The curve 730 illustrates the velocity distribution at the Doppler sensor location of blood flowing towards the sensor. Typically, the curve 725 is green and the curve 730 is red for applications where the desired movement is towards the heart. Other color codes could be used for a different vascular target. For the color-blind, directions of flow can be indicated using symbols other than colors, e.g., '+' may indicate flow away from the sensor and '−' may indicate flow towards the sensor, or numbers may indicate strength of flow. Scrollbars can also be used to indicate intensity of bidirectional flow. Bar graphs 710, 735, 740 may also be used. Another way to indicate direction of flow and to identify certain flow patterns to the user is by using audible signals, each signal being indicative of a certain flow, or in general, of tip location condition. A green arrow (745), a green bull's eye (760), or a red stop sign (750) can be used as additional indicators for flow conditions and, in general, to identify the location of the sensor in the vasculature. In ECG 770, the horizontal axis represents time and the vertical axis represents the amplitude of the electrical activity of the heart. The algorithms described herein may be applied to the electrical mapping of the heart activity independent of how the electrical activity was recorded. Devices described herein may record intravascular and intracardiac ECG. Other methods of recording ECG, for example using a commercially skin ECG monitor (such as lead 112 in FIG. 1), are also possible and may be used as described herein.

Referring again to FIGS. 7, 8 and 9, one criterion used for correlating the Doppler frequency (velocity) distributions to the anatomical locations refers to the spectral power or the area under a specific Doppler frequency curve (the integral computed of the frequency spectrum) in conjunction with the uniformity of differences in frequencies over the entire frequency range. In FIG. 7 the sensor is positioned in the superior vena cava looking towards the heart and with the main blood flow stream moving away from the sensor towards the heart. The green area is larger than the red one and, in this case, the curve 725 is above curve 730 over the whole range of Doppler frequencies (velocities). In FIG. 9, the catheter tip has been pushed into the jugular vein. The blood is flowing towards the heart and towards the sensor located at the catheter tip. The area under the red curve 730 is larger than the area under the green curve 725 and the velocities in red (towards the sensor) are larger than the velocities in green over the entire range of velocities in this case. In each of FIGS. 7 and 9, the bar graph 710 indicates as well as the relative sizes of flow towards and away from the sensor.

Consequently, if the blood velocity profile shows larger spectral power in one direction it is inferred that this is the predominant direction of flow of the blood stream.

Another criterion is related to the distribution of the low velocities in the two directions (i.e., towards and away from the sensor). In a vein, the blood velocities are different than, for example in the right atrium. Therefore most of the relevant spectral energy will be present in the low velocity range. Typically, low blood flow velocity range is from 2 cm/sec to 25 cm/sec.

Another criterion is the similarity between the green (toward) and the red (away) curves. At the caval-atrial junction (FIG. 8) the green and red curves are almost identical with similar areas (similar energy or the area under curves 725/730) and with similar velocity distributions (similar velocity profiles or shape of the curves 725, 730). This is indicative of the similar inferior vena cava (IVC) and superior vena cava (SVC) flow streams joining together from opposite directions when entering the right atrium.

Another criterion is the behavior in time of the flow patterns and signatures. In particular the behavior refers to the difference between strongly pulsatile flow present in the right atrium, in the heart in general as well as in the arterial flow compared to the low pulsatility characteristic of venous flow.

Another criterion takes into account a periodic change in behavior of the flow profiles with the heart rate. A stronger periodic change with the heart rate or pulsatility is indicative of the right-atrial activity.

Another criterion is the amplitude of the green and red curves. The higher the amplitude at a certain frequency, the higher the signal energy, i.e., the more blood flows at the velocity corresponding to that particular frequency.

Another criterion is the amplitude of the highest useful velocity contained in the green and red velocity profiles. Useful velocity is defined as one being at least 3 dB above the noise floor and showing at least 3 dB of separation between directions (green and red curves). The highest useful velocity according to the current invention is an indication of the highest average velocity of the blood stream because the device according to the present invention intends to measure volumetric (average) velocities.

Figure 11:
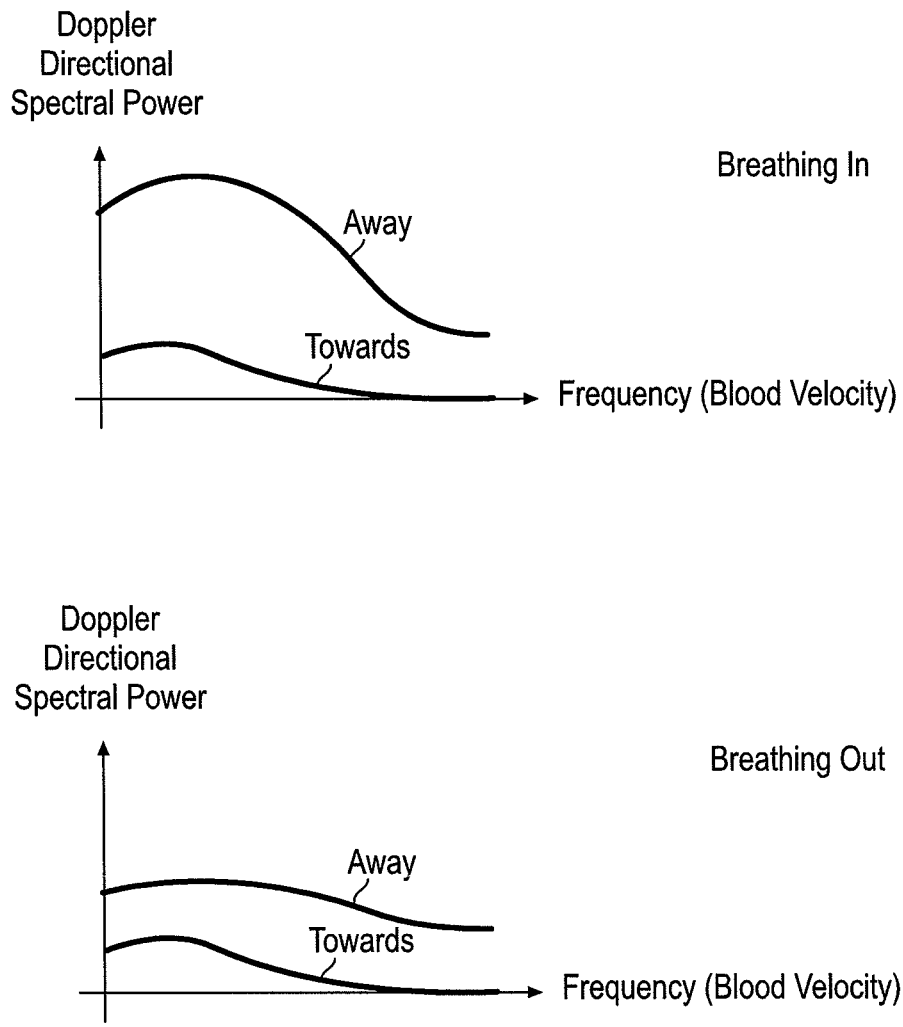
FIG. 11 illustrates the effect of using additional gating based on patient's breathing on the acquisition and processing of blood flow information.

Another criterion is the temporal behavior of the velocity profiles at a certain tip location. If the tip location is further away from the heart, e.g, in the internal jugular vein, then the predominant temporal behavior may be pulsatility due to respiration of the main blood stream. FIG. 11 represents exemplary flow patterns based on this concept. In the internal jugular vein the main blood stream is represented by the red curve (blood flows against the sensor). Closer to the heart and in particular in the right atrium, the predominant temporal behavior is pulsatility related to the heart beat.

Another criterion is related to the absolute and relative changes of the P-wave at different locations within the vasculatire. As represented by ECG 770 in FIGS. 7, 8 and 9, the P-wave dramatically increases at the caval-atrial junction (FIG. 8) when compared to the P-wave in the superior vena cava (FIG. 7) or the internal jugular vein (FIG. 9). Additional criterion relate to the P-wave relative amplitude when compared to the QRS complex and the R-wave.

FIG. 12 illustrates that even in the case of patients with atrial fibrillation, the atrial electrical activity, which may not be seen on the regular skin ECG becomes visible and relevant as the intravascular ECG sensor approaches the caval-atrial junction. Both the amplitude of the atrial electrical activity and its relative amplitude vs. the QRS and R-waves change visibly at the caval-atrial junction in the close proximity of the sino-atrial node.

With reference again to FIGS. 7, 8 and 9, another criterion is related to the absolute and relative changes of the QRS complex and the R-wave at different locations. The R-wave and the QRS complex dramatically increase at the caval-atrial junction (FIG. 8) when compared to the waveforms in the superior vena cava (FIG. 7) or the internal jugular vein (FIG. 9). Its relative amplitude to the P-wave also changes dramatically. FIG. 12 shows that even in the case of patients with atrial fibrillation, the R-wave and the QRS complex change significantly as the intravascular ECG sensor approaches the caval-atrial junction. Both the amplitude of the R-wave and QRS complex and their relative amplitude vs. the P-waves change visibly at the caval-atrial junction in the close proximity of the sino-atrial node.

Any individual criterion and any combination of the above criteria may be used to estimate location in the vasculature. A database of patterns can be used to match curves to anatomical locations instead of or in addition to applying the above criteria individually.

Figure 10:
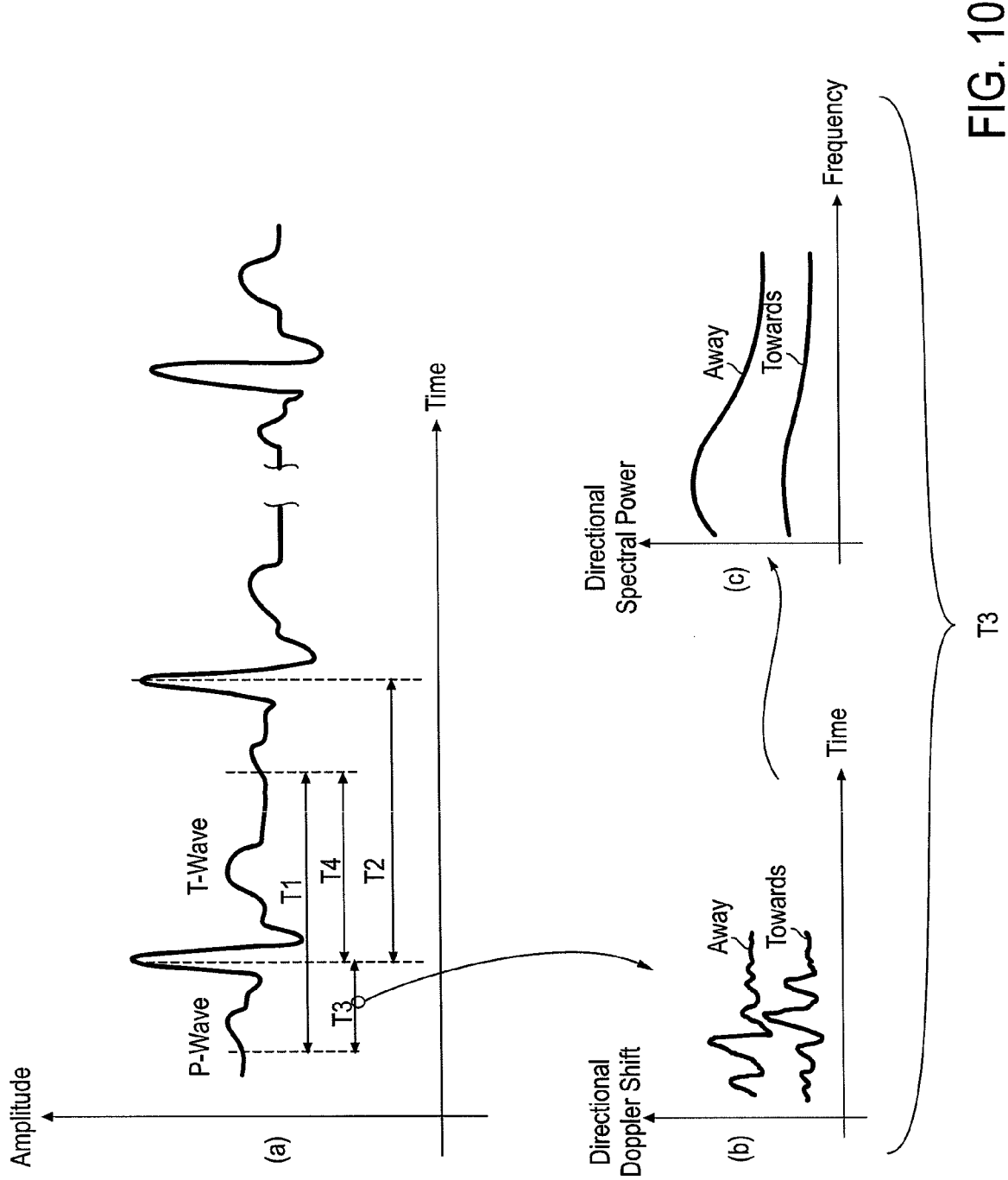
FIG. 10 illustrates the use of intravascular ECG signal to gate or trigger the acquisition or processing of the blood flow information.

FIG. 10 illustrates how the endovascular electrical signal can be use to trigger and gate the processing of the ultrasound signals. The electrical signal acquired from the endovascular sensor is periodic and related to the heart cycle (10*a*). It is similar in shape with a known diagnostic ECG signal. By analyzing the waveforms, e.g, P-wave, QRS complex and the T-wave, a number of events and time segments can be defined in the heart cycle. The P-wave event occurs when the P-wave amplitude is at its peak. The-R-wave event occurs when the R-wave amplitude is at its peak. Other events can be defined, e.g., when the R-wave amplitude is one third lower than the peak. Between such events time intervals can be defined. T1 is the time interval between 2 consecutive P-waves and indicates the heart rate. T2 is the time interval between two R-waves and similarly indicates the heart rate. T3 is the time interval between the P and the R waves. T4 is the time interval between the R-wave and the subsequent P-wave. Other time intervals can be defined, as well. These intervals can be defined in reference to a peak value of a wave, the beginning or end of such a wave, or any other relevant change in the electric signal. The events defined in a heart cycle can be used to trigger selective acquisition and/or processing of physiological parameters through the different sensors, e.g., blood flow velocity information through the Doppler sensor. The time intervals can be used to gate the acquisition and processing of physiological parameters like blood velocity, e.g., only in the systole or only in the diastole. Thus more accurate results can be provided for guiding using physiological parameters. Graphs 10*b* and 10*c* illustrate exemplary ultrasound data triggered on the T3 interval.

FIG. 11 illustrates how the variations in blood flow as identified by the Doppler signal can be used to trigger and gate signal acquisition and processing based on the respiratory activity of the patient. The flow patterns as indicated by the Doppler power spectrum change with the patient's respirations. Certain cardiac conditions like regurgitation also cause changes in the flow patterns with respiration. Such changes with respirations can be identified, in particular when the strength of a certain pattern changes with respirations. These identified changes can then be used to trigger and gate the acquisition and processing of physiological parameters relative to the respiratory activity of the patient. Thus more accurate results can be provided for guiding using physiological parameters.

FIG. 12 illustrates how the relative changes in the QRS complex can be used to identify proximity of the sinoatrial node even in patients with atrial fibrillation, i.e., patients without a significant P-wave detected by diagnostic ECG. In patients with atrial fibrillation, the P-wave cannot be typically seen with current diagnostic ECG systems (see (1)). Still changes, i.e., significant increases in the QRS complex amplitude as identified by an endovascular sensor are indicative of the proximity of the sino-atrial node (See (2)). In addition, an endovascular devices can measure electrical activity which is not detected by a standard ECG system, e.g., the atrial electrical activity in a patient thought to have atrial fibrillation (See (3)). Such changes in the waveform of the endovascular electrical signal can be used to position the sensor and the associated endovascular device at desired distances with respect to the sino-atrial node including in the lower third of the superior vena cava or in the right atrium.

Graphical User Interface

Figure 13:
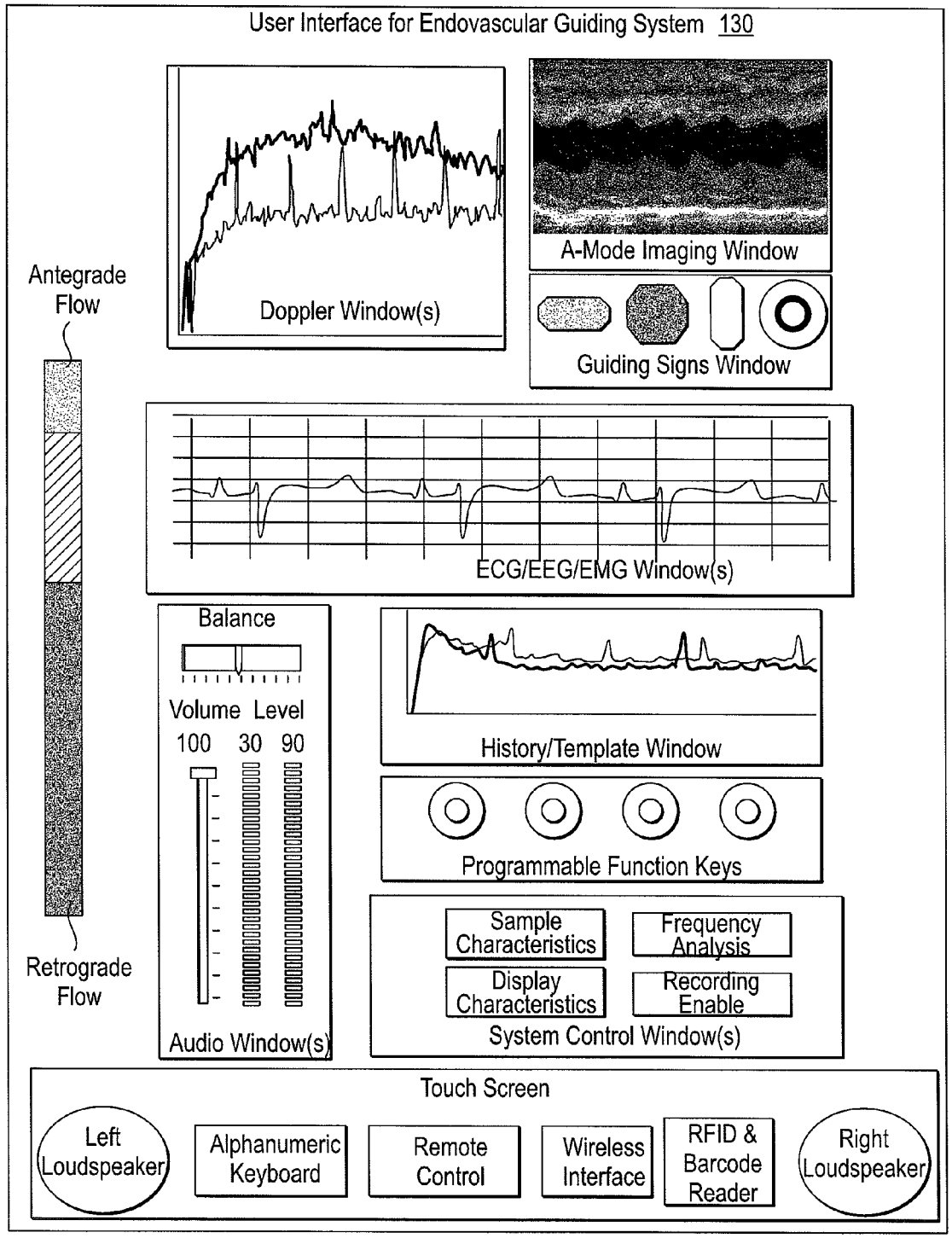
FIG. 13 illustrates a graphical user interface displaying blood flow information, intravascular ECG signals, their correlation, and catheter tip location information based on the above.
Figure 14A:
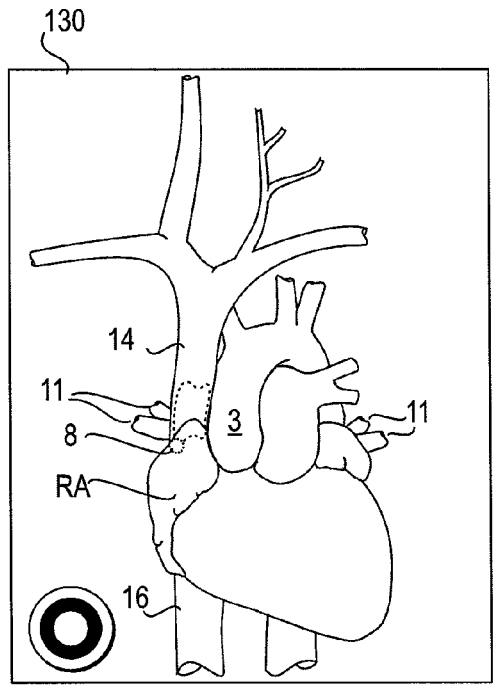
FIGS. 14A-14D illustrates a simplified user interface using blood flow information, intravascular ECG signals and their correlation to display if the endovascular member is advancing towards the caval-atrial junction and sinoatrial node, if the endovascular member is advancing away from the caval-atrial junction and sinoatrial node, or if the endovascular member is at the caval-atrial junction proximal to sinoatrial node.
Figure 14B:
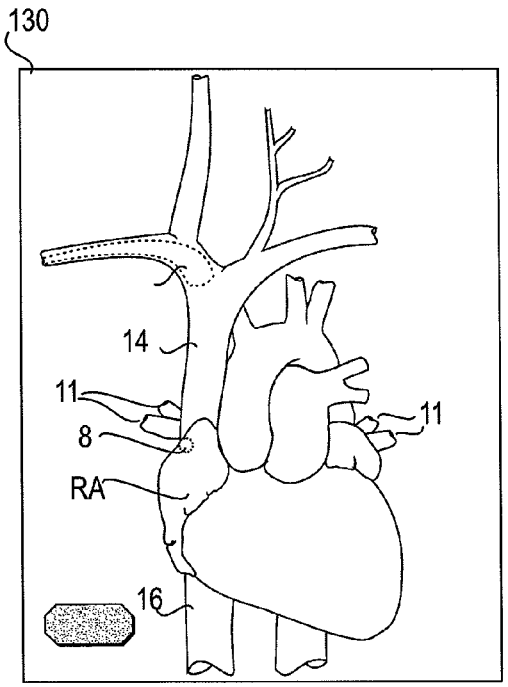
Figure 14C:
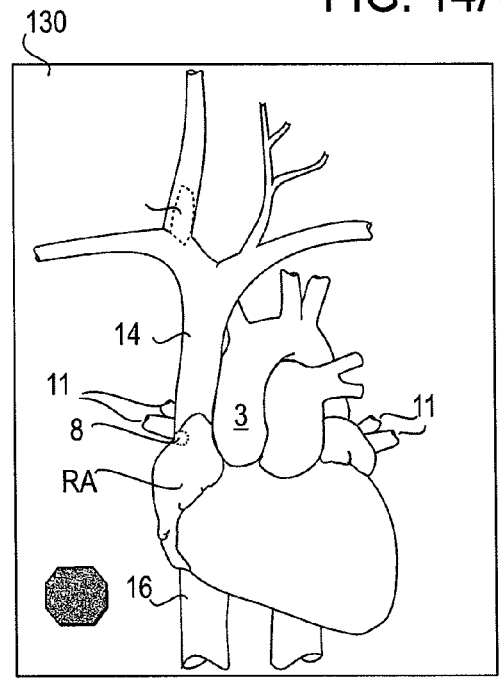
Figure 14D:
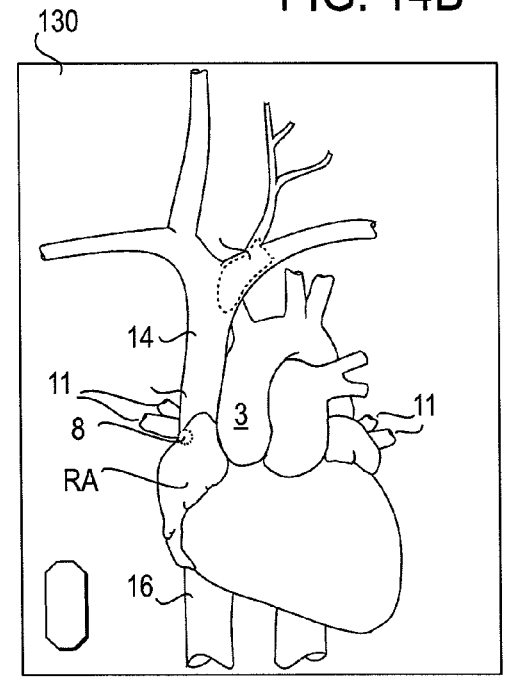

FIG. 13 illustrates elements of an exemplary display 130 configured as a graphical user interface (GUI) for a vascular access and guidance system as described herein. The display 130 in FIG. 13 integrates in a user-friendly way different guiding technologies for vascular access: Doppler, ECG, audio, workflow optimization, A-Mode imaging, for example. The Doppler window presents the characteristics of the blood flow as detected using Doppler or cross-correlation methods. The information can be presented in either the time or the frequency domain. In the case of bidirectional Doppler, the two directions can be represented on a single display or on two different displays. Several Doppler windows can be stacked and accessed though tabs in order to either provide a history of the case or to access a template database. Alternatively the history/template window can be displayed separately on the instrument screen. The A-Mode Imaging window presents ultrasound information in a graph of time (x dimension) version depth (y dimension). The window gets updated regularly such that the movement of the hand holding the A-Mode imaging device appears to be in real-time. This increases the ability of hand-eye coordination. Typically the origin of an A-mode single beam is on top the screen and the A-Mode ultrasound flash light is looking down. Another use for the A-Mode imaging display window is to allow for imaging and identification of blood clots. The Guiding Signs window consists of colored elements of different shapes that can be turned on and off. For example when the Doppler window displays a much larger curve than a red one, then the green light in the Guiding Signs window is turned on and all other lights are turned off. The red light on (and the others off) indicated that the endovascular sensor is pointing in the wrong direction. A yellow light on indicates that the signal is not strong/clear enough to make a determination. The blue light on indicates that the sensor senses blood flow characteristic of the caval-atrial junction.

The ECG window displays electrical signals detected by the endovascular probe. The window can display single or multiple electrical signals and one or more ECG windows may be displayed. The programmable function keys are shortcuts to different system functions. They can be accessed through the touch screen or remotely via a remote control. Typical function keys would select screen configurations and system functions or would provide access to default settings. The Audio window presents either the Doppler or the audio information received from the endovascular sensor. In a preferred embodiment the audio window is similar to the interface of a digital audio recorder showing the intensity of the channels (flow away and towards the probe) on simulated LED bars of potentially different colors. For the color blind numbers are also displayed showing the average intensity of flow in each direction. Alternatively, a single LED bar can be used, such that the different blood flow intensity in each direction is shown at the two extremities of the single LED bar potentially in different colors. The System Control Unit provides control over the data acquisition devices, system settings, information processing, display and archiving. Any combinations of the above described windows are possible and each window type can have multiple instances.

Display windows can be repositioned and resized, displayed or hidden. The screen layout is user configurable and user preferences can be selected and archived through the System Control Window. The System Control Window can display an alphanumeric keyboard which can be used through the touch screen. Character recognition capabilities can facilitate input using a pen. A touch screen enables the user to directly access all the displayed elements. The loudspeakers are used for the sound generated either by the Doppler or by auscultation components. The sound system provides for stereo sound and alternatively headphones can be used. In the case of Doppler information, the audible Doppler frequency shift corresponding to one blood flow direction, e.g., towards the probe can be heard on one of the stereo speakers or headphones, e.g., the left channel. At the same time, the audible Doppler frequency shift corresponding to the other blood flow direction, e.g., away from the sensor can be heard on the other of the stereo speakers or headphones, e.g., the right channel.

The system can be remotely controlled, networked or can transfer information through a wireless interface. An RFID and/or barcode reader allows the system to store and organize information from devices with RFID and/or barcode capability. Such information can be coordinated with a central location via, for example, a wireless network.

In many clinical applications, endovascular devices are required to have the device tip (distal end) to be placed at a specified location in the vasculature. For example CVC and PICC lines are required to have their tip placed in the lower third of the superior vena cava. However, for example due to lack of a guidance system at the patient's bedside, users currently place the catheters into the patient's body blindly, often relying on x-ray to confirm the location of the catheter a couple of hours after initial placement. Since the CVC or a PICC line can be released for use only after tip location confirmation, the patient treatment is delayed until after X-ray confirmation has been obtained. Ideally, users should be able to place the catheter at the desired location with high certainty and with immediate confirmation of tip location. Building a user-friendly, easy-to-use system which integrates electrical activity information with other types of guiding information, devices and techniques described herein.

FIG. 14 provides exemplary display 140 with an easy to use graphical user interface which combines location information from the different sensors and displays graphical symbols related to the location of the endovascular device. For example, if the endovascular device is advancing towards the caval-atrial junction a green arrow and/or a heart icon are displayed together with a specific audible sound as shown in FIG. 14B. If the endovascular device is advancing away from the caval-atrial junction then a red stop sign and/or a red dotted line are displayed together with a different specific audible sound as shown in FIG. 14C or 14D. If the tip of the endovascular device is at the caval-atrial junction than a blue or green circle or "bull's eye" is displayed together with a different specific audible sound as shown in FIG. 14A. Of course, any colors, icons, and sounds or any other kind of graphical, alphanumeric, and/or audible elements can be used to indicate the tip location.

Figure 15:
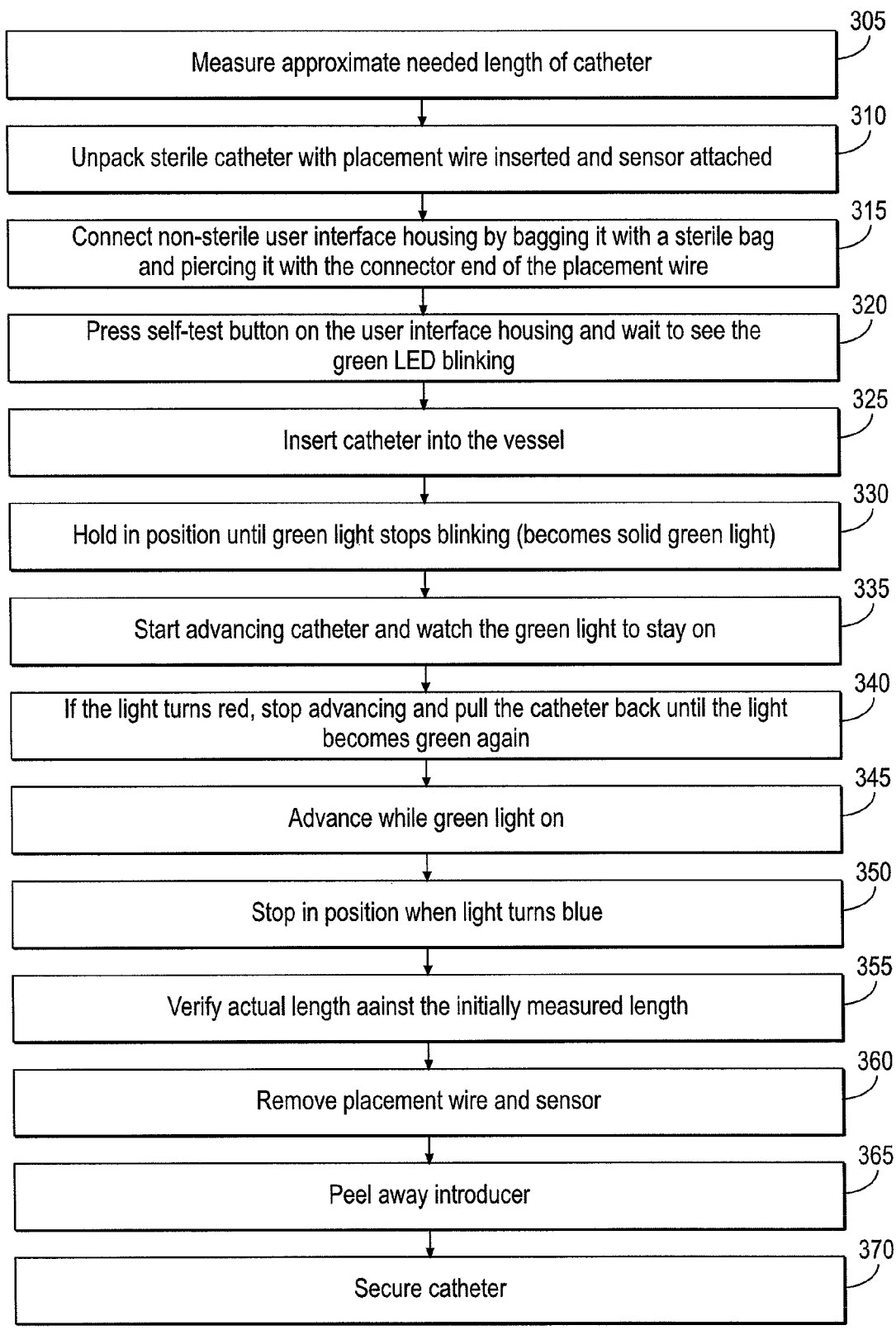
FIG. 15 is a flow chart of an exemplary endovascular placement method.

While the simplified user interface is displayed all the underlying information (Doppler, ECG, and others) can be digitally recorded so that it can be used to print a report for the patient's chart. Storing of patient information, exporting the data to a standard medium like a memory stick and printing this information to a regular printer are especially useful when the device and system disclosed in the current invention are used without chest X-ray confirmation to document placement at the caval-atrial junction of the endovascular device.
Ultrasound and ECG Methods of Positioning Guided Endovascular Devices FIG. 15 illustrates an exemplary method 300 of catheter placement. In this example, the method 300 describes how a user would place a PICC catheter using a guided vascular device with guidance information provided using blood flow information and ECG signals provided by the system and processing techniques described in greater detail in the current invention. This example is for illustration purposes only. Similar conventional catheter, guide wire or device introduction procedures, may be tailored for the requirements of other therapeutic devices such as, for example, for placement of hemodialysis catheters as well as for the placement of laser, RF, and other catheters for percutaneous treatment of varicose veins, among others described in greater detail below. The progress of the device through the vasculature 4 the signals produced by the system will also be described with reference to FIG. 16.

While the techniques described herein may be practiced in a number of clinical settings, the placement method 300 will be described for bedside catheter placement. The workflow presented in catheter placement method 300 begins with step 305 to measure approximate needed length of catheter. This step is recommended in order to verify the location indicated by the apparatus. This step is currently performed by the medical professional in the beginning of the procedure.

Next, at step 310, unpack sterile catheter with placement wire inserted and the sensor attached. In a preferred embodiment, the packaged catheter already contains a modified stylet with Doppler and ECG sensors. Currently, some PICC catheters are already packaged with stylets which are used by the medical professionals to push the catheter through the vasculature. Unlike the device embodiments of the present invention, conventional catheters and the corresponding stylets do not contain sensors suited to the multi-parameter processes described herein.

Next, at step 315, connect non-sterile user interface housing by bagging it with a sterile bag and piercing it with the connector end of the placement wire. In a preferred embodiment, the catheter containing the stylet with sensor is sterile and disposable while the user interface, control, and signal processing unit is reusable and potentially non-sterile. If the unit is not sterilized and cannot be used in the sterile field, it has to be bagged using a commercially available sterile bag. The catheter is then connected to the user interface unit by piercing the sterile bag with the stylet connector. Alternatively, a sterile cord or cable can be passed off the sterile field and subsequently attached to a non-sterile control unit without having to puncture a bag.

Next, at step 320, press self-test button on the user interface housing and wait to see the green LED blinking. Once the sensor is connected the system can execute a self test protocol to check connection and sensor. Of course, any colors, icons, and sounds or any other kind of graphical, alphanumeric, and/or audible elements can be used to indicate the proper connection.

Figure 16:
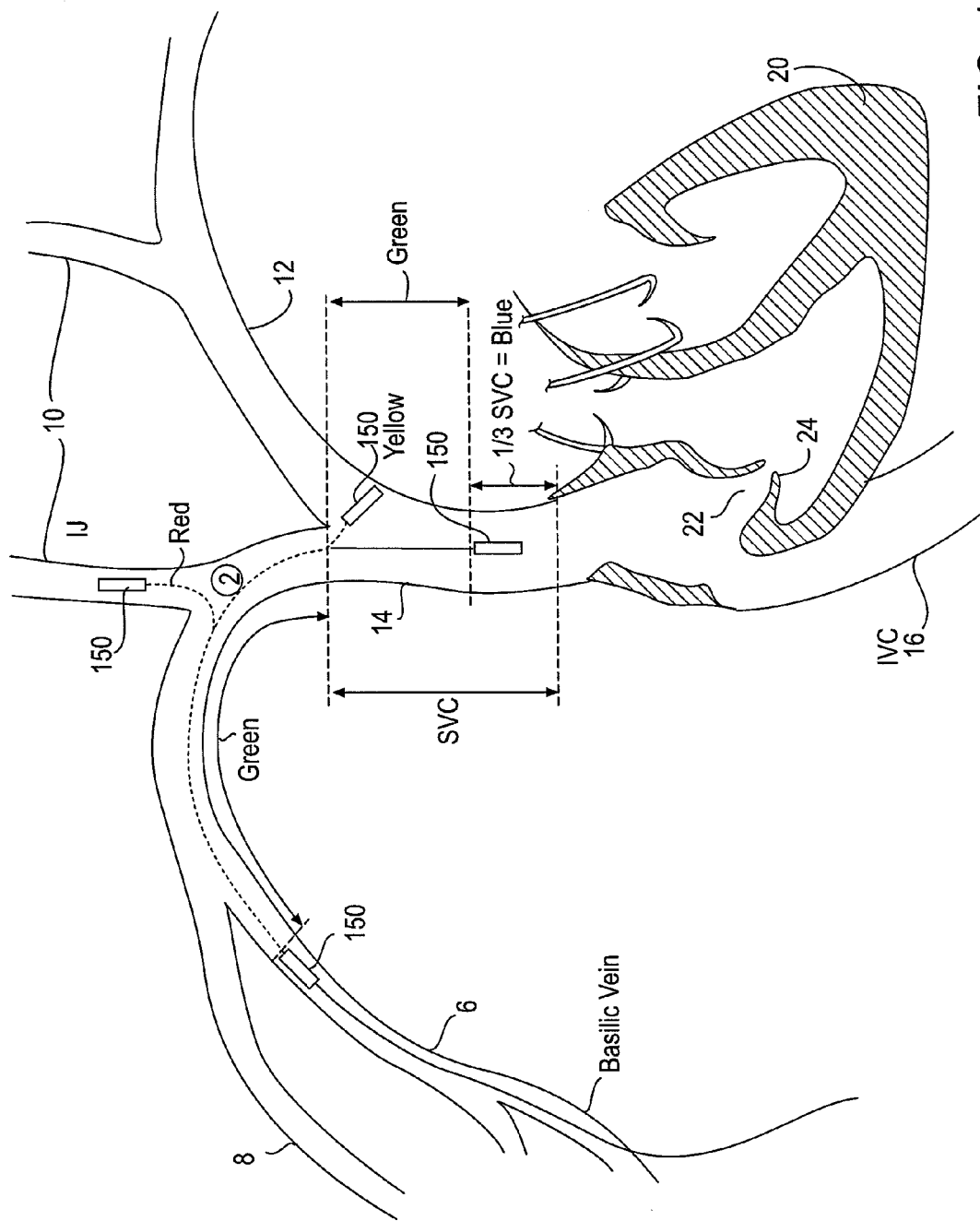
FIG. 16 illustrates an endovascular device within the vasculature at various locations according to the method of FIG. 15.

Next, at step 325, insert catheter into the vessel. This step is similar to the catheter introduction currently performed by medical professionals. One preferred insertion point is the basilic vein 6 as shown in FIG. 16.

Next, at step 330, hold in position until green light stops blinking (e.g., becomes solid green light). Once the catheter is in the vessel, it must be held in position for a few seconds or be slowly pushed forward. This step ensures that the signal processing algorithm can calibrate the data acquisition and pattern recognition to the current patient data. At this step a baseline ECG signal may be recorded and stored in memory. Additionally, the processing system will analyze the sensor date to confirm that the sensor is placed in a vein not an artery.

Next, at step 335, after receiving confirmation from the system that the sensor/catheter has been introduced into a vein, the user may start advancing the catheter and watch the green light to stay on. If the green light is on, it means that blood flows away from the catheter tip. This "green light" indication is the desired indication while advancing the catheter/sensor to the end position. FIG. 16 shows a correct position of the catheter in the basilic vein marked "Green" and meaning that the green light is on (along the dashed pathway).

Next, at step 340, if the light turns red, stop advancing and pull the catheter back until the light becomes green again. The light turns red when blood flows towards the catheter/sensor instead of away from it. This means that the catheter has been accidentally advanced into the jugular or other vein. In FIG. 16 this positioned is labeled "Red" and the catheter is shown in the internal jugular vein. In this situation the blood stream flowing towards the heart comes towards the device. In this situation the catheter must be pulled back to position labeled "2" in FIG. 16 and re-advanced on the correct path into the SVC. If accidentally the catheter is facing a vessel wall and cannot be advanced, the light turns yellow: position marked "yellow" in FIG. 16. In this situation the catheter must be pulled back until the yellow light is off and the green one is on again.

Next, at step 345, advance while green light on. The user keeps pushing while the catheter/sensor remain on the proper path toward the heart.

Next, at step 350, the user stops advancing when light turns blue. As illustrated in FIG. 16 the light turns blue when the lower third of the SVC has been identified. The light turns blue when the processing system has identified the unique flow pattern or physiological parameters (i.e., unique ECG wafe form) corresponding to the targeted placement region. In this illustrative method, the unique nature of the flow signature in the junction of the superior vena cava and the right atrium is identified and the blue indicator light illuminated. Next, at step 355, the user may verify actual length against the initially measured length. This step is used to double check the indication provided by the device and compare against the expected initially measured length for the target position.

Next, at step 360, remove stylet and attached sensor.

Next, at step 360, peel away introducer and then at step 370, secure catheter.

In additional alternative embodiments, there is provided a method for positioning an instrument in the vasculature of a body by processing a reflected ultrasound signal to determine the presence of a signal indicating a position where two or more vessels join. This method may be practiced in any of a wide variety of vascular junctions in both the venous and arterial vasculature. One exemplary position where two or more vessels join occurs where the two or more vessels include a superior vena cava and an inferior vena cava. A second exemplary position where two or more vessels join occurs where the two or more vessels include an inferior vena cava and a renal vein. According to one embodiment of the present invention, there is provided a method for positioning an instrument in the vasculature of a body using the instrument determine a location to secure a device within the vasculature of a body; and securing the device to the body to maintain the device in the location determined by the instrument. After the passage of some period of time (as is common with patients who wear catheters for an extended period of time, the instrument may be used to calculate the current position of the device. Next, using the known original position and the now determined current position, the system can determine if the device has moved from the original position.

It should be understood that various alternatives to the embodiments of the invention described herein may be employed in practicing the invention. For example if the target device position where in the brain for example, then the processing algorithms and outputs could be charged to indicate that movement into the jugular is the correct direction (green indicator) and that movement towards the heart would be an incorrect direction (red indicator). The system indications and parameters can be altered depending upon the location of and access route taken to various different target sites in the vasculature.

Having described the various components and operability of the inventive endovascular guidance system, numerous methods of endovascular guidance are provided.

In one aspect, the method of positioning an endovascular device in the vasculature of a body is accomplished by advancing the endovascular device into the vasculature and then transmitting a non-imaging ultrasound signal into the vasculature using a non-imaging ultrasound transducer on the endovascular device. Next, there is the step of receiving a reflected ultrasound signal with the non-imaging ultrasound transducer and then detecting an endovascular electrogram signal with a sensor on the endovascular device. Then there is the step of processing the reflected ultrasound signal received by the non-imaging ultrasound transducer and the endovascular electrogram signal detected by the sensor. Finally, there is the step of positioning the endovascular device based on the processing step.

The method of positioning an endovascular device in the vasculature of a body may also include additional or modified steps according to the specific application or process being performed. Numerous additional alternative steps are possible and may be used in a number of combinations to achieve the guidance and positioning results described herein. Additional steps may include verifying that the length of the endovascular device inserted into the body is equivalent to the estimated device length prior to the procedure and/or inputting into the system the length of the endovascular device inserted in the body. Additionally, the step of detecting an endovascular electrogram signal with a sensor positioned on a patient may be added. The sensor may be on the patient or a second or additional sensor on an endovascular device. There may also be added the step of comparing the endovascular electrogram signal from the sensor on the device or patient to the endovascular electrogram signal from the second sensor on the device.

The processing methods and algorithms may also be modified or combined to identify important or unique signatures useful in guidance, localization or correlation. The method may include different or customized software or programming for processing ultrasound and/or electrogram signal information. The processing may include processing of reflected ultrasound signal to identify the caval-atrial junction or to determine the highest average velocity of a velocity profile. The processing may include processing of the endovascular electrogram signal to determine: peak to peak amplitude changes in an electrogram complex; peak to peak amplitude changes of an QRS complex in an electrocardiogram; peak to peak amplitude changes of an R-wave in an electrocardiogram and or peak to peak amplitude changes of an P-wave in an electrocardiogram and, additionally or alternatively, to use electrogram information as a trigger to acquire and/or process ultrasound information.

The processing methods and algorithms may also be modified or combined to identify important or unique signatures to determine the position of a guided endovascular device relative to anatomical structures or positions in the body. Examples of these methods include performing the processing step to determine the position of the endovascular device relative to: the caval-atrial junction, the sinoatrial node, the superior vena cava, the internal jugular vein, and the subclavian vein.

The method of positioning an endovascular device in the vasculature of a body may be further modified to include using the endovascular device to determine a location to secure a device within the vasculature of a body and then securing the endovascular device along with the device to the body to maintain the device in the location determined by the endovascular device. The method of positioning an endovascular device in the vasculature of a body may also include the steps of calculating a current position of the device and then comparing the calculated current position of the device to a location indicated by the processing step.

The steps of the method may be performed in any order or repeated in whole or in part to achieve the desired positioning or placement of the guided endovascular device. For example, the method of positioning an endovascular device in the vasculature of a body may include performing the processing step and the positioning step until the endovascular device is positioned within the right atrium relative to the coronary sinus. Alternatively, the method of positioning an endovascular device in the vasculature of a body may include performing the processing step and the positioning step until the endovascular device is positioned within the left atrium relative to a pulmonary vein. Alternatively, the method of positioning an endovascular device in the vasculature of a body may also include performing the processing step and the positioning step until the endovascular device is positioned within the aorta.

This aspect may be modified to include, for example, an additional step of displaying a result of the processing step. The processing step may also include information related to venous blood flow direction. The venous flow direction may also include a flow directed towards the sensor and a flow directed away from the sensor. Additionally or alternatively, the result of the processing step may also include one or more of information related to venous blood flow velocity, information related to venous blood flow signature pattern, information related to a pressure signature pattern, information related to ultrasound A-mode information; information related to a preferential non-random direction of flow within a reflected ultrasound signal, information related to electrical activity of the brain, information related to electrical activity of a muscle, information related to electrical activity of the heart, information related to the electrical activity of the sinoatrial node; and information about the electrical activity of the heart from an ECG.

In another aspect, the displaying step may also be modified to include a visual indication of the position of the device. The displaying step may also be modified to include a visual or color based indication of the position of the device alone or in combination with a sound based indication of the position of the device.

The method of positioning an endovascular device in the vasculature of a body may also be modified to include the step of collecting the reflected ultrasound signal in synchrony with an endovascular electrogram signal received by the sensor. Additional alternatives are possible such as where the endovascular electrogram comprises electrical activity from the heart, from the brain or from a muscle. The collection step may be timed to correspond to physiological actions or timings. For example, the collecting step is performed in synchrony during the PR interval or in synchrony with a portion of the P-wave.

Other portions of an EEG, ECG or EMG electrogram may also be used for timing of collecting, processing and/or storing information from device based or patient based sensors. In one aspect of the method of positioning an endovascular device in the vasculature of a body, the transmitting step, the receiving step and the processing step are performed only when a selected endovascular electrogram signal is detected. In one version of the method, the selected endovascular electrogram signal is a portion of an ECG wave. In another version of the method, the selected endovascular electrogram signal is a portion of an EEG wave. In still another version of the method, the selected endovascular electrogram signal is a portion of an EMG wave.

The method of positioning an endovascular device in the vasculature of a body may also include identifying a structure in the vasculature using non-imaging ultrasound information in the reflected ultrasound signal. In one aspect, the non-imaging ultrasound information comprises using A-mode ultrasound to identify the structure in the vasculature. In another aspect, the non-imaging ultrasound information includes using Doppler ultrasound information to identify a flow pattern in proximity to the structure.

An another aspect of the method of positioning an endovascular device in the vasculature of a body the processing step is performed only on a portion of the reflected ultrasound signals that correspond to a selected electrogram trigger signal. This method may be employed, for example, when the selected electrogram trigger signal is a portion of an ECG wave, a portion of an EEG wave or a portion of an EMG wave.

In still other methods of positioning an endovascular device in the vasculature of a body, the processing step may be modified to include processing the reflected ultrasound signal by comparing the flow energy directed away from the endovascular device to the flow energy directed towards the endovascular device. In one aspect, there is a step of selecting for comparison the flow energy related to blood flow within the range of 2 cm/sec to 25 cm/sec.

In still other alternatives, the method of positioning an endovascular device in the vasculature of a body includes a processing step that has a step of processing the reflected ultrasound signal to detect an indicia of pulsatile flow in the flow pattern. The indicia of pulsatile flow may be any of a number of different parameters. The indicia of pulsatile flow may be: a venous flow pattern; an arterial flow pattern or an atrial function of the heart.

The method of positioning an endovascular device in the vasculature of a body may also include modification to the processing step to include the step of processing the endovascular electrogram signal to compare the relative amplitude of a P-wave to the relative amplitude of another portion of an electrocardiogram. In one aspect, the another portion of an electrocardiogram includes a QRS complex. The processing step may also be modified to include processing the reflective ultrasound signal to determine a blood flow velocity profile and processing the detected endovascular electrogram signal to determine a shape of the intravascular electrocardiogram. The processing step may be further modified to include the step of correlating the blood flow velocity profile and the shape of the intravascular electrocardiogram to determine the location of the endovascular device within the vasculature.

While preferred embodiments of the present invention have been shown and described herein, it will be obvious to those skilled in the art that such embodiments are provided by way of example only. Numerous variations, changes, and substitutions are incorporated herein by reference in their entirety. It is intended that the following claims define the scope of the invention and that methods and structures within the scope of these claims and their equivalents be covered thereby.

What is claimed is:

1. An endovascular device, comprising:
   an elongate body with a proximal end and a distal end;
   a non-imaging ultrasound transducer on the elongate body;
   an endovascular electrogram lead on the elongate body in a position that, when the endovascular device is in the vasculature, the endovascular electrogram lead is in contact with blood;
   a processor configured to receive and process a signal from the non-imaging ultrasound transducer and a signal from the endovascular electrogram lead; and
   a memory for storing instructions which, when executed by the processor, causes the processor to:
   calculate one or more blood flow features extracted from the non-imaging ultrasound signal, wherein the one or more blood flow features includes a ratio of a blood flow velocity away from the ultrasound transducer and a blood flow velocity towards the ultrasound transducer;
   calculate one or more electrogram features extracted from the electrogram signal, wherein the one or more electrogram features includes a P-wave amplitude; and
   determine a position of the elongate body within the vasculature based on the calculated one or more blood flow features and one or more electrogram features.

2. The endovascular device of claim 1 wherein the endovascular electrogram lead is positioned at the elongate body distal end.

3. The endovascular device of claim 1 wherein the electrical sensing segment of an endovascular electrogram lead is positioned within 3 cm of the elongate body distal end.

4. The endovascular device of claim 1 wherein the electrical sensing segment of an endovascular electrogram lead is positioned within 3 cm of the non-imaging ultrasound transducer.

5. The endovascular device of claim 1 wherein the electrical sensing segment of an endovascular electrogram lead is positioned proximal to the non-imaging ultrasound transducer.

6. The endovascular device of claim 1 further comprising:
   a second endovascular electrogram lead on the elongate body in a position that, when the endovascular device is in the vasculature, the second endovascular electrogram lead is in contact with blood.

7. The endovascular device of claim 6 wherein electrical sensing segment of the second endovascular electrogram lead is positioned about 5 cm from the endovascular electrogram lead.

8. The endovascular device of claim 6 wherein electrical sensing segment of the second endovascular electrogram lead is positioned about 5 cm from the elongate body distal end.

9. The endovascular device of claim 6 wherein electrical sensing segment of the second endovascular electrogram lead is positioned at a distance spaced apart from the endovascular electrogram lead so that the second endovascular electrogram lead detects a baseline electrogram signal when the endovascular electrogram lead is detecting a target electrogram signal.

10. The endovascular device of claim 6 wherein electrical sensing segment of the second endovascular electrogram lead is positioned at a distance related to the length of the superior vena cava such that when the endovascular electrogram lead is in the superior vena cava the second endovascular electrogram lead is outside of the superior vena cava.

11. The endovascular device of claim 6 wherein electrical sensing segment of the second endovascular electrogram lead is positioned such that when the electrical sensing segment of the endovascular electrogram lead is positioned to detect a targeted electrogram signal from the heart the electrical sensing segment of the second endovascular electrogram lead is positioned to detect a comparison baseline ECG signal.

12. The endovascular device of claim 6 wherein electrical sensing segment of the second endovascular electrogram lead is positioned such that when the electrical sensing segment of the endovascular electrogram lead is positioned to detect a targeted electrogram signal from the brain the electrical sensing segment of the second endovascular electrogram lead is positioned to detect a comparison baseline EEG signal.

13. The endovascular device of claim 6 wherein electrical sensing segment of the second endovascular electrogram lead is positioned such that when the electrical sensing segment of the endovascular electrogram lead is positioned to detect a targeted electrogram signal from a muscle the electrical sensing segment of the second endovascular electrogram lead is positioned to detect a comparison baseline EMG signal.

14. The endovascular device of claim 1 wherein the endovascular electrogram lead is moveable from a stowed condition within the elongate body and a deployed condition outside of the elongate body.

15. The endovascular device of claim 14 wherein the stowed endovascular electrogram lead curves the distal end of the endovascular device.

16. The endovascular device of claim 14 wherein when the endovascular electrogram lead is in the stowed condition the electrical sensing segment is positioned to detect an electrogram signal.

17. The endovascular device of claim 1 further comprising: a steering element connected to the endovascular lead for directing the proximal end of the elongate body.

18. The endovascular device of claim 17 wherein the steering element provides torque to the elongate body distal end.

19. The endovascular device of claim 1 wherein the endovascular electrogram lead in use extends at least partially about the elongate body.

20. The endovascular device of claim 1 wherein the endovascular lead further comprises: an atraumatic tip.

21. The endovascular device of claim 1 wherein the endovascular electrogram lead is formed from a shape memory alloy.

22. The endovascular device of claim 1 wherein the endovascular electrogram lead is adapted for use to move the ultrasound sensor away from a blood vessel wall.

23. The endovascular device of claim 1 wherein the endovascular device comprises a coated metal braided structure and a portion of the coating on the metal braided structure is removed and the exposed metal braided structure functions as an endovascular electrogram lead electrical sensing segment.

24. The endovascular device of claim 1 further comprising: an atraumatic tip on the distal end of the endovascular device.

25. The endovascular device of claim 24 wherein the atraumatic tip comprises an ultrasound lens.

26. The endovascular device of claim 25 wherein the ultrasound lens is a divergent lens.

27. The endovascular device of claim 1 further comprising: an opening in the elongate body; and a lumen within the elongate body in communication with the opening and the elongate body proximal end.

28. The endovascular device of claim 1 further comprising an additional sensor on the endovascular device for measuring a physiological parameter.

29. The endovascular device of claim 28 wherein the additional sensor is an optical sensor.

30. The endovascular device of claim 29 wherein the physiological parameter is related to an optical property detected within the vasculature.

31. The endovascular device of claim 28 wherein the additional sensor is a pressure sensor.

32. The endovascular device of claim 31 wherein the physiological parameter is related to a pressure measurement obtained within the vasculature.

33. The endovascular device of claim 28 wherein the additional sensor is an acoustic sensor.

34. The endovascular device of claim 33 wherein the physiological parameter is related to an acoustic signal detected within the vasculature.

35. The endovascular device of claim 1 wherein the elongate body comprises a catheter.

36. The endovascular device of claim 1 wherein the elongate body comprises a guide wire.

37. The endovascular device of claim 1 wherein the elongate body comprises a stylet.

38. The endovascular device of claim 1 wherein the elongate body is adapted to deliver a therapy to the patient.

39. The endovascular device of claim 1 wherein the elongate body is adapted to provide endovascular access for another device.

40. The endovascular device of claim 1 wherein the processor is further configured to receive and process a signal from the non-imaging ultrasound transducer comprising a signal from at least one of the group consisting of: a venous blood flow direction, a venous blood flow velocity, a venous blood flow signature pattern, a pressure signature pattern, A-mode information and a preferential non-random direction of flow and to receive and process a signal from the endovascular electrogram lead the signal comprising at least one of the group consisting of: an electrocardiogram signal, a P-wave pattern, a QRS-complex pattern, a T-wave pattern, an EEG signal and an EMG signal.

41. The endovascular device of claim 1 wherein the processor is configured to process the signal from the non-imaging ultrasound transducer to determine a flow directed towards the ultrasound transducer and a flow directed away from the ultrasound transducer.

42. The endovascular device of claim 1 wherein the processor is configured to process the signal from the non-imaging ultrasound transducer to determine a venous blood flow signature pattern.

43. The endovascular device of claim 1 wherein the processor is configured to process only a portion of the signal from the non-imaging ultrasound transducer that corresponds to a selected electrogram trigger signal.

44. The endovascular device of claim 43 wherein the selected electrogram trigger signal is a portion of an ECG wave.

45. The endovascular device of claim 1 wherein the processor is configured to process the endovascular electrogram signal to determine peak to peak amplitude changes of an QRS complex in an electrocardiogram.

46. The endovascular device of claim 1 wherein the processor is configured to process the endovascular electrogram signal to determine peak to peak amplitude changes of an R-wave in an electrocardiogram.

47. The endovascular device of claim 1 wherein the processor is configured to process the endovascular electrogram signal to determine peak to peak amplitude changes of an P-wave in an electrocardiogram.

48. The endovascular device of claim 1 wherein the processor is configured to process the endovascular electrogram signal to compare the relative amplitude of an P-wave to the relative amplitude of another portion of an electrocardiogram.

49. The endovascular device of claim 1 wherein the processor is configured to process the ultrasound signal to determine a blood flow velocity profile and processing the endovascular electrogram signal to determine a shape of the intravascular electrocardiogram.

50. The endovascular device of claim 49 wherein the processor is configured to correlate the blood flow velocity profile and the shape of the intravascular electrocardiogram to determine the location of the endovascular device within the vasculature.

51. The endovascular device of claim 1, wherein the memory for storing instructions which, when executed by the processor, causes the processor to further determinine whether the elongate body has reached the superior vena cava based on the calculated one or more non-pulsatile blood flow features and one or more electrogram features.

52. An endovascular device, comprising:
   an elongate body with a proximal end and a distal end;
   a non-imaging ultrasound transducer on the elongate body;
   an endovascular electrogram lead on the elongate body in a position that, when the endovascular device is in the vasculature, the endovascular electrogram lead is in contact with blood;
   a processor configured to receive and process a signal from the non-imaging ultrasound transducer and a signal from the endovascular electrogram lead; and
   a memory for storing instructions which, when executed by the processor, causes the processor to:
   calculate one or more blood flow features extracted from the non-imaging ultrasound signal, wherein the one or more blood flow features includes a ratio of a blood flow power spectrum away from the ultrasound transducer and a blood flow power spectrum towards the ultrasound transducer;
   calculate one or more electrogram features extracted from the electrogram signal, wherein the one or more electrogram features includes a P-wave amplitude; and
   determine a position of the elongate body within the vasculature based on the calculated one or more blood flow features and one or more electrogram features.

* * * * *